US011053480B2

(12) United States Patent
Pfleger et al.

(10) Patent No.: US 11,053,480 B2
(45) Date of Patent: *Jul. 6, 2021

(54) GENE CONSTRUCT ENCODING MUTANT THIOESTERASE, MUTANT THIOESTERASE ENCODED THEREBY, TRANSFORMED HOST CELL CONTAINING THE GENE CONSTRUCT, AND METHOD OF USING THEM TO PRODUCE MEDIUM-CHAIN FATTY ACIDS

(71) Applicants: WISCONSIN ALUMNI RESEARCH FOUNDATION, Madison, WI (US); The Penn State Research Foundation, University Park, PA (US)

(72) Inventors: Brian F. Pfleger, Madison, WI (US); Nestor Jose Hernandez-Lozada, Jena (DE); Costas Maranas, State College, PA (US); Matthew Grisewood, Mountaintop, PA (US)

(73) Assignees: WISCONSIN ALUMNI RESEARCH FOUNDATION, Madison, WI (US); THE PENN STATE RESEARCH FOUNDATION, University Park, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/930,147

(22) Filed: May 12, 2020

(65) Prior Publication Data
US 2020/0339966 A1    Oct. 29, 2020

Related U.S. Application Data

(63) Continuation of application No. 16/535,305, filed on Aug. 8, 2019, now Pat. No. 10,689,631, which is a continuation of application No. 15/630,442, filed on Jun. 22, 2017, now Pat. No. 10,421,951.

(60) Provisional application No. 62/353,069, filed on Jun. 22, 2016.

(51) Int. Cl.
C12N 9/16    (2006.01)

(52) U.S. Cl.
CPC ........ *C12N 9/16* (2013.01); *C12Y 301/02002* (2013.01)

(58) Field of Classification Search
CPC .......................... C12N 9/16; C12Y 301/02002
See application file for complete search history.

(56) References Cited

U.S. PATENT DOCUMENTS

| | | |
|---|---|---|
| 4,837,148 A | 6/1989 | Cregg |
| 4,929,555 A | 5/1990 | Cregg et al. |
| 5,077,214 A | 12/1991 | Guarino et al. |
| 5,614,620 A | 3/1997 | Liao et al. |
| 5,679,543 A | 10/1997 | Lawlis |
| 5,873,847 A | 2/1999 | Bennett et al. |
| 5,955,329 A | 9/1999 | Yuan et al. |
| 8,617,856 B2 | 12/2013 | Pfleger et al. |
| 9,175,234 B2 | 11/2015 | Hom et al. |
| 9,587,231 B2 | 3/2017 | Hom et al. |
| 10,421,951 B2 * | 9/2019 | Pfleger ........... C12Y 301/02002 |
| 10,689,631 B2 * | 6/2020 | Pfleger ........... C12Y 301/02002 |

FOREIGN PATENT DOCUMENTS

| | | |
|---|---|---|
| EP | 238 023 A2 | 9/1987 |
| WO | WO 96/00787 A1 | 1/1996 |
| WO | WO 2007/136762 A2 | 11/2007 |
| WO | WO 2008/119082 A2 | 10/2008 |

OTHER PUBLICATIONS

Alper et al. (2005), Tuning genetic control through promoter engineering, *PNAS* 102 (36):12678-83.
Altschul S F, Gish W, Miller W, Myers E W, and Lipman D J (1990) "Basic local alignment search tool." J. Mol. Biol. 215(3): 403-410.
Beach et al. (1981), Functionally homologous cell cycle control genes in budding and fission yeast. *Nature* 300:706.
Becker and Guarente, High-Efficiency Transformation of Yeast by Electroporation, In Abelson, J. N. and Simon. M. I., editors, Guide to Yeast Genetics and Molecular Biology, Methods in Enzymology, vol. 194, pp. 182-157, Academic Press, Inc., New York.
Brooks BR, et al. (2009) "CHARMM: the biomolecular simulation program," *J Comput Chem* 30(10):1545-1614.
Chang and Cohen, (1979), High Frequency Transformation of *Bacillus subtilis* Protoplasts *Molecular General Genetics*, 168 111-115.
Chen G. et al. (2012) Cloning of acyl-ACP thioesterase FatA from *Arachis hypogaea* L. and its expression in *Escherichia coli. Journal of biomedicine & biotechnology* 2012:652579.
Cho & Cronan (1993) "*Escherichia coli* Thioesterase-I, Molecular-Cloning and Sequencing of the Structural Gene and Identification as a Periplasmic Enzyme," *Journal of Biological Chemistry* 268(13):9238-9245.
Choi YJ & Lee SY (2013) "Microbial production of short-chain alkanes," *Nature* 502(7472):571-574.
Cregg et al. (1985). *Pichia pastoris* as a Host System for Transformations, *Mol. Cell. Biol.* 5:3376-3385.
Das et al. (1984), Transformation of *Kluyveromyces fragilis, J. Bacteriol.*158:1165-1167.
Davidow et al. (1985), Integrative transformation of the east *Yarrowia lipolytica, Curr. Genet.* 10:39-48.

(Continued)

Primary Examiner — Tekchand Saidha
(74) *Attorney, Agent, or Firm* — Daniel A. Blasiole; DeWitt LLP

(57) ABSTRACT

Unnatural, mutated thioesterases having an amino acid sequence that is at least 80% identical to SEQ. ID. NO: 1 and having substitutions at one or more of amino acid positions I107, R108, L109, S122, M141, E142, Y145, and L146, gene constructs encoding and configured to express the mutated thioesterases in a transformed host cell and host cells transformed to contain the gene constructs.

20 Claims, 6 Drawing Sheets
(6 of 6 Drawing Sheet(s) Filed in Color)
Specification includes a Sequence Listing.

(56) References Cited

OTHER PUBLICATIONS

De Louvencourt et al. (1983), Transformation of *Kluyveromyces lastic* by Killer Plasmid DNA, *J. Bacteriol.* 154:737-742.

Dong SB, et al. (2014) Cloning, characterization, and expression analysis of acyl-acyl carrier protein (ACP)-thioesterase B from seeds of Chinese Spicehush (*Lindera communis*), *Gene* 542(1):16-22.

Dormann, Voelker, & Ohlrogge (1995) "Cloning and Expression in *Escherichia coli* of a Novel Thioesterase from *Arabidopsis thaliana* Specific for Long-Chain Acyl-Acyl Carrier Proteins," *Arch Biochem Biophys* 316(1):612-618.

Dubnau and Davidoff-Abelson (1971), Fate of Transforming DNA following uptake by Competent *Bacillus subtilis, Journal of Molecular Biology*, 56: 209-221.

Gaillardin et al. (1985), Integrative transformation of the yeast *Yarrowia lipolytica, Curr. Genet.* 10:49-58.

Ganeva et al. (1994), Influence of glucose and other substrates on electric field and polyethylene glycol-mediated transformation of intact yeast cells, *FEMS Microbiology Letters* 121:159-64. See also Molecular Cloning: A Laboratory Manual, 4$^{th}$ Ed.

Ghosh SK et al. (2007), Characterization and cloning of a stearoyl/oleoyl specific fatty acyl-acyl carrier protein thioesterase from the seeds of Madhuca longifolia (latifolia). *Plant Physiol Bioch* 45(12):887-897.

Gleeson et al. (1986), Transformation of the Methylotrophic Yeast *Hansenula polymorpha, J. Gen. Microbiol.* 132:3459-3465.

Gong Y, et al. (2011) Characterization of a novel thioesterase (PtTE) from *Phaeodactylum tricornutum. Journal of basic microbiology* 51(6):666-672.

Green, Michael R. and Sambrook, Joseph, "Molecular Cloning: A Laboratory Manual, 4$^{th}$ Ed.," © 2012, Cold Spring Harbor Lab Press. ISBN-10: 1936113422 (Book—Copy Not Provided).

Hall M. et al. (2009) "The WEKA data mining software: an update," *SIGKDD Explor. Newsl.*, 11(1):10-18.

Hinnen et al. (1978), Transformation of yeast, *Proc. Natl. Acad. Sci. USA* 75:1929-1933.

Howard TP, et al. (2013) "Synthesis of customized petroleum-replica fuel molecules by targeted modification of free fatty acid pools in *Escherichia coli," PNAS* 110(19):7636-7641.

Humphrey W, et al. (1996) "VMD: visual molecular dynamics," *J Mol Graphics.* 14(1):27-38.

Ito et al. (1983), Transformation of Intact Yeast Cells Treated with Alkali Cations, *J. Bacteriol.* 153:163-168.

Jha JK, et al. (2006) "Cloning and functional expression of an acyl-ACP thioesterase FatB type from Diploknema (Madhuca) butyracea seeds in *Escherichia coli," Plant Physiol Bioch* 44(11-12):645-655.

Jha JK et al. (2007) Functional expression of an acyl carrier protein (ACP) from Azospirillum brasilense alters fatty acid profiles in *Escherichia coli* and Brassica juncea. *Plant physiology and biochemistry: PPB Societe francaise de physiologic vegetale* 45(67):490-500.

Jing et al. (2011) "Phylogenetic and experimental characterization of an acyl-ACP thioesterase family reveals significant diversity in enzymatic specificity and activity," *BMC Biochem* 12:44.

Jing F (2013) Characterization of acyl-ACP thioesterases for the purpose of diversifying fatty acid synthesis pathway. Dissertation/Thesis (ProQuest Dissertations Publishing).

Jones et al. (1995), Palmitoyl-Acyl Carrier Protein (ACP) Thioesterase and the Evolutionary Origin of Plant Acyl-ACP Thioesterases, *The Plant Cell*, 7:359-371.

Khlebnikov, Datsenko, Skaug, Wanner, and Keasling (2001) "Homogeneous expression of the PBAD promoter in *Escherichia coli* by constitutive expression of the low-affinity high-capacity AraE transporter," *Microbiology* 147:3241-3247.

Koehler and Thorne (1987), *Bacillus subtilis* (natto) Plasmid pLS20 Mediates Interspecies Plasmid Transfer, *Journal of Bacteriology*, 169:5271-5278.

Kuhlman and Baker. (Kuhlman & Baker (2000) "Native protein sequences are close to optimal for their structures," *PNAS* 97(19):10383-10388.

Kunze et al. (1985), Transformation of the industrially important yeasts *Candida maltose* and *Pichia guilliermondii, J. Basic Microbiol.* 25:141-144.

Kurtz et al. (1986), Integrative Transformation of *Candida albicans*, Using a Cloned *Candida* ADE2 Gene. *Mol. Cell. Biol.* 6:142-149.

Lee SK, Chou H, Ham TS, Lee TS, & Keasling JD (2008) "Metabolic engineering of microorganisms for biofuels production: from bugs to synthetic biology to fuels," *Curr Opin Biotech* 19(6):556-563.

Lee S., et al. (2014) Enhanced free fatty acid production by codon-optimized *Lactococcus lactis* acyl-ACP thioesterase gene expression in *Escherichia coli* using crude glycerol. *Enzyme and microbial technology* 67:8-16.

Lebigot EO (2014) "Uncertainties: a Python package for calculations with uncertainties," published online at https://pythonhosted.org/uncertainties/_downloads/uncertaintiesPythonPackage.pdf.

Lo, Lin, Shaw, & Liaw (2005) "Substrate Specificities of *Escherichia coli* Thioesterase I/Protease I/Lysophospholipase L$_1$ Are Governed by Its Switch Loop Movement," *Biochemistry* 44(6): 1971-1979.

Lu, Vora & Khosla (2008) "Overproduction of free fatty acids in *E. coli*: implications for biodiesel production," *Metabolic Engineering* 10(6):333-339.

Malardier et al., (1989), Cloning of the nitrate reductase gene (niaD) of *Aspergillus nidulans* and its use for transformation of *Fusarium oxysporum, Gene*, 78:147-156.

Manivasakam & Schiestl, (1993) *Nucleic Acids Research* 21 (18):4414-5.

Marchler-Bauer A, et al. (2015) "CDD: NCBI's Conserved Domain Database," *Nucleic Acids Res* 43(D1):D222-D226.

Mayer & Shanklin (2007) Identification of amino acid residues involved in substrate specificity of plant acyl-ACP thioesterases using a bioinformatics-guided approach. *BMC Plant Biol* 7.

Michael R. Green and Joseph Sambrook, "Molecular Cloning: A Laboratory Manual, 4th Ed.," © 2012, Cold Spring Harbor Lab Press, ISBN-10: 1936113422. (Book—Copy Not Provided).

Pantazes, Grisewood, Li, Gifford, and Maranas (Feb. 5, 2015) "The Iterative Protein Redesign and Optimization (IPRO) suite of programs," *J Comput Chem.* 36(4):251-63 (published online Dec. 2, 2014).

Phillips JC, et al. (2005) "Scalable molecular dynamics with NAMD," *J Comput Chem* 26(16):1781-1802.

Reeves et al. (1992) *FEMS Microbiology Letters* 99:193-198; Manivasakam and Schiestl (1993) *Nucleic Acids Research* 21 (18):4414-5.

Richardson, Keedy, and Richardson (2013) "The Plot Thickens: More Data, More Dimensions, More Uses. Biomolecular Forms and Functions," in "A Celebration of 50 Years of the Ramachandran Map" © 2013, World Scientific Publishing Co. Pte. Ltd., Singapore. at pp. 46-61.

Roggenkamp et al. (1986), Transformation of the methylotrophic yeast *Hansenula polymorpha* by autonomous replication and integration vectors, *Mol. Gen. Genet.* 202:302-308.

Roujeinikova A, et al. (2007) "Structural studies of fatty acyl-(acyl carrier protein) thioesters reveal a hydrophobic binding cavity that can expand to fit longer substrates," *J Mol Biol* 365(1):135-145.

Saraf, Moore, Goodey, Cao, Benkovic, and Maranas (2006), "IPRO: An Iterative Computational Protein Library Redesign and Optimization Procedure," *Biophysical Journal* 90:4167-4180.

Schiestl et al. (1993). Introducing DNA into Yeast by Transformation, *Methods: A Comparison to Methods in Enzymology*, 5:79-85.

Serrano-Vega, MJ, et al. (2003). Cloning, characterization and structural model of a FatA-type thioesterase from sunflower seeds (*Helianthus annuus* L.) *Planta* 221(6):868-880.

Shigekawa and Dower (1988), Electroporation of Eukaryotes and Prokaryotes: A General Approach to the Introduction of Macromolecules into Cells, *Biotechniques*, 6:742-751.

Steen EJ, et al. (2010) "Microbial production of fatty-acid-derived fuels and chemicals from plant biomass," *Nature* 463(7280):559-U182.

(56) References Cited

OTHER PUBLICATIONS

Sugiura et al. (1993), Minimal Essential Origin of Plasmid pSC101 Replication: Requirement of a Region Downstream of Interons, *J. Bacteriol.* 175(18):5993-6001.

Van Den Berg et al. (1990), *Kluyveromyces* as a Host for Heterologous Gene Expression: Expression and Secretion of Prochymosin, Bio/Technology 8:135.

Vanommeslaeghe, Raman, & Mackerell (Jan. 2012) "Automation of the CHARMM General Force Field (CGenFF) II: Assignment of Bonded Parameters and Partial Atomic Charges," *J Chem Inf Model* 52(12):3155-3168.

Vanommeslaeghe & Mackerell (Feb. 2012) "Automation of the CHARMM General Force Field (CGenFF) I: Bond Perception and Atom Typing," *J Chem Inf Model* 52(12):3144-3154.

Voelker TA & Davies HM (1994) "Alteration of the specificity and regulation of fatty acid synthesis of *Escherichia coli* by expression of a plant medium-chain acyl-acyl carrier protein thioesterase," *J Bacteriol* 176(23):7320-7327.

Young and Spizizen (1961), Physiological and Genetic Factors Affecting Transformation of *Bacillus subtilis, Journal of Bacteriology*, 81:823-829.

Zhang, Li, Agrawal, & San (2011) "Efficient free fatty acid production in *Escherichia coli* using plant acyl-ACP thioesterases," *Metabolic Engineering* 13(6):713-722.

Zheng Y et al (2012) Boosting the free fatty acid synthesis of *Escherichia coli* by expression of a cytosolic Acinetobacter baylyi thioesterase. *Biotechnology for biofuels* 5(1):76.

\* cited by examiner

GENE CONSTRUCT ENCODING MUTANT THIOESTERASE, MUTANT THIOESTERASE ENCODED THEREBY, TRANSFORMED HOST CELL CONTAINING THE GENE CONSTRUCT, AND METHOD OF USING THEM TO PRODUCE MEDIUM-CHAIN FATTY ACIDS

CROSS-REFERENCE TO RELATED APPLICATIONS

This application is a continuation of U.S. application Ser. No. 16/535,305, filed Aug. 8, 2019, which is a continuation of U.S. application Ser. No. 15/630,442, filed Jun. 22, 2017, which issued as U.S. Pat. No. 10,421,951 on Sep. 24, 2019, and which claims priority to U.S. Provisional Application 62/353,069, filed Jun. 22, 2016, all of which are incorporated herein by reference.

FEDERAL FUNDING STATEMENT

This invention was made with government support under CBET1149678 and CBET0967062 awarded by the National Science Foundation. The government has certain rights in the invention.

BACKGROUND

Free fatty acids (FFAs) are energy-rich molecules capable of serving as precursors for the production of liquid transportation fuels and high-value oleochemicals. Fuel properties are dictated by the aliphatic chain length and degree of saturation of the FFA precursors. Medium-chain (C6-C12) FFA feedstocks can be converted to hydrocarbons with fuel properties comparable to gasoline, diesel, or jet fuel. See, for example, Choi Y J & Lee S Y (2013) "Microbial production of short-chain alkanes," *Nature* 502(7472):571-574; and Lee S K, Chou H, Ham T S, Lee T S, & Keasling J D (2008) "Metabolic engineering of microorganisms for biofuels production: from bugs to synthetic biology to fuels," *Curr Opin Biotech* 19(6):556-563. Fuels derived from microbially produced FFAs would facilitate reduction of the carbon footprint and, unlike bioethanol, avoid expensive and laborious infrastructure and engine remodeling. (Howard T P, et al. (2013) "Synthesis of customized petroleum-replica fuel molecules by targeted modification of free fatty acid pools in *Escherichia coli*," *PNAS* 110(19):7636-7641.

*Escherichia coli* is a popular microbial host for FFA production because of its established type II fatty acid biosynthesis (FAB) pathway, short doubling time, and genetic tractability. The *E. coli* FAB pathway is initiated by the ATP-dependent carboxylation of acetyl-CoA to malonyl-CoA. Subsequently, CoA is exchanged with acyl carrier protein (ACP), the recognition tag of FAB, producing malonyl-ACP. Malonyl-ACP and acetyl-CoA are condensed to yield acetoacetyl-ACP. The alkyl chain of the β-ketoacyl-ACP is successively extended by two carbon atoms that originate from additional malonyl-ACP. This cycle is terminated by the acyl-ACP thioesterase, which hydrolyzes the thioester bond to generate the FFA and ACP. The specificity of the acyl-ACP thioesterase controls the terminal aliphatic chain length and chemical properties of the FFA product composition. Regulation of the FFA chain length produced through the FAB pathway has typically been achieved by the overexpression of the two native *E. coli* thioesterases (TesA and TesB), or heterologous expression of various plant and bacterial thioesterases (see Table 1, below), which exhibit a wide range of substrate specificities See Choi & Lee (2013), supra, as well as Steen E J, et al. (2010) "Microbial production of fatty-acid-derived fuels and chemicals from plant biomass," *Nature* 463(7280):559-U182; Jing F Y, et al. (2011) "Phylogenetic and experimental characterization of an acyl-ACP thioesterase family reveals significant diversity in enzymatic specificity and activity," *BMC Biochem* 12:44; Zhang, Li, Agrawal, & San (2011) "Efficient free fatty acid production in *Escherichia coli* using plant acyl-ACP thioesterases," *Metabolic Engineering* 13(6):713-722; Lu, Vora & Khosla (2008) "Overproduction of free fatty acids in *E. coli*: implications for biodiesel production," *Metabolic Engineering* 10(6):333-339; Voelker T A & Davies H M (1994) "Alteration of the specificity and regulation of fatty acid synthesis of *Escherichia coli* by expression of a plant medium-chain acyl-acyl carrier protein thioesterase," *J Bacteriol* 176(23):7320-7327; and Dormann, Voelker, & Ohlrogge (1995) "Cloning and Expression in *Escherichia coli* of a Novel Thioesterase from *Arabidopsis-Thaliana* Specific for Long-Chain Acyl-Acyl Carrier Proteins," *Arch Biochem Biophys* 316(1):612-618.

Several of these thioesterases have been evolved to further diversify the gamut of attainable FFA compositions. Despite this diversification, very few thioesterases are specific towards a unique aliphatic chain length. Of these studied thioesterases, 'TesA (a cytosolic TesA that lacks the N-terminal signal peptide and whose crystal structure has been elucidated) produces one of the highest FFA titers. See Steen (2010) and Choi & Lee (2013), supra, and Cho & Cronan (1993) "*Escherichia coli* Thioesterase-I, Molecular-Cloning and Sequencing of the Structural Gene and Identification as a Periplasmic Enzyme," *Journal of Biological Chemistry* 268(13):9238-9245 and Lo, Lin, Shaw, & Liaw (2005) "Substrate Specificities of *Escherichia coli* Thioesterase I/Protease I/Lysophospholipase L1 Are Governed by Its Switch Loop Movement," *Biochemistry* 44(6):1971-1979. In spite of these clear advantages, 'TesA has broad substrate specificity that necessitates costly downstream separation (Steen (2010) and Choi & Lee (2013), supra).

Acyl-acyl carrier protein (Acyl-ACP) thioesterases play an essential role in chain termination during de novo fatty acid synthesis. These thioesterases terminate fatty acyl group extension by catalyzing the hydrolysis of an acyl group on a fatty acid. Thus, because acyl-ACP thioesterases catalyze termination of the iterative chain extension process, the action of acyl-ACP thioesterases determines, in large part, the ultimate carbon chain length of the fatty acids found in any given wild-type organism. See, for example, Aubrey Jones, H. Maelor Davies, and Toni A. Voelker (1995) "Palmitoyl-Acyl Carrier Protein (ACP) "Thioesterase and the Evolutionary Origin of Plant Acyl-ACP Thioesterases," *The Plant Cell*, 7:359-371.

The carbon chain length of fatty acids is economically significant because the natural occurrence of certain types of fatty acids, such as medium-chain fatty acids (carbon chain of 6 to 12 carbon atoms) in general and C8 carbon chain length fatty acids in particular, is notably less than long-chain fatty acids (carbon chain longer than 12 carbon atoms). C8 fatty acids are also notable because they are both renewable and also suitable as a precursor to liquid transportation fuels, i.e., biofuel.

Biofuels such as biodiesel are biodegradable, clean-burning combustible fuels made of medium- to long-chain alkanes and esters. Biodiesel can be used in most internal combustion diesel engines in either a pure form, which is referred to as "neat" biodiesel, or as a mix in any concentration with regular, petroleum-derived diesel. An advantage of biodiesel is that it can be generated from renewable, non-petroleum sources. Current methods of making biodiesel involve transesterification of triacylglycerides (mainly vegetable oil). However, this leads to a product comprising a mixture of fatty acid esters and glycerin as an unwanted by-product. In short, because transesterification yields heterogeneous product and an unwanted glycerin by-product, transesterification encompasses unavoidable economic inefficiencies. In addition, the presence of methyl esters and ethyl esters in traditional biodiesel leads to unwanted gelation properties at temperature below about 0° C.

PCT Publication No. WO 2007/136762, published Nov. 29, 2007, to Keasling et al., discloses recombinant microorganisms that are capable of synthesizing products derived from the fatty acid synthetic pathway, including fatty acid esters and fatty alcohols.

PCT Publication No. WO 2008/119082, published Oct. 2, 2008, to Hu et al., discloses genetically engineered cells and microorganisms that produce products from the fatty acid biosynthetic pathway. The products are noted as being particularly useful as biofuels. The Hu et al. publication describes recombinant cells that utilize overexpression of acyl-CoA synthetase enzymes to more efficiently produce fatty acid derivatives.

U.S. Pat. No. 5,955,329, issued Sep. 21, 1999, to Yuan et al., discloses genetically engineered plant acyl-ACP thioesterase proteins having altered substrate specificity. The engineered acyl-ACP thioesterase exhibited an altered substrate specificity as compared to the wild-type acyl-ACP thioesterase.

U.S. Pat. No. 8,617,856, issued Dec. 31, 2013, to Pfleger and Lennen, describes transformed hosts for overproducing fatty acids. The hosts include an exogenous nucleic acid encoding a thioesterase and, optionally, an exogenous nucleic acid encoding an acetyl-CoA carboxylase, wherein an acyl-CoA synthetase in the host is functionally deleted. The hosts preferably include the nucleic acid encoding the thioesterase at an intermediate copy number.

U.S. Pat. No. 9,175,234, issued Nov. 3, 2015 to Hom et al. describes an engineered thioesterase enzyme which converts a C10, C12, or C14 acyl-ACP substrate to a fatty acid derivative with a greater activity as compared to a wild-type thioesterase enzyme. This particular mutant thioesterase has a substitution at an amino acid position selected from the group consisting of positions 78, 80, 101, 108, 111, 117, 118, 122, 145, 152, and 178.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In FIG. 4A, the activity of WT 'TesA (left panel) and R3.M4 (right panel), as a function of substrate concentration, is shown for six different acyl-CoA substrates. Open and closed circles indicate measurements taken in separate days. The competitive activity assays (FIGS. 4B, 4C, 4D, and 4E) were performed to see the effect that an increase in C14-CoA and C16-CoA would have on the C8CoA activity of the enzymes. Competitive activity assays were performed at a constant C8-CoA concentration of 50 µM and variable concentrations of C14-CoA (FIG. 4B for WT and FIG. 4C for R3.M4) and C16-CoA (panel (D) for WT and panel (E) for R3.M4). In all cases, the activity of 'TesA was impacted by the C14-CoA and C16-CoA in a concentration-dependent manner consistent with the original assay in FIG. 4A.

SEQUENCE LIST

Figure 1:
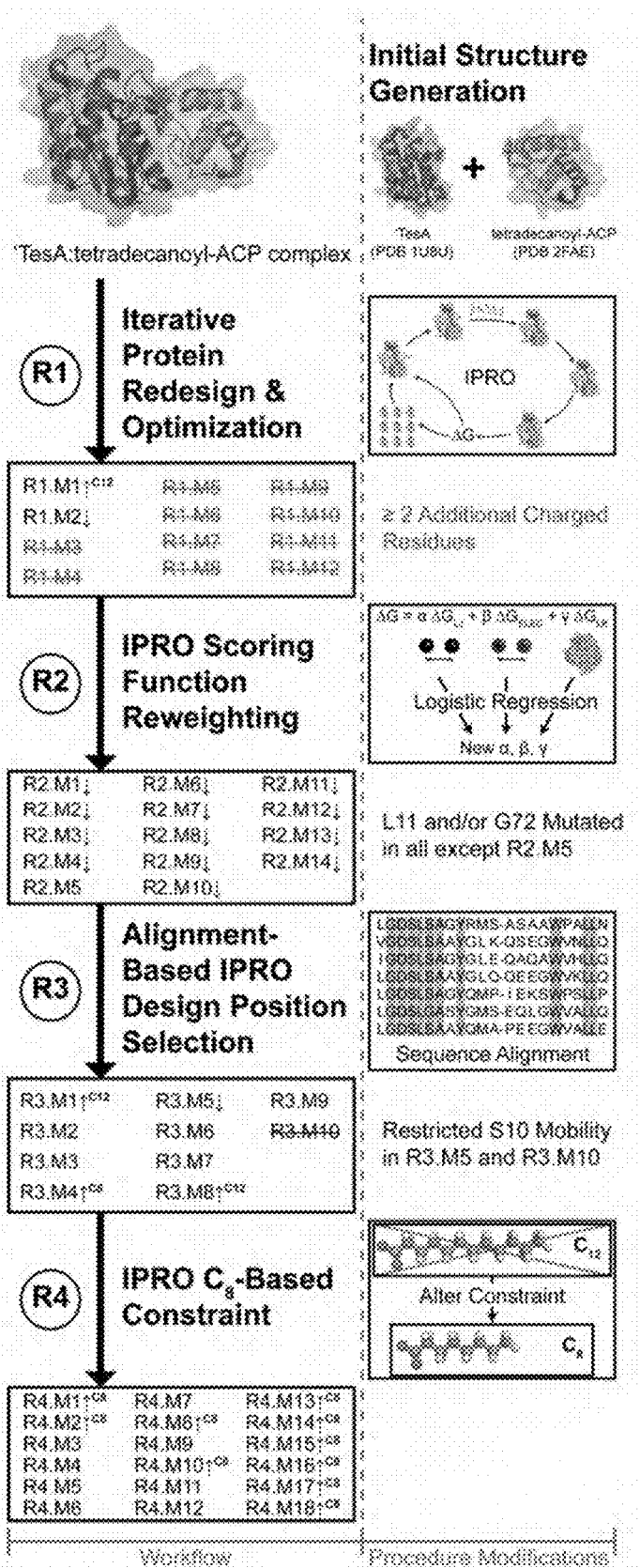
FIG. 1 is an overview of the Predict-Design-Revise approach used to guide 'TesA redesign. This figure illustrates the steps taken (workflow, left column) in efforts to identify mutants with improved specificities towards C12- or C8-FFA production and improve computational design protocols (procedure modifications, right column). Each black box represents experimental testing of the computational mutants, where upward arrows indicate significant improvements in the C12 ($p<0.05$) or C8 ($p<0.005$) composition while maintaining wild-type activity levels.
Figures 2A, 2B:
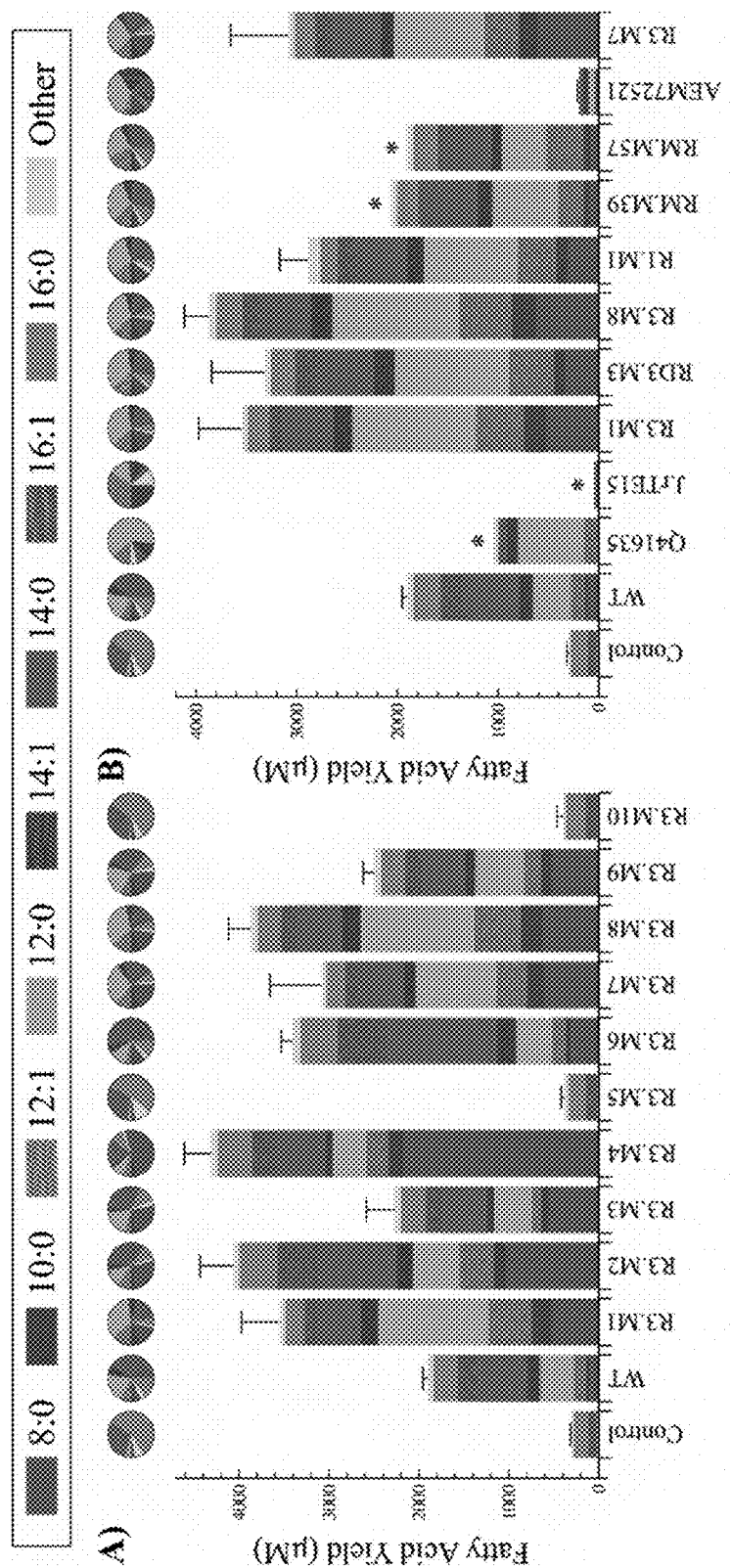
FIGS. 2A, 2B, 2C, and 2D are graphs depicting fatty acid production profiles for computationally-predicted mutants and heterologously expressed acyl-ACP thioesterases. In each of FIGS. 2A through 2D, the FFA yields for various thioesterases are shown as bars, and their molar compositions are depicted as pie charts. The yields and compositions of wild-type 'TesA (WT), uninduced cells (Control), and the ten (10) Round 3 mutants are shown in FIG. 2A. The most C12-specific, most C8-specific, and most active acyl-ACP thioesterases are depicted in FIG. 2B, FIG. 2C, and FIG. 2D, respectively. Control and WT results are also included for reference. These thioesterases include results from the Examples, as well as plant and bacterial acyl-ACP thioesterases expressed in *E. coli*, and variants of these thioesterases (see Examples). Error bars indicate total FFA yield standard deviation for experiments presented in the Examples, and are taken from their corresponding sources for all other thioesterases. An asterisk (*) above a bar indicates that error values were not calculated or provided. FFA production profiles for all thioesterases assayed are presented in Table 1, below.
Figures 2C, 2D:
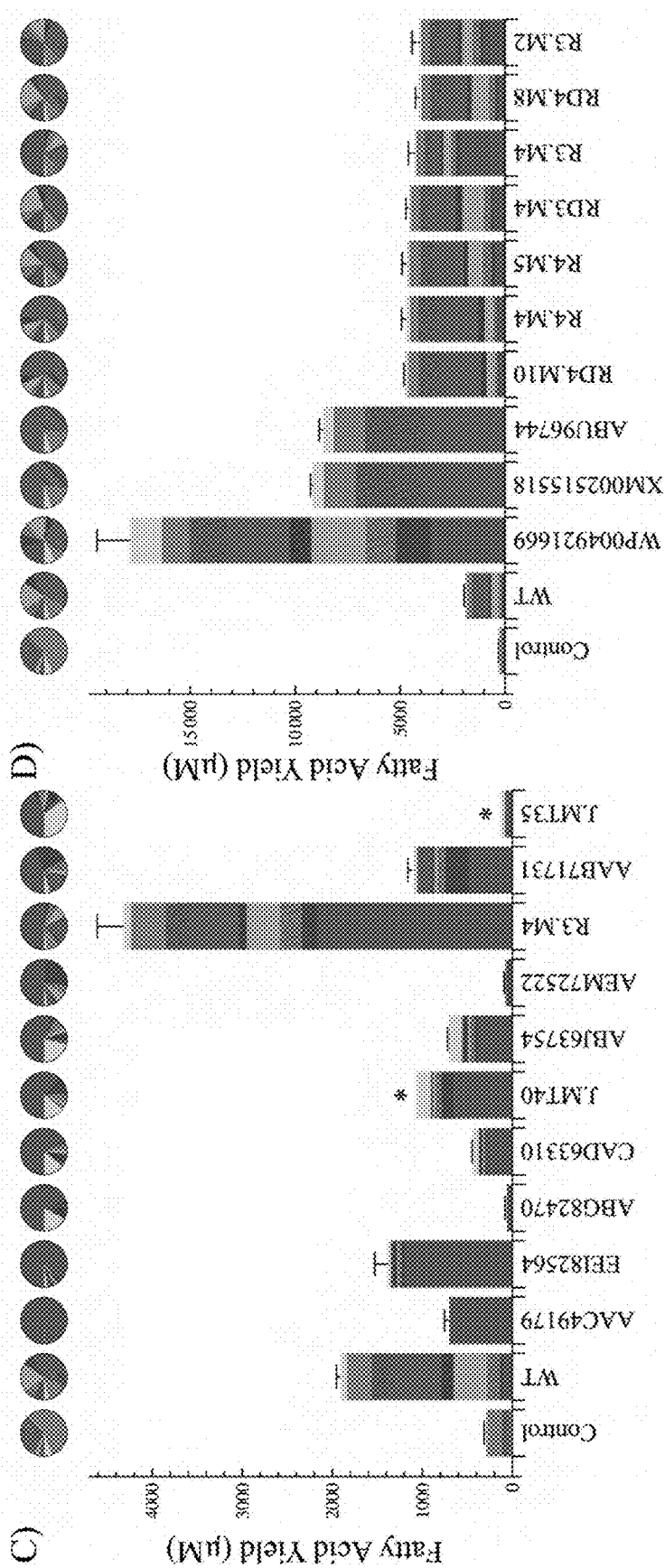
Figure 3A:
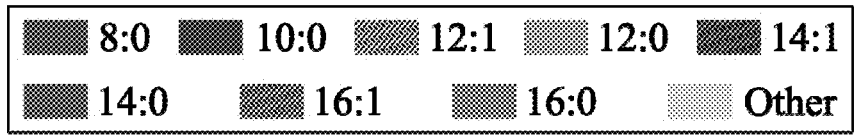
FIGS. 3A and 3B are fatty acid production profiles for the most C12-specific randomly generated 'TesA variants (FIG. 3A) and for the most C8-specific randomly generated 'TesA variants (FIG. 3B). The formatting of FIGS. 3A and 3B is the same as for FIGS. 2A through 2D.
Figure 3A:
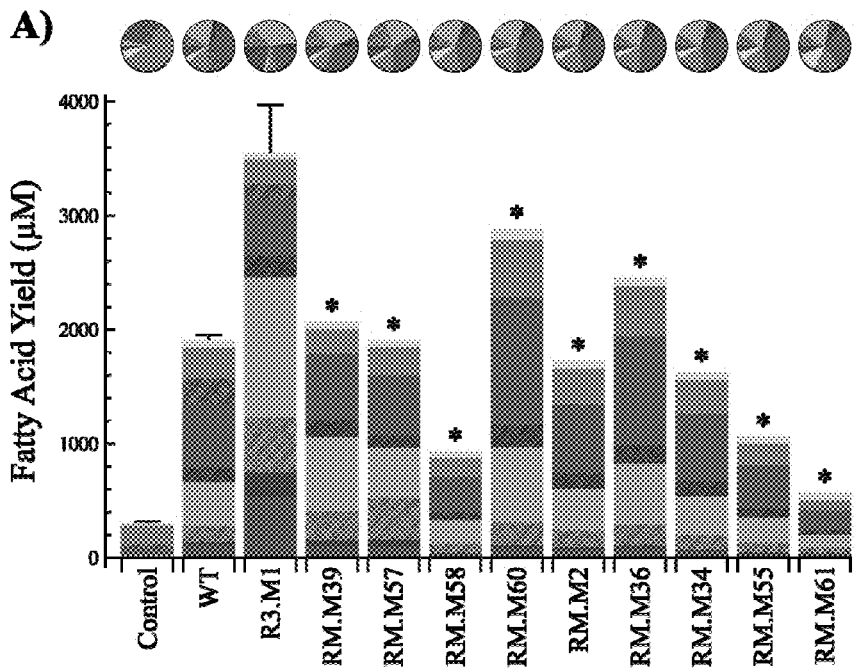
Figure 3B:
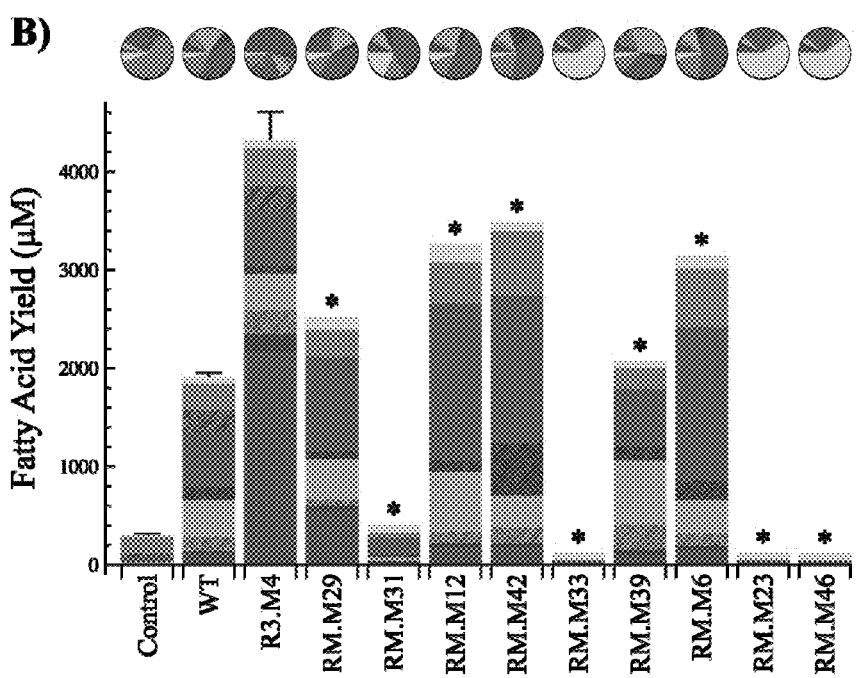
Figure 3C:
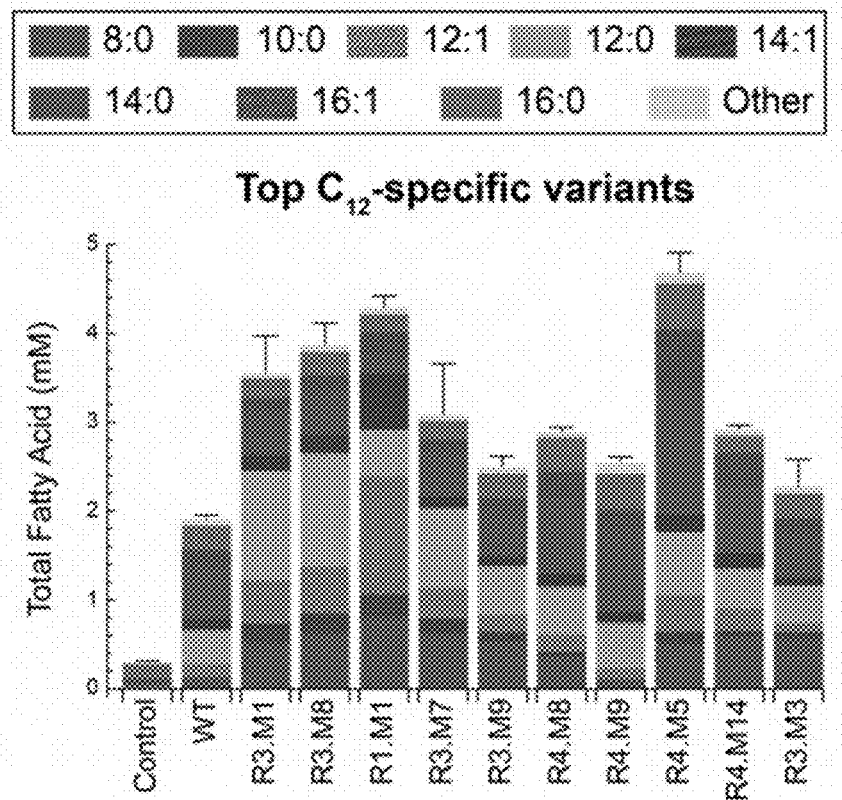
FIGS. 3C and 3D are additional fatty acid production profiles for C12-specific (FIG. 3C) and C8-specific (FIG. 3D) computationally designed variants. FFA titers are shown as bars, where error bars indicate total FFA standard deviation. Profiles of uninduced cells (Control) and wild-type 'TesA (WT) are provided for reference. All profiles are listed in Table 1.
Figure 3D:
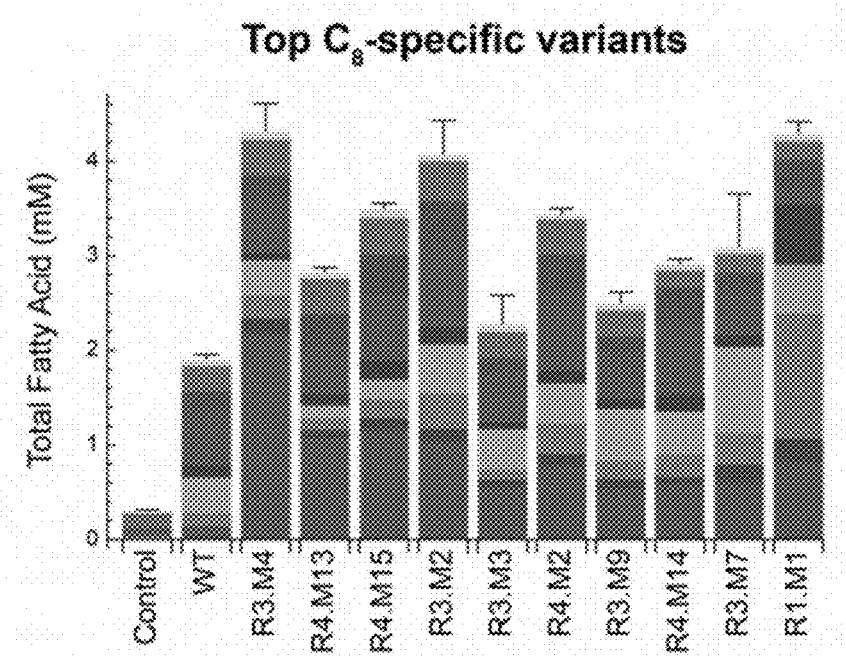

SEQ. ID. NO: 1 (amino acid sequence of mature *E. coli* 'TesA; PDB 1U8U):
1 adtllilgds lsagyrmsas aawpallndk wqsktsvvna sisgdtsqqg larlpallkg 61 hqprwvlvel ggndglrgfq pqqtegtlrq ilqdvkaana epllmgirlp anygrrynea

```
                              SEQUENCE LIST 121  fsaiypklak  efdvpllpff  meevylkpqw  mqddgihpnr  daqpfiadwm  akqlqplvnh 181  dslehhhhhh*

SEQ. ID. NO: 2: (nucleotide coding sequence, E. coli 'TesA gene):
  1  atgatgaact  tcaacaatgt  tttccgctgg  catttgccct  tcctgtttct  ggtcctgtta 61  accttccgtg  ccgccgcagc  ggacacgtta  ttgattctgg  gtgatagcct  gagcgccggg 121  tatcgaatgt  ctgccagcgc  ggcctggcct  gccttgttga  atgataagtg  gcagagtaaa 181  acgtcggtag  tcaatgccag  catcagcggc  gacacctcgc  aacaagggct  ggcgcgcctt 241  ccggctctgc  tgaaacagca  tcagccgcgt  tgggtgctgg  ttgaactggg  cggcaatgac 301  ggtttgcgtg  gttttcagcc  acagcaaacc  gagcaaacgc  tgcgccagat  tttgcaggat 361  gtcaaagccg  ccaacgctga  accattgtta  atgcaaatac  gtctgcctgc  aaactatggt 421  cgccgttata  atgaagcctt  tagcgccatt  taccccaaac  tcgccaaaga  gtttgatgtt 481  ccgctgctgc  ccttttttat  ggaagaggtc  tacctcaagc  cacaatggat  gcaggatgac 541  ggtattcatc  ccaaccgcga  cgcccagccg  tttattgccg  actggatggc  gaagcagttg 601  cagccttttag  taaatcatga  ctcataa
```
*NB: The C-terminal eight (8) residues in SEQ. ID. NO: 1 is an expression tag.

Nucleotides 79 to the end of SEQ. ID. NO: 2 (nt 624) encodes the mature, wild-type 'TesA peptide shown in SEQ. ID. NO: 1.

Abbreviations and Definitions

"Carbon source" refers to a substrate or compound suitable to be used as a source of carbon for prokaryotic or simple eukaryotic cell growth. Carbon sources can be in various forms, including but not limited to polymers, carbohydrates, acids, alcohols, aldehydes, ketones, amino acids, peptides, etc. These include, for example, various monosaccharides such as glucose, oligosaccharides, polysaccharides, cellulosic material, xylose, and arabinose, disaccharides such as sucrose, saturated or unsaturated fatty acids, succinate, lactate, acetate, ethanol, etc., or mixtures thereof. The carbon source can additionally be a product of photosynthesis, including but not limited to glucose.

CHARMM®-brand software refers to a molecular modeling and simulation program designed to model many-particle systems. The program includes a comprehensive set of force fields to simulate biomolecules, such as proteins, nucleic acids, carbohydrates, lipids, their assemblies, and the small molecules that interact with these targets. CHARMM® software runs on a variety of UNIX-compatible computer platforms, and includes an optional graphical output. A free version of CHARMM® is available to academic, government, and non-profit companies at www.charmm.org (Chemistry and Harvard Molecular Mechanics). For-profit companies may purchase the CHARMM® software from Dassault Systèmes BIOVIA (San Diego, Calif., USA; formerly Accelrys, Inc.).

When used with reference to a nucleic acid or protein, "derived" means that the nucleic acid or polypeptide is isolated from a described source or is at least 70%, 80%, 90%, 95%, 99%, or more identical to a nucleic acid or polypeptide included in the described source.

"Endogenous." As used herein with reference to a nucleic acid molecule and a particular host, "endogenous" refers to a nucleic acid sequence or polypeptide that is in the host and was not introduced into the host using recombinant engineering techniques. For example, an endogenous gene is a gene that was present in a host when the host was originally isolated from nature. A gene is still considered endogenous if the control sequences, such as promoter or enhancer sequences that activate transcription or translation, have been altered through recombinant techniques.

"Heterologous." As used herein with reference to a nucleic acid molecule or polypeptide in a particular host, "heterologous" refers to any nucleic acid molecule or polypeptide that does not originate from that particular host as found in nature. Thus, a non-naturally-occurring nucleic acid molecule or protein is considered to be heterologous to a host once introduced into the host. A nucleic acid molecule or protein that is naturally-occurring also can be heterologous to a particular host. For example, an entire coding sequence isolated from cell X is a heterologous nucleic acid with respect to cell Y once that coding sequence is introduced into cell Y, even if X and Y are the same host type.

"Expression" refers to the process by which a gene's coded information is converted into the structures and functions of a host, such as a protein, transfer RNA, or ribosomal RNA. Expressed genes include those that are transcribed into mRNA and then translated into protein and those that are transcribed into RNA but not translated into protein (for example, transfer and ribosomal RNAs).

The term "fatty acid derivatives" refers to products other than fatty acids themselves made in part from the fatty acid biosynthetic pathway of a host. Fatty acid derivatives may be generated after extraction of the fatty acids from the host. Alternatively, hosts can be engineered to produce fatty acid derivatives. Exemplary fatty acid derivatives include, for example, short and long chain alcohols, polyesters, polyhydroxyalkanoates, hydrocarbons such as alkanes, olefins, ketones, and fatty acid esters including waxes.

The term "fatty acid product" refers to any fatty acid or derivative thereof produced by a host prior to extraction therefrom. Examples include but are not limited to fatty acids, fatty alcohols, fatty acid esters, polyesters, polyhydroxyalkanoates, ketones, olefins, waxes, and hydrocarbons. "Fatty acids" include hydroxylated and other forms thereof.

Fermentation broth: Includes any medium which supports host life (i.e., a microorganism that is actively metabolizing carbon). A fermentation medium usually contains a carbon source. The carbon source can be anything that can be used, with or without additional enzymes, by the host for energy.

"FFA"=free fatty acid.

"Gene" as used herein refers to a nucleic acid sequence that includes at least one start codon followed by a coding sequence for at least one polypeptide. For the purposes herein, "gene" may or may not include a stop codon, a promoter, enhancers, or other elements required for its expression. A gene may include introns in addition to exons, particularly if derived from eukaryotic genomic DNA. Genes that include introns are preferably expressed in eukaryotic hosts or other expression systems capable of excising the introns. Genes configured for being expressed in prokaryotic hosts preferably do not include introns.

"Gene product" refers to a protein or polypeptide encoded and expressed by a particular gene.

Disclosed herein are host cells transformed to contain a synthetic gene construct that drives the expression of a mutant thioesterase. "Host" or "host cell" is defined broadly herein and explicitly refers to any organism, without limitation, capable of containing and expressing the synthetic gene constructs disclosed herein. The host may be prokaryotic or eukaryotic, single-celled or multicellular, including mammalian cells, plant cells, fungi, etc. Examples of single-celled hosts include cells of *Escherichia, Salmonella, Bacillus, Clostridium, Streptomyces, Staphyloccus, Neisseria, Lactobacillus, Shigella*, and *Mycoplasma*. Suitable *E. coli* strains (among a great many others) include BL21(DE3), C600, DH5αF', HB101, JM83, JM101, JM103, JM105, JM107, JM109, JM110, MC1061, MC4100, MM294, NM522, NM554, TGI, $\chi$1776, XL1-Blue, and Y1089+, all of which are commercially available. The same host in the present invention can preferably be used for both recombinant DNA cloning and protein expression.

"Introduce." When used with reference to genetic material, such as a nucleic acid, and a host, "introduce" refers to the delivery of the genetic material to the host in a manner such that the genetic material is capable of being expressed and maintained within the host. Introduction of genetic material includes both transformation and transfection. Transformation encompasses techniques by which a nucleic acid molecule can be introduced into hosts such as prokaryotic cells or non-animal eukaryotic cells. Transfection encompasses techniques by which a nucleic acid molecule can be introduced into hosts such as animal cells. These techniques include but are not limited to introduction of a nucleic acid via conjugation, electroporation, lipofection, infection, and particle gun acceleration. See also "transforming," below.

"IPRO" refers to Iterative Protein Redesign and Optimization, both the process itself and a suite of computer programs that implement the process. See Pantazes, Grisewood, Li, Gifford, and Maranas (5 Feb. 2015) "The Iterative Protein Redesign and Optimization (IPRO) suite of programs," *J Comput Chem.* 36(4):251-63 (published online 2 Dec. 2014) and Saraf, Moore, Goodey, Cao, Benkovic, and Maranas (2006), "IPRO: An Iterative Computational Protein Library Redesign and Optimization Procedure," *Biophysical Journal* 90:4167-4180, both of which are incorporated herein by reference. IPRO is a process and a computer program to model putatively effective changes to the amino acid sequence of a protein to improve a desired performance characteristic of the protein. The IPRO algorithms help sharpen protein library design by focusing the library on sequences that optimize computationally accessible proxies. The IPRO suite of programs offers an integrated environment for (1) altering protein binding affinity and specificity; (2) grafting a binding pocket into an existing protein scaffold; (3) predicting the tertiary structure of an antibody based on its sequence; (4) enhancing enzymatic activity; and (5) assessing the structure and binding energetics for a specific mutant. The above-noted papers provide an overview of the methods involved in IPRO, input language terminology, algorithmic details, software implementation specifics and application highlights. IPRO can be downloaded at http://www.maranasgroup.com/submission/ipro2014.htm.

An "isolated" biological component (such as a nucleic acid molecule, polypeptide, or cell) has been substantially separated, purified, concentrated and/or enriched away from other biological components in which the component naturally occurs, such as other chromosomal and extrachromosomal DNA, RNA, and proteins. Nucleic acid molecules and polypeptides that have been "isolated" include nucleic acid molecules and polypeptides purified by standard purification methods. The term also includes nucleic acid molecules and polypeptides prepared by recombinant expression in a host, as well as chemically synthesized nucleic acid molecules and polypeptides. In one example, "isolated" refers to a naturally-occurring nucleic acid molecule that is not immediately contiguous with both of the sequences with which it is immediately contiguous (one on the 5' end and one on the 3' end) in the naturally-occurring genome of the organism from which it is derived.

"Long-chain" fatty acid, fatty acyl-ACP, or fatty acyl-CoA refers to fatty acids, fatty acyl-ACPs, or fatty acyl-CoAs (respectively) having a carbon chain longer than 12 carbons.

"Medium-chain" fatty acid, fatty acyl-ACP, or fatty acyl-CoA refers to fatty acids, fatty acyl-ACPs, or fatty acyl-CoAs (respectively) having a carbon chain of 6 to 12 carbons.

"Short-chain" fatty acid, fatty acyl-ACP, or fatty acyl-CoA refers to fatty acids, fatty acyl-ACPs, or fatty acyl-CoAs (respectively) having a carbon chain fewer than 6 carbons.

"Microorganism" refers to prokaryotic and eukaryotic microbial species from the domains Archaea, Bacteria and Eucarya, the latter including yeast and filamentous fungi, protozoa, algae, or higher Protista. The terms "microbial cells" and "microbes" are used interchangeably with the term microorganism.

The term "nucleic acid" encompasses all forms of RNA and DNA molecules, without limitation, including naturally occurring nucleic acids and synthetic nucleic acid molecules, such as those that are chemically synthesized or recombinantly produced. The nucleic acid can be double-stranded or single-stranded. Where single-stranded, the nucleic acid molecule can be the sense strand, the antisense strand, or both. In addition, the nucleic acid can be circular or linear.

"Operationally linked" generally refers to the association of nucleic acid sequences on a single nucleic acid fragment so that the function of a first sequence is regulated by a second sequence. In the context of a promoter being "operationally linked" to a coding sequence, the promoter is capable of regulating the expression of that coding sequence, i.e., the coding sequence is under the transcriptional control of the promoter. Coding sequences can also be operationally linked to regulatory sequences (such as enhancers) in a sense or antisense orientation. Sequences that are operationally linked are not necessary directly physically linked.

"Promoter" refers to a nucleic acid sequence, normally located upstream of a protein-coding sequence, which contains a binding site for an RNA polymerase.

A "selectable marker" refers to a gene introduced into a cell that confers to the cell a trait suitable for artificial selection. For example, the selectable marker may confer to the transformed cells a phenotypic trait that protects them from a selective agent in their environment, i.e., in the growth media. Examples of selectable markers include, but are not limited to, antibiotic resistance markers (e.g., genes encoding resistance to kanamycin, ampicillin, chloramphenicol, gentamycin, or trimethoprim) and metabolic markers (e.g., amino acid synthesis genes or transfer RNA genes). As is appreciated in the art, the origin of replication can also be used as a selectable marker. In some cases, more than one selectable marker may be employed.

The term "signal peptide" as used herein is synonymous with the terms "signal sequence," "targeting signal," "localization signal," "localization sequence," "transit peptide," "leader sequence," and "leader peptide" and refers to a regulatory peptide present at the N-terminus of an expressed protein that is destined to be secreted from the host.

"Thioesterase" (synonymous with "thioester hydrolase") as used herein means any enzyme falling within Enzyme Classification E.C. 3.1.2.x, and refers to enzymes that catalyze the splitting of a thioester bond. Included within this definition are acyl-acyl carrier protein ("Acyl-ACP") thioesterases. "TesA" refers to thioesterase A enzymes generically; "'TesA" (with a leading apostrophe) refers specifically to a cytosolic thioesterase found in E. coli (and its naturally occurring variants) that lacks an N-terminal signal peptide.

"Thioesterase activity" refers to enzymatic activity to cleave thioester bonds.

"Transforming" refers to any method used to cause the uptake of nucleic acids by living cells. The present disclosure encompasses any method, now known or developed in the future, of introducing nucleic acids into living cells. Suitable methods of transformation include chemical transformation (e.g., calcium chloride-mediated transformation), electroporation, sonication, macroinjection, microinjection, and viral infection. These methods of transformation are conventional and well known in the art. Therefore, they shall not be described in any detail herein. For complete details, see, for example, Michael R. Green and Joseph Sambrook, "Molecular Cloning: A Laboratory Manual, 4$^{th}$ Ed.," © 2012, Cold Spring Harbor Lab Press, ISBN-10: 1936113422.

"Variants" of the sequences described herein include homologs. Homologs can be identified by homologous nucleic acid and polypeptide sequence analyses. Known nucleic acid and polypeptide sequences in one organism can be used to identify homologous polypeptides in another organism. For example, performing a query on a database of nucleic acid or polypeptide sequences can identify homologs thereof. Homologous sequence analysis can involve BLAST or PSI-BLAST analysis of databases using known polypeptide amino acid sequences (see, e.g., Altschul S F, Gish W, Miller W, Myers E W, and Lipman D J (1990) "Basic local alignment search tool." J. Mol. Biol. 215(3): 403-10). Those proteins in the database that have greater than 35% sequence identity are candidates for further evaluation for suitability in the method disclosed herein. If desired, manual inspection of such candidates can be carried out in order to narrow the number of candidates that can be further evaluated. Manual inspection is performed by selecting those candidates that appear to have conserved domains. Determining nucleic acid sequences from discovered homologous amino acid sequences or amino acid sequences from discovered homologous nucleic acid sequences can be deduced using the genetic code.

Variants of the coding sequences described herein include degenerate variant sequences that encode the same polypeptides as disclosed herein. Such degenerate variants can be deduced with the genetic code.

Variants of the sequences described herein also include conservative amino acid substitutions of the sequences described herein. A "conservative substitution" means the replacement of one amino acid by an amino acid having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Variants of the sequences described herein include fragments of the sequences described herein. "Fragment" means a portion of the full-length sequence. For example, a fragment of a given polypeptide is at least one amino acid fewer in length than the full-length polypeptide (e.g. one or more internal or terminal amino acid deletions from either amino or carboxy-termini). Fragments therefore can be any length up to, but not including, the full-length polypeptide. Suitable fragments of the polypeptides described herein include but are not limited to those having 50%, 60%, 70%, 75%, 80%, 85%, 90%, 95%, 96%, 97%, 98%, or more of the length of the full length polypeptide.

Variants of the sequences described herein also include repeating units of the sequences described herein. "Repeating units" means a repetition of a given sequence in tandem. Also included are polypeptides having repeating units of fragments of the sequences described herein.

The variant sequences include sequences with about 50%, 60%, 70%, 75%, 80%, 85%, 90%, 95%, 96%, 97%, 98%, or more identity to the sequences described herein. The term "identity" and grammatical variations thereof, mean that two or more referenced entities are the same. Thus, where two protein sequences are identical, they have the same sequence. The extent of identity between two sequences can be ascertained using any number of computer programs and mathematical algorithms known in the art. Such algorithms that calculate percent sequence identity (homology) generally account for sequence gaps and mismatches over the comparison region. For example, a BLAST (e.g., BLAST 2.0) search algorithm (Altschul et al., supra) has exemplary search parameters as follows: Mismatch 2; gap open 5; gap extension 2. For polypeptide sequence comparisons, a BLASTP algorithm is typically used in combination with a scoring matrix, such as PAM100, PAM 250, and BLOSUM 62.

WT=wild-type.

Suitable variants of the nucleic acid or polypeptide sequences disclosed herein have the same type of activity (without regard to the degree of the activity) as the nucleic acid or polypeptide to which the sequence corresponds. Such activities may be tested according to the assays described herein and according to methods known in the art.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations in both the description and claims shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The gene constructs, mutant proteins, and methods disclosed herein can comprise, consist of, or consist essentially of the essential elements and limitations described herein, as well as any additional or optional ingredients, components, steps or limitations described herein or otherwise useful in expressing mutant proteins in a transformed host cell.

All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

DETAILED DESCRIPTION

Disclosed herein are gene constructs that encode mutant thioesterases enzymes. The gene constructs encode and drive the expression of a mutant thioesterase that has at least one altered property in vitro and/or in vivo as compared to the properties of the precursor thioesterase. Specifically, the mutant thioesterases disclosed herein increase the production of medium-chain fatty acids in hosts transformed to express one or more of the mutant thioesterases as compared to host cells that have not been transformed to express any of the mutant thioesterases.

The mutant thioesterases described herein were derived from a naturally-occurring *E. coli* thioesterase A ('TesA; mature amino acid sequence at SEQ. ID. NO: 1) that was rationally redesigned via computer modeling to bias its binding and catalytic activity toward the production of medium-chain (C8-C14) fatty acids, octanoic acid (trivial name caprylic acid) and its unsaturated isomers to tetradecanoic acid (trivial name myristic acid) and its unsaturated isomers. More specifically, the wild-type 'TesA was computationally redesigned to increase the production of C8 and C12 FFA's in hosts transformed to express gene constructs encoding and expressing the computationally redesigned/ mutated 'TesA proteins. While the exemplary thioesterase described in the Examples was 'TesA from *E. coli*, the naturally-occurring precursor thioesterase can be obtained from any source without limitation, including from plant, animal, bacterial, fungal, yeast, or other microbial sources. The mutant thioesterase can be derived from a precursor thioesterase from *Acidovorax, Acinetobacter, Aeromonas, Alcanivorax, Allivibrio, Alkalilimnicola, Alteromonadales, Alteromonas, Aurantimonas, Azoarcus, Azorhizobium, Azotobacter, Beggiatoa, Beijerinckia, Bordetella, Bradyrhizobium, Burkholderia, Caulobacter, Cellvibrio, Chromobacterium, Citrobacter, Comamonas, Cupriavidus, Dechloromonas, Delftia, Desulfovibrio, Enterobacter, Erwinia, Escherichia, Geobacter, Hahella, Halorhodospira, Herminiimonas, Idiomarina, Janthinobacterium, Klebsiella, Leptospira, Leptothrix, Limnobacter, Magnetospirillum, Marinobacter, Marinomonas, Methylibium, Methylobacillus, Methylobacterium, Methylocella, Methylococcus, Moritella, Nitrobacter, Nitrococcus, Nitrosomonas, Nitrosospira, Oceanospirillum, Oligotropha, Pectobacterium, Photobacterium, Photorhabdus, Polaromonas, Proteus, Providencia, Pseudoalteromonas, Pseudomonas, Psychromonas, Ralstonia, Reinekea, Rhodobacterales, Rhodoferax, Rhodopseudomonas, Rhodospirillum, Saccharophagus, Salmonella, Serratia, Shewanella, Shigella, Stenotrophomonas, Streptococcus, Thauera, Thioalkalivibrio, Thiobacillus, Vibrio, Xanthomonas*, or *Yersinia*.

More specifically, disclosed herein is an unnatural, mutated protein comprising an amino acid sequence that is at least 80% identical to SEQ. ID. NO: 1 and has a substitution at an amino acid position selected from the group consisting of positions I107, R108, L109, S122, M141, E142, Y145, L146, and combinations thereof. The mutated protein has thioesterase activity to catalyze the hydrolysis of a C8, C10, C12, and/or C14 acyl-acyl carrier protein substrate to yield a free fatty acid or a free fatty acid derivative. It is preferred, although not required, that the thioesterase activity of the mutated protein is greater than the activity of the corresponding thioesterase of SEQ. ID. NO: 1.

Also disclosed herein is a gene construct encoding a mutated thioesterase protein as described herein. The gene construct may optionally comprise nucleotide regulatory sequences operationally connected to the nucleotides encoding the mutated protein, wherein the regulatory sequences are dimensioned and configured to drive expression of the protein in a host cell transformed to contain the gene construct. The regulatory sequences are chosen based upon the nature of the host into which the construct is to be transformed.

Also included herein is a host cell transformed to contain and express the gene construct encoding the mutated thioesterase protein. The host cell can be a transformed microbe, a transformed eukaryote, a transformed prokaryote, or a transformed plant cell.

As described in the Examples, the precursor thioesterase is *E. coli* 'TesA. In preferred versions of the protein and method disclosed herein, the precursor thioesterase has at least about 20%, for example, at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% sequence identity to 'TesA. In yet another example, the precursor thioesterase has at least about 20%, for example, at least about 25%, 10%, 35%, 40%, 45%, 50%, 55%, 60%, 65%, 70%, 75%, 80%, 85%, 90%, 91%, 92%, 93%, 94%, 95%, 96%, 97%, 98%, or 99% sequence identity to a 'TesA that is obtained from an *E. coli*. The analogous sequence can be from a naturally-occurring protein or can be from a previously modified protein.

As noted above, the method disclosed herein can be implemented using any host capable of expressing the gene construct. Examples of suitable bacterial hosts include gram-positive bacteria such as strains of *Bacillus*, (e.g., *B. brevis* or *B. subtilis*), *Pseudomonas*, and *Streptomyces*, as well as gram-negative bacteria, such as strains of *E. coli*. Particularly desirable hosts for expression in this regard include bacteria that do not produce lipopolysaccharide and are, therefore, endotoxin free. The introduction of a vector into a bacterial host may, for instance, be performed by protoplast transformation (Chang and Cohen (1979) *Molecular General Genetics*, 168:111-115), using competent cells (Young and Spizizen (1961) *Journal of Bacteriology*, 81:823-829; Dubnau and Davidoff-Abelson (1971) *Journal of Molecular Biology*, 56: 209-221), electroporation (Shigekawa and Dower (1988) *Biotechniques*, 6:742-751), or conjugation (Koehler and Thorne (1987) *Journal of Bacteriology*, 169:5771-52783. Commercially available vectors for expressing heterologous proteins in bacterial hosts include but are not limited to pZERO, pTrc99A, pUC19, pUC18, pKK223-3, pEX1, pCAL, pET, pSPUTK, pTrxFus, pFastBac, pThioHis, pTrcHis, pTrcHis2, and pLEx. For example, the phage in lambda GEM™-11 may be utilized in making recombinant phage vectors which can be used to transform hosts, such as *E. coli* LE392.

Examples of suitable yeast hosts include strains of *Saccharomyces*, such as *S. cerevisiae*; *Schizosaccharomyces*; *Kluyveromyces*; *Pichia*, such as *P. pastoris* or *P. methlanolica*; *Hansenula*, such as *H. Polymorpha*; *Yarrowia*; or *Candida*. Methods for transforming yeast cell with heterologous DNA and producing heterologous polypeptides therefrom are disclosed by Clontech Laboratories, Inc., Palo Alto, Calif., USA (in the product protocol for the "YEAST-MAKER"-brand yeast transformation system kit); Reeves et al. (1992) *FEMS Microbiology Letters* 99:193-198; Manivasakam and Schiestl (1993) *Nucleic Acids Research* 21 (18): 4414-5; and Ganeva et al. (1994) *FEMS Microbiology Letters* 121:159-64. See also "Molecular Cloning: A Laboratory Manual, 4$^{th}$ Ed.," supra. Expression and transformation vectors for transformation into many yeast strains are described in the literature and commercially available. For example, expression vectors have been developed for the following yeasts: *Candida albicans* (Kurtz, et al. (1986) *Mol. Cell. Biol.* 6:142); *Candida maltosa* (Kunze et al. (1985) *Basic Microbiol.* 25:141); *Hansenula polymorpha* (Gleeson et al. (1986) *Gen. Microbiol.* 132:3459) and Roggenkamp et al. (1986) *Mol. Gen. Genet.* 202:302); *Kluyveromyces fragilis* (Das et al. (1984) *J. Bacteriol.* 158:1165); *Kluyveromyces lactis* (De Louvencourt et al. (1983) *J. Bacteriol.* 154:737) and Van den Berg et al. (1990) *Bio/Technology* 8:135); *Pichia quillerimondii* (Kunze et al. (1985) *J. Basic Microbiol.* 25:141); *Pichia pastoris* (Cregg et al. (1985) *Mol. Cell. Biol.* 5:3376; U.S. Pat. Nos. 4,837, 148; and 4,929,555); *Saccharomyces cerevisiae* (Hinnen et al. (1978) *Proc. Natl. Acad. Sci.* USA 75:1929 and Ito et al. (1983) *J. Bacteriol.* 153:163); *Schizosaccharomyces pombe* (Beach et al. (1981) *Nature* 300:706); and *Yarrowia lipolytica* (Davidow et al. (1985) *Curr. Genet.* 10:380-471 and Gaillardin et al. (1985) *Curr. Genet.* 10:49).

Examples of suitable filamentous fungal hosts include strains of *Aspergillus*, e.g., *A. oryzae*, *A. niger*, or *A. nidulans*; *Fusarium* or *Trichoderma*. Fungal cells may be transformed by a process involving protoplast formation, transformation of the protoplasts, and regeneration of the cell wall in a manner known per se. Suitable procedures for transformation of *Aspergillus* hosts are described in EP 238 023 and U.S. Pat. No. 5,679,543. Suitable methods for transforming *Fusarium* species are described by Malardier et al., *Gene*, 1989, 78:147-56 and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al. (1983) *Journal of Bacteriology*, 153: 163; and Hinnen et al. (1978) *PNAS* USA, 75:1920.

Examples of suitable insect hosts include a *Lepidoptora* cell line, such as *Spodoptera frugiperda* (Sf9 or Sf21) or *Trichoplusioa ni* cells ("HIGH FIVE"-brand insect cells, Invitrogen, Carlsbad, Calif.) (U.S. Pat. No. 5,077,214). Transformation of insect cells and production of heterologous polypeptides therein may be performed as described by Invitrogen.

Examples of suitable mammalian hosts include Chinese hamster ovary (CHO) cell lines, e.g., CHO-K1 (ATCC CCL-61); green monkey cell lines, e.g., COS-1 (ATCC CRL-1650) and COS-7 (ATCC CRL-1651); mouse cells, e.g., NS/O; baby hamster kidney (BHK) cell lines, e.g., ATCC CRL-1632 or ATCC CCL-10; and human cells, e.g., HEK 293 (ATCC CRL-1573). Additional suitable cell lines are known in the art and available from public depositories such as the American Type Culture Collection (ATCC), Manassas, Va., USA.

Any of a number of plant cells are also suitable host cells, including (without limitation) algae, tree species, ornamental species, temperate fruit species, tropical fruit species, vegetable species, legume species, monocots, dicots, or in any plant of commercial or agricultural significance. Particular examples of suitable plant hosts include, but are not limited to conifers, petunia, tomato, potato, tobacco, *arabidopsis*, lettuce, sunflower, oilseed rape, flax, cotton, sugarbeet, celery, soybean, alfalfa, medicago, lotus, vigna, cucumber, carrot, eggplant, cauliflower, horseradish, morning glory, poplar, walnut, apple, asparagus, rice, maize, millet, onion, barley, orchard grass, oat, rye, and wheat. Such cells are available from a wide range of sources including: the American Type Culture Collection or from any of a number seed companies, for example, W. Atlee Burpee Seed Co. (Warminster, Pa.), Park Seed Co. (Greenwood, S.C.), Johnny Seed Co. (Albion, Me.), or Northrup King Seeds (Harstville, S.C.).

The copy number of an exogenous nucleic acid expressing a thioesterase in a host impacts cell viability, cell growth, vector stability in the host, and/or fatty acid product production. Accordingly, in various versions of the method, the host includes no more than about 500, about 250, about 150, about 100, about 75, about 50, about 30, or about 25 copies of a nucleic acid encoding a mutant thioesterase. Alternatively or in addition, the host in various versions of the invention includes no less than about 2, about 3, about 4, about 5, about 7, about 10, or about 15 copies of a nucleic acid encoding the mutant thioesterase. Preferred versions include from about 2 to about 250, more preferably of from about 3 to about 150, more preferably of from about 5 to about 100, and most preferably of from about 5 to about 30 copies of a nucleic acid encoding a mutant thioesterase. Included herein are single-copy versions of the transformed host.

In some specific versions, the host includes no more than about 100, about 90, about 75, about 50, about 25, about 10, about 7, or about 5 copies of a nucleic acid encoding a thioesterase in the exponential phase of growth. Alternatively or in addition, the host in various versions of the method includes no less than about 3, about 4, or about 5 copies of a nucleic acid encoding a thioesterase in the exponential phase of growth. Preferred versions include from about 3 to about 30 or from about 5 to about 25 copies of a nucleic acid encoding the mutant thioesterase in the exponential phase of growth.

In some specific versions, the host includes no more than about 500, about 250, about 150, about 100, about 75, about 50, about 30, or about 20 copies of a nucleic acid encoding the mutant thioesterase in the stationary phase of growth. Alternatively or in addition, the host in various versions includes no less than about 2, about 3, about 4, about 5, about 7, or about 10 copies of a nucleic acid encoding the thioesterase in the stationary phase of growth. Preferred versions include from about 2 to about 250, more preferably from about 10 to about 150, more preferably from about 10 to about 100, more preferably from about 10 to about 30 copies, and most preferably about 20 copies of a nucleic acid encoding the thioesterase.

The nucleic acid copy numbers described above may be used in conjunction with the $P_{BAD}$ promoter system induced at maximal levels or a promoter system having similar strength or different strength. Stronger promoters, such as Ptrc may be used. Promoters having a similar strength to $P_{BAD}$ include the Ptet promoter, the prpBCDE promoter (PprpB), weak sigma70 promoters, and several promoters derived from engineered libraries (see Alper et al. (2005) *PNAS* 102. (36):12678-83). Higher nucleic acid copy numbers and/or stronger promoters may also be used, preferably in inducible or repressible promoter systems wherein the nucleic acid is expressed with a sub-saturating amount of effector. For an inducible promoter system, the nucleic acid is preferably expressed with an amount of an inducing effector from about 0.25% to about 10%, from about 0.5% to about 10%, from about 1% to about 10%, from about 2.5% to about 10%, or about 5% of the minimal saturating amount. For a repressible promoter system, the nucleic acid is preferably expressed with an amount of a repressible effector of from about 90% to about 99.75%, from about 90% to about 99.5%, from about 90% to about 99%, from about 90% to about 97.5%, or about 95% of the minimal saturating amount. With such sub-saturating amounts of effector, the host may include about 50 or more copies of a nucleic acid encoding the mutant thioesterase, such as about 100 or more copies, about 150 or more copies, about 200 or more copies, about 250 or more copies, about 300 or more copies or about 500 or more copies.

The copy number of the nucleic acid or the vector comprising the nucleic acid in the host is a function, in part, of the origin of replication on the vector. Suitable origins of replication for use in the present invention include but are not limited to those derived from pBR322 or its derivatives (such as pTrc99) (colE1 origin), pACYC or its derivatives (p15A origin), pBBR1 or its derivatives (pBBR1 origin), pSC101 or its derivatives (see Sugiura et al. (1993) *J. Bacteriol.* 175(18):5993-6001), R1 plasmid or its derivatives, P1 plasmid or its derivatives, F plasmid or its derivatives (such as a mini-F plasmid), R6K plasmid or its derivatives, or RK2 plasmid or its derivatives. Preferred origins of replication include those derived from pACYC or its derivatives (p15A origin) or pBBR1 or its derivatives (pBBR1 origin). Methods for generating a vector with origins of replication derived from the above-mentioned sources as well as the copy numbers associated with each origin of replication are provided in the examples that follow.

The host may be growth-competent. "Growth-competent" refers to the property of maintaining growth in culture with respect to a control. For example, a host comprising a nucleic acid expressing an enzyme is growth competent if it is capable of proliferating at a rate equal to a host comprising a nucleic acid expressing a non-functional version of the enzyme. In preferred versions of the method, the host is growth-competent at 37° C.

The host may also be recombinantly stable. "Recombinantly stable" refers to the ability to retain an exogenous nucleic acid or vector comprising the nucleic acid over several generations in culture. The property of being recombinantly stable is typically a function of temperature, copy number of the nucleic acid in the host, the level of expression of the nucleic acid in the host, and/or the effect of the product expressed from the nucleic acid on the host. In preferred versions of the invention, the host is recombinantly stable at 37° C.

Computational enzyme designs efforts that undergo experimental validation are often shown to be underperforming or completely inactive. Rather than learning from failed results, these shortcomings usually cease the use of in silico tools to guide protein engineering. Rather than arriving at this impasse, negative outcomes can guide progress in computational enzyme design procedures and symbiotically lead to industrially competitive variants. This predict-design-revise approach underpins the workflow used in 'TesA redesigns for medium-chain FFAs. See FIG. 1.

The first round (R1) of computations was aimed at improving $C_{12}/C_{14}$ specificity. This first round of computer modeling resulted in only limited successes. Of the twelve tested designs, only one variant (R1.M1, see Tables 1 and 2, below) was active and improved $C_{12}/C_{14}$. Upon further investigation of the tested sequences, 47 out of 55 point mutations were to acidic or basic amino acids. R1.M1 and R1.M2 were the only R1 mutants with less than two acidic or basic point mutations. The IPRO scoring function was hypothesized to be the source of the charged residue predisposition. The scoring function energy terms were reweighted using simple logistic regression on a dataset of high-quality protein structures. The updated scoring function roughly doubled native rotamer recovery relative to the existing scoring function (see the Examples and Tables 1 and 2).

Using the modified IPRO scoring function, the second round (R2) of computations eradicated the bias towards charged residues (0 of 61 point mutations). However, of the fourteen tested R2 variants only R2.M5 was active and it did not meet the design objective. Additional data analysis revealed that either L11 or G72 (see SEQ. ID. NO: 1) were mutated in all R2 variants, except for R2.M5. Mutagenesis at these positions was thought to be detrimental to the catalytic machinery and prompted a systematic approach for selecting design positions using family sequence alignments. This design position selection methodology would have filtered out L11 and G72 as design positions because they showed 85% and 59% sequence conservation respectively (data not shown).

The new set of design positions and updated scoring function were then combined in the third round (R3) of results, which exhibited pronounced increase in the production of medium-chain free fatty acids in the transformed hosts. See the Examples.

Computation-Guided Design Outperforms Random Mutagenesis:

Several of the best performing variants have a small number of mutations that may have been recovered from classical random mutagenesis approaches. Therefore, we created a small library of randomly mutated 'TesA variants by error-prone PCR mutagenesis and screened for changes in product profile. The purpose of this library was to provide a negative control for testing that a library not directed by IPRO would not achieve the same level of success. The FFA profile of 61 E. coli cultures harboring expression vectors for unique 'TesA variants was measured (N=1). Of the 61 random mutants (RMs) screened, 46 were active (i.e., ≥240 µM), and 20 maintained WT FFA production levels (i.e., ≥1750 µM).

The best dodecanoic acid producing RM (RM.M39, 44%±6%) demonstrated a comparable C12 composition to the top computationally predicted variant (R3.M1, 48%±8%) but at the expense of a substantial reduction in total FFA titer (p<0.05, 80% of R3.M1). The best octanoic acid producing RM (RM.M29, 21.9%) produced a lower fraction of C8 than R3.M4 (50%±3%, a 44% reduction) and displayed only 58% of the total activity of R3.M4 (see Table 3, below). A comparison of these results shows that IPRO-guided mutagenesis generated more hits, more active mutants, and better leads than a library of similar size made through random mutagenesis.

Analysis of Successful 'TesA Redesigns:

The best C12-producing variants were dominated by three mutations: S122K, Y145K, and L146K. Mutation S122K (R3.RD3, Table 1) alone was sufficient to shift the C12 fraction to 35% of total FFAs, equal to the best C12-producing mutant R3.M1. A nonpolar mutation at the same position (S122L, R3.RD4) had a similar but less pronounced shift toward C12 at the expense of C14, indicating that S122 is an important residue in the active site. The additional mutations in R3.M1 (Y145K and L146K←equivalent to the R3.M7 mutation) also reduced the long-chain composition but produced a higher fraction of C8 and lowered total activity. Almost all of the top C8-producing variants contained a mutation at Y145 with lysine or phenylalanine as the dominant substituents. The best C8-producing mutant (R3.M4) contained Y145K and L146K mutations, as well as a M141L, which, by itself (R3.M2), was able to dramatically increase the C8 composition. The Y145K mutation drastically increased the fraction of unsaturated products in the C12 and C14 chain lengths.

Figure 4A:
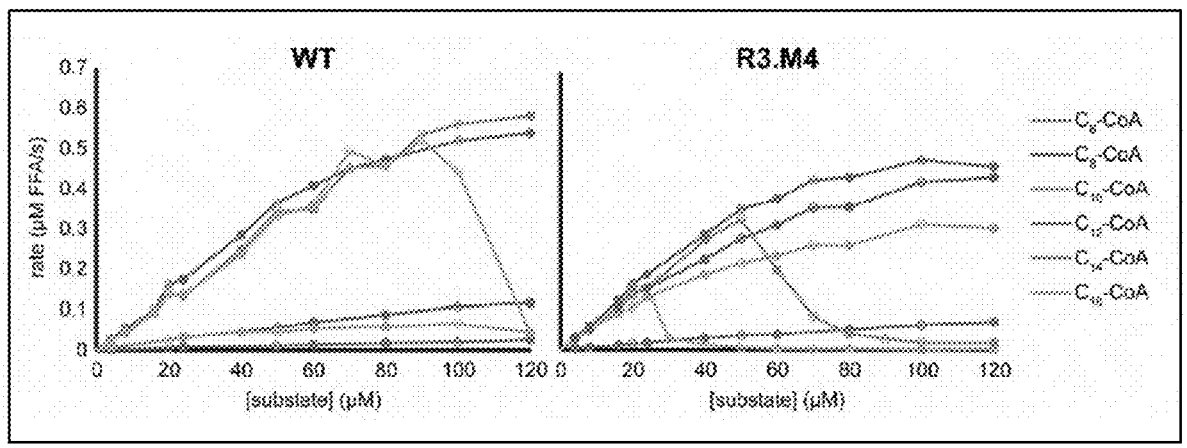
FIGS. 4A, 4B, 4C, 4D, and 4E are enzymatic assays of (FIG. 4A) WT 'TesA and R3.M4 confirm the mutant's increase in specificity for C8 species, and competitive activity assays (FIG. 4B to FIG. 4E) show WT 'TesA and R3.M4 activity on C8-CoA, as a function of (FIG. 4B and FIG. 4C) C14-CoA concentration and (FIG. 4D and FIG. 4E) C16-CoA concentration.
Figure 4B:
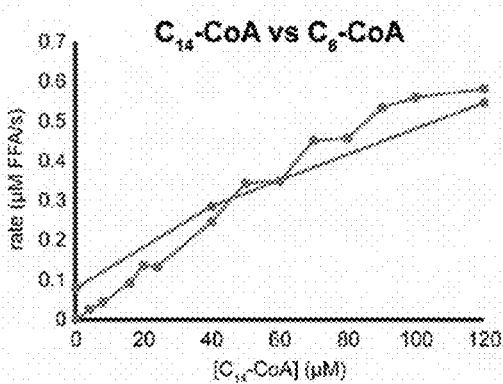
Figure 4C:
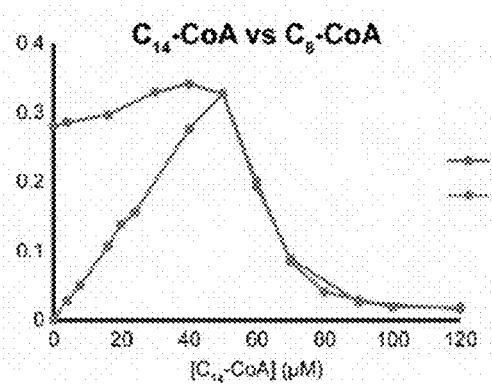
Figure 4D:
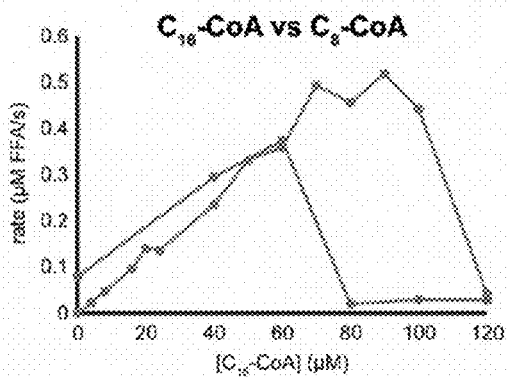
Figure 4E:
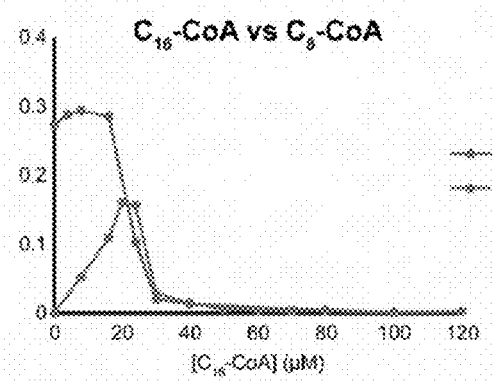

In Vitro Assays of WT 'TesA and C8 Specific R3.M4 Confirm In Vivo Results:

'TesA can catalyze hydrolysis of both acyl-CoA and acyl-ACP substrates. Given the relative availability of these substrates, we compared the kinetic activity of WT 'TesA and R3.M4 on acyl-CoAs ranging from 6 to 16 carbons in length. We monitored reaction progress by tracking the abundance of free CoA released by hydrolysis. The highest in vitro WT activity (FIG. 4) was observed for C12-CoA, C14-CoA, and C16-CoA, consistent with the in vivo data for the release of FFAs from acyl-ACPs (see FIGS. 3A, 3B, 3C, and 3D). In contrast, R3.M4 showed a significant increase in activity on C8-CoA compared to WT, which is consistent with the observed in vivo production of octanoic acid, and a modest decrease in activity on C12-CoA and C14-CoA activity. For both enzymes, we observed an unexpected decrease in activity on hexadecanoyl-CoA (C16-CoA) beyond a threshold concentration. Interestingly, in the R3.M4 mutant, the inhibitory effect of C16-CoA is exacerbated and C14-CoA also shows inhibition (not seen on WT 'TesA). Given the linear reaction progress curves that we observed, we suspected that the enzymes were substrate-inhibited. Therefore, performed assays with both C8-CoA and the CoA species (see FIGS. 4B, 4C, 4D, and 4E). Competitive activity assays were performed at a constant concentration of C8-CoA (50 µM) and variable concentrations of C14-CoA (FIG. 4B for WT and FIG. 4C for R3.M4) and C16-CoA (FIG. 4D for WT and FIG. 4E for R3.M4). In all cases, production of free CoA was inhibited by C14-CoA and C16-CoA in a concentration-dependent manner consistent with the original assay in FIG. 4A.

EXAMPLES

The following Examples are included to provide a more complete disclosure of the gene constructs, mutant thioesterases and transformed hosts described and claimed herein. The Examples do not limit the scope of the claims.

'TesA Model Construction:

The 3-dimensional, X-ray crystal structure of 'TesA was taken from PDB 1U8U (Protein Data Bank, http://www.rcsb.org), where it is in complex with caprylic acid. (Lo, Lin, Shaw, and Liaw, (2005) "Substrate specificities of *Escherichia coli* thioesterase I/protease I/lysophospholipase L1 are governed by its switch loop movement," *Biochemistry* 44:1971-1979.) The acyl ACP structures were adapted from PDB 2FAE, where capryl-ACP is held in an internal binding cavity. (Roujeinikova A, et al. (2007) "Structural studies of fatty acyl-(acyl carrier protein) thioesters reveal a hydrophobic binding cavity that can expand to fit longer substrates," *J Mol Biol* 365(1):135-145.) In order to dock capryl-ACP with 'TesA, the acyl chain was systematically rotated about the phosphopantetheine linker and superimposed with the bound caprylic acid in 1U8U. The rotation that led to the lowest root-mean-square deviation was energy-minimized within CHARMM34. (Brooks B R, et al. (2009) "CHARMM: the biomolecular simulation program," *J Comput Chem* 30(10):1545-1614.)

Acyl-ACPs with different chain lengths were adapted from this initial complex by either deleting atoms or adding atoms using CHARMM's internal coordinate system. Lazaridis-Karplus solvation files, and CHARMM topology and parameter files were constructed using existing parameters from homologous molecules. The constructed topology and parameter files were in close agreement with CGenFF-derived parameters. (See https://cgenff.paramchem.org/ and Vanommeslaeghe & MacKerell (2012) "Automation of the CHARMM General Force Field (CGenFF) I: Bond Perception and Atom Typing," *J Chem Inf Model* 52(12):3144-3154 and Vanommeslaeghe, Raman, & MacKerell (2012) "Automation of the CHARMM General Force Field (CGenFF) II: Assignment of Bonded Parameters and Partial Atomic Charges," *J Chem Inf Model* 52(12):3155-3168.)

Structure-Based Redesign and Analysis:

All computationally-predicted mutants were identified using multiple IPRO trajectories that each ran for 1000 iterations without ensemble structure refinements. (Pantazes, Grisewood, Li, Gifford, and Maranas (5 Feb. 2015) "The Iterative Protein Redesign and Optimization (IPRO) suite of programs," *J Comput Chem.* 36(4):251-63.) The primary objective of each trajectory was to eliminate binding to a larger FFA ($C_{14}$ for Rounds 1-3, $C_{12}$ for Round 4) with a secondary objective to improve binding to the shorter FFA ($C_{12}$ for Rounds 1-3, $C_8$ for Round 4). Design positions for Rounds 1 (L11, G72, L76, I107, R108, A111, F139, and Y145) and 2 (L11, G72, F139, M141, E142, Y145, G155, and I156) were selected based on wild-type proximity to the terminal end of the FFA and catalytic insignificance. Design positions for Rounds 3 and 4 (I107, R108, L109, S122, M141, E142, Y145, L146) were chosen using sequence alignments (see "Sequence Alignment" subsection).

Restraints were imposed to ensure that the intermolecular catalytic distances (±0.2 Å) were maintained (i.e., S10, G44, N73, and H157). All other IPRO parameters were set to their standard values, and calculations were run on the Lion-XF computer system at Penn State University. Error propagation was performed manually and replicated using the Python uncertainties module. (Lebigot EO (2014) "Uncertainties: a Python package for calculations with uncertainties," published online at https://pythonhosted.org/uncertainties/_downloads/uncertaintiesPythonPackage.pdf.) Statistical differences were calculated using Welch's t-test between the wild-type and mutant FFA profiles. For a given enzyme-FFA complex, the interaction energy is found using $IE = G_{Enz\text{-}FFA,min} - G_{Enz} - G_{FFA}$. Mutants were sorted by the interaction energy difference between the short-chain FFA and $C_{14}$ ($\Delta IE = IE_{C12,C8} - IE_{C14,C12}$). Therefore, for a given round, Mutant 1 (smallest $\Delta IE$) would be expected to show the biggest change in specificity.

DNA Synthesis and Strain Construction:

All mutants were created starting with the wild-type 'tesA gene cloned into a pBAD18 plasmid, ATCC 87397. Round 1 mutants were constructed using the QuickChange II site directed mutagenesis kit following the manufacturer's protocol (Agilent Technologies, Santa Clara, Calif., USA). For Rounds 2-4, all mutants were constructed using "GIBSON ASSEMBLY"® strategies (Synthetic Genomics, Inc. La Jolla, Calif., USA). All cloning was performed on *E. coli* DH5α strain (ATCC 67877; U.S. Pat. No. 5,614,620).

Growth Conditions:

For FFA production experiments, the plasmids were transformed into RL08ara cells (K12 MG1655 ΔaraBAD ΔaraFGH Φ(ΔaraEp $P_{CP18}$-araE) ΔfadD). (Khlebnikov, Datsenko, Skaug, Wanner, and Keasling (2001) "Homogeneous expression of the PBAD promoter in *Escherichia coli* by constitutive expression of the low-affinity high-capacity AraE transporter," *Microbiology* 147:3241-3247.) Three single colonies of each mutant were grown overnight on LB media containing 100 μg/mL of ampicillin. Overnight cultures of mutants were diluted 1:100 into 25 mL of LB media containing 100 μg/mL of ampicillin and 0.4% w/v glycerol in a 250 mL baffled shake flask and grown at 37° C. and 250 rpm. When the $OD_{600}$ reached 0.2-0.3, cultures where induced with 0.2% w/v L-arabinose and shaken for 24 h. All mutants were tested in triplicate and error bars represent the standard error of the measurements.

Lipid Extraction:

After twenty-four hours (24 h) post-induction, 2.5 mL culture samples were collected in 10 mL glass centrifuge tubes, and 5 μL of 10 mg/mL heptadecanoic acid in ethanol solution was added as an internal standard. For fatty acid extraction into a chloroform layer, 100 mL of glacial acetic acid was added, followed by 5 mL of a 1:1 v/v solution of chloroform and methanol. Samples were vortexed and centrifuged for 10 min at 1000 g to separate the layers. The water layer and cell debris were aspirated with vacuum so that the only remaining layer was chloroform. The chloroform layer was dried using a SpeedVac SC250EXP concentrator without added heat for 75 minutes and 1.0 torr. Samples were further dried for 30 min in a lyophilizer to remove any residual liquid. To methylate the dried extract, 0.5 mL of 1.25 M HCl in methanol was added and left overnight at 50° C. Finally, 5 mL of a 100 mg/mL sodium bicarbonate solution was added and fatty acid methyl esters were then extracted twice with 0.5 mL hexane for gas chromatography-flame ionization detection (GC-FID) quantification.

Lipid Quantification:

Samples were collected and analyzed using a GC-FID model Shimadzu GC-2010 equipped with an AOC-20i auto-injector, a flame ionization detector, and a 30 meter, 0.25 mm ID RTX-5 column. The program for the oven was 100° C. for 2.0 min, ramp of 80° C./min to 150° C. and hold for 4.0 min, ramp of 4.0° C./min to 218° C. with no hold, and ramp of 80° C./min to 250° C. and hold for 2.5 min.

Scoring Function Reweighting:

A dataset of native and non-native rotamers was collected from the top8000 database. (Richardson, Keedy, and Richardson (2013) "'The Plot' Thickens: More Data, More Dimensions, More Uses, Biomolecular Forms and Functions," in "A Celebration of 50 Years of the Ramachandran Map" © 2013, World Scientific Publishing Co. Pte. Ltd., Singapore. at pp 46-61) Fifty (50) structures were randomly selected for use within the training set. Eighty (80) separate structures were rand on chosen to validate the results. From these 130 structures, the native rotamer was found by finding the rotamer (of the same amino acid type) with the lowest root-mean-square deviation to the crystallized side chain. The van der Waals, electrostatic, and Lazaridis-Karplus solvation energies were calculated for each rotamer regardless of amino acid type. The data was separated for residues at the protein surface and within the core of the protein using the distance-based metric developed by Kuhlman and Baker. (Kuhlman & Baker (2000) "Native protein sequences are close to optimal for their structures," *PNAS* 97(19):10383-10388.) As the number of non-native rotamers heavily outweighed the number of native rotamers, non-native rotamer decoys were randomly removed until there was approximately a 60:40 split of non-native:native rotamers. Using this dataset, symmetric logistic regression was used to determine the optimal set of scoring function weights. (Hall M, et al. (2009) "The WEKA data mining software: an update," *SIGKDD Explor. Newsl.* 11(1):10-18.)

Sequence Alignment:

Using the conserved domain database, 81 members (including 'TesA) of the lysophospholipase L1-like subgroup from the SGNH-hydrolase superfamily were found. (Marchler-Bauer A, et al. (2015) "Cdd: NCBI's Conserved Domain Database," *Nucleic Acids Res* 43(D1):D222-D226.) Among these 81 aligned sequences, positions that exhibited ≥40% sequence conservation or aligned to sequence gaps were filtered out. From this consolidated list, the eight closest residues in wild-type 'TesA to the terminal carbon of lauric acid were selected as design positions.

Random Mutagenesis:

Wild-type 'TesA in pBad18 was randomly mutagenized using Gene Morph II random mutagenesis kit (Agilent Technologies, Santa Clara, Calif., USA) following the manufacturer's instructions to make a library of 61 mutants with a mutation rate of 1.8 amino acids per gene (Table 2). Primers were designed to include the start and stop codons to ensure keeping those positions of the mutants invariant.

Molecular Dynamics:

VMD was used to solvate enzyme-FFA complexes within a 12.0 Å water box with 0.17 M NaCl and contained ≈49,000 atoms (Humphrey W, et al. (1996) "VMD: visual molecular dynamics," *J Mol Graphics*. 14(1):27-38.) Each complex was minimized and slowly heated to 310 K and 1 atm over 7 ns using Langevin dynamics. Force field parameters were identical to those used for the IPRO trajectories. Periodic boundary conditions were applied, and long-range electrostatic forces were considered using the particle mesh Ewald method. 40 ns production simulations were performed using NAMD over 30 nodes on the Lion-XF cluster at Penn State University using the NVE ensemble. (Phillips J C, et al. (2005) "Sealable molecular dynamics with NAMD," *J Comput Chem* 26(16):1781-1802.)

TABLE 1

FFA Production Profiles for Various Thioesterases Expressed in *E. coli*. This table provides the mole fractions of various FFAs and total FFA in the cell lysate for enzymes considered in this study as well as those found in literature. Computationally-predicted mutants are named Rx.My, rationally-designed mutants are named RDx.My, and randomly-generated mutants are labeled RM.My, where x is the Round number and y is the Mutant number. Heterologously-expressed and overexpressed thioesterases in *E. coli* are named using their GenBank accession label and mutants from literature (beginning with "CvB2MT", "TlE", or "UcFatB") are named as they are in the original source. "nd" indicates that the value was not determined or provided.

| Name | Organism | Fatty Acid Composition (mol %) | | | | | | | | | | Total FA ($\mu M$) | Notes | Source |
|---|---|---|---|---|---|---|---|---|---|---|---|---|---|---|
| | | 8:0 | 10:0 | 12:0 | 12:1 | 14:0 | 14:1 | 16:0 | 16:1 | 18:0 | 18:1 | | | |
| Control | *E. coli* | 2.4 ± 0.3 | 0.6 ± 0.2 | 3.6 ± 0.8 | 0.6 ± 0.9 | 17 ± 2 | 0.51 ± 0.06 | 57 ± 6 | 12 ± 2 | 1.3 ± 0.1 | 4.5 ± 0.6 | 300 ± 20 | — | — |
| WT | *E. coli* | 5.9 ± 0.3 | 1.09 ± 0.06 | 20 ± 1 | 7.5 ± 0.5 | 29 ± 2 | 7.1 ± 0.4 | 14.2 ± 0.8 | 11.6 ± 0.8 | 0.22 ± 0.01 | 2.1 ± 0.1 | 1900 ± 50 | — | — |
| R1.M1 | *E. coli* | 19 ± 2 | 6.0 ± 0.5 | 12.1 ± 0.7 | 31 ± 2 | 4.4 ± 0.3 | 14.9 ± 0.7 | 4.7 ± 0.7 | 6.4 ± 0.8 | 1.52 ± 0.10 | 0.11 ± 0.01 | 4300 ± 100 | — | — |
| R1.M2 | *E. coli* | 13 ± 2 | 2.2 ± 0.5 | 5.8 ± 0.5 | 2.0 ± 0.1 | 28 ± 2 | 3.7 ± 0.3 | 60 ± 10 | 8.5 ± 0.6 | 0.9 ± 0.2 | 4.1 ± 0.5 | 650 ± 30 | — | — |
| R1.M3 | *E. coli* | 5 ± 4 | 1 ± 2 | 3 ± 2 | 3 ± 2 | 11 ± 2 | 0.0 ± 0.0 | 60 ± 10 | 2.5 ± 0.5 | 1.9 ± 0.4 | 4 ± 1 | 190 ± 40 | — | — |
| R1.M4 | *E. coli* | 0.0 ± 0.0 | 0.0 ± 0.0 | 10 ± 10 | 3 ± 6 | 12 ± 2 | 3 ± 1 | 64 ± 8 | 3.2 ± 0.7 | 2.5 ± 0.5 | 3.5 ± 0.7 | 230 ± 30 | — | — |
| R1.M5 | *E. coli* | 0.0 ± 0.0 | 0.0 ± 0.0 | 3 ± 5 | 2 ± 3 | 14 ± 5 | 2 ± 3 | 70 ± 6 | 4 ± 1 | 2.3 ± 0.3 | 4.3 ± 0.6 | 160 ± 20 | — | — |
| R1.M6 | *E. coli* | 0.0 ± 0.0 | 0.0 ± 0.0 | 10 ± 10 | 4 ± 6 | 14 ± 5 | 2 ± 4 | 60 ± 10 | 4 ± 1 | 2.3 ± 0.5 | 4 ± 1 | 180 ± 30 | — | — |
| R1.M7 | *E. coli* | 0.0 ± 0.0 | 0.0 ± 0.0 | 2 ± 3 | 0.0 ± 0.0 | 13 ± 3 | 3 ± 3 | 72 ± 5 | 3.5 ± 0.8 | 2.4 ± 0.5 | 4.2 ± 0.8 | 170 ± 20 | — | — |
| R1.M8 | *E. coli* | 0.0 ± 0.0 | 0.0 ± 0.0 | 1 ± 2 | 0.0 ± 0.0 | 13 ± 4 | 1 ± 2 | 74 ± 5 | 3.3 ± 0.8 | 2.5 ± 0.7 | 4 ± 1 | 170 ± 30 | — | — |
| R1.M9 | *E. coli* | 0.0 ± 0.0 | 0.0 ± 0.0 | 5 ± 4 | 2 ± 3 | 14 ± 2 | 2 ± 3 | 69 ± 4 | 3.0 ± 0.4 | 2.6 ± 0.5 | 4.8 ± 0.9 | 180 ± 10 | — | — |
| R1.M10 | *E. coli* | 0.0 ± 0.0 | 0.0 ± 0.0 | 4 ± 3 | 0.0 ± 0.0 | 13 ± 1 | 1 ± 2 | 72 ± 3 | 3.3 ± 0.2 | 2.4 ± 0.2 | 4.8 ± 0.9 | 164 ± 8 | — | — |
| R1.M11 | *E. coli* | 0.0 ± 0.0 | 0.0 ± 0.0 | 3 ± 3 | 2 ± 3 | 14 ± 3 | 0.0 ± 0.0 | 73 ± 4 | 4 ± 1 | 2.6 ± 0.5 | 3.4 ± 0.7 | 180 ± 20 | — | — |
| R1.M12 | *E. coli* | 0.0 ± 0.0 | 0.0 ± 0.0 | 4 ± 3 | 2 ± 3 | 13 ± 2 | 3 ± 3 | 69 ± 4 | 2.9 ± 0.3 | 2.5 ± 0.3 | 4.0 ± 0.6 | 160 ± 10 | — | — |
| R2.M1 | *E. coli* | 7 ± 1 | 0.7 ± 0.0 | 1.2 ± 0.1 | 0.0 ± 0.0 | 12 ± 1 | 0.7 ± 0.1 | 47 ± 2 | 13.6 ± 0.7 | 0.7 ± 0.0 | 4.2 ± 0.3 | 510 ± 20 | — | — |
| R2.M2 | *E. coli* | 7.3 ± 0.4 | 0.0 ± 0.0 | 1.4 ± 0.1 | 0.0 ± 0.0 | 14.7 ± 0.7 | 0.9 ± 0.0 | 53.8 ± 0.9 | 15.7 ± 0.8 | 0.8 ± 0.0 | 4.7 ± 0.2 | 447 ± 8 | — | — |
| R2.M3 | *E. coli* | 8 ± 1 | 0.0 ± 0.0 | 1.4 ± 0.1 | 0.0 ± 0.0 | 11.8 ± 0.4 | 0.7 ± 0.1 | 47 ± 1 | 14.6 ± 0.7 | 0.8 ± 0.0 | 4.1 ± 0.2 | 480 ± 10 | — | — |
| R2.M4 | *E. coli* | 6.3 ± 0.7 | 0.6 ± 0.0 | 1.3 ± 0.1 | 0.0 ± 0.0 | 12.4 ± 0.8 | 0.7 ± 0.1 | 47 ± 2 | 14 ± 1 | 0.4 ± 0.0 | 3.7 ± 0.4 | 520 ± 20 | — | — |
| R2.M5 | *E. coli* | 5.9 ± 0.4 | 2.4 ± 0.2 | 12.9 ± 0.8 | 6.1 ± 0.4 | 38 ± 2 | 6.4 ± 0.5 | 8.4 ± 0.6 | 17 ± 2 | 0.1 ± 0.0 | 1.8 ± 0.2 | 3500 ± 100 | — | — |
| R2.M6 | *E. coli* | 1.2 ± 0.2 | 0.0 ± 0.0 | 1.3 ± 0.1 | 0.0 ± 0.0 | 11.6 ± 0.6 | 0.7 ± 0.0 | 49 ± 2 | 15.3 ± 0.9 | 0.7 ± 0.1 | 4.0 ± 0.3 | 500 ± 10 | — | — |
| R2.M7 | *E. coli* | 1.2 ± 0.1 | 0.0 ± 0.0 | 1.4 ± 0.0 | 0.0 ± 0.0 | 12.4 ± 0.5 | 0.7 ± 0.0 | 48 ± 1 | 16.2 ± 0.4 | 0.8 ± 0.0 | 4.1 ± 0.0 | 510 ± 10 | — | — |
| R2.M8 | *E. coli* | 1.5 ± 0.1 | 0.0 ± 0.0 | 1.6 ± 0.1 | 0.0 ± 0.0 | 15 ± 1 | 0.9 ± 0.0 | 57 ± 2 | 19 ± 1 | 0.8 ± 0.0 | 4.9 ± 0.5 | 440 ± 20 | — | — |
| R2.M9 | *E. coli* | 1.0 ± 0.1 | 0.0 ± 0.0 | 1.6 ± 0.1 | 0.0 ± 0.7 | 11.0 ± 0.7 | 0.6 ± 0.0 | 48 ± 1 | 15.4 ± 0.5 | 0.9 ± 0.1 | 4.1 ± 0.3 | 420 ± 10 | — | — |
| R2.M10 | *E. coli* | 1.2 ± 0.2 | 0.8 ± 0.1 | 1.5 ± 0.2 | 0.0 ± 0.0 | 14 ± 2 | 0.8 ± 0.1 | 56 ± 3 | 20 ± 3 | 0.8 ± 0.1 | 4.7 ± 0.4 | 380 ± 30 | — | — |
| R2.M11 | *E. coli* | 1.4 ± 0.1 | 0.0 ± 0.0 | 1.6 ± 0.1 | 0.0 ± 0.0 | 14.3 ± 0.9 | 0.8 ± 0.0 | 57 ± 1 | 18.5 ± 0.8 | 1.0 ± 0.0 | 5.1 ± 0.2 | 355 ± 10 | — | — |
| R2.M12 | *E. coli* | 1.3 ± 0.2 | 0.0 ± 0.0 | 1.6 ± 0.1 | 0.0 ± 0.0 | 13.1 ± 0.8 | 0.8 ± 0.0 | 57.1 ± 0.9 | 18.9 ± 0.5 | 2.0 ± 0.1 | 5.2 ± 0.2 | 343 ± 7 | — | — |
| R2.M13 | *E. coli* | 1.1 ± 0.3 | 0.9 ± 0.1 | 1.4 ± 0.3 | 0.0 ± 0.0 | 9 ± 3 | 0.6 ± 0.2 | 62 ± 8 | 11 ± 5 | 0.7 ± 0.7 | 4 ± 2 | 480 ± 90 | — | — |
| R2.M14 | *E. coli* | 1.8 ± 0.2 | 0.0 ± 0.0 | 2.6 ± 0.3 | 0.0 ± 0.0 | 15 ± 1 | 1.1 ± 0.1 | 44 ± 2 | 15 ± 1 | 0.9 ± 0.1 | 4.1 ± 0.4 | 460 ± 20 | — | — |
| R2.RD1 | *E. coli* | 2.9 ± 0.2 | 2.8 ± 0.2 | 20.5 ± 0.9 | 1.7 ± 0.1 | 31.2 ± 0.7 | 7.8 ± 0.3 | 17.1 ± 0.7 | 13.2 ± 0.5 | 0.8 ± 0.0 | 2.0 ± 0.1 | 2100 ± 30 | — | — |
| R2.RD2 | *E. coli* | 1.2 ± 0.0 | 0.8 ± 0.0 | 1.5 ± 0.1 | 0.0 ± 0.0 | 12.2 ± 0.3 | 0.7 ± 0.0 | 46.4 ± 0.9 | 15.4 ± 0.6 | 0.8 ± 0.0 | 4.5 ± 0.1 | 380 ± 8 | — | — |
| R2.RD3 | *E. coli* | 1.4 ± 0.1 | 0.9 ± 0.0 | 1.9 ± 0.0 | 0.0 ± 0.0 | 16 ± 1 | 0.8 ± 0.0 | 55.7 ± 0.9 | 17.8 ± 0.6 | 1.0 ± 0.0 | 4.7 ± 0.4 | 336 ± 6 | — | — |
| R2.RD4 | *E. coli* | 1.2 ± 0.1 | 0.7 ± 0.0 | 1.4 ± 0.0 | 0.0 ± 0.0 | 12.7 ± 0.8 | 0.6 ± 0.0 | 46 ± 2 | 15 ± 1 | 0.8 ± 0.1 | 4.1 ± 0.3 | 420 ± 10 | — | — |
| R2.RD5 | *E. coli* | 2.4 ± 0.1 | 0.9 ± 0.1 | 2.2 ± 0.1 | 0.0 ± 0.0 | 14 ± 1 | 1.3 ± 0.1 | 44 ± 2 | 15 ± 1 | 0.8 ± 0.1 | 3.9 ± 0.2 | 430 ± 10 | — | — |
| R3.M1 | *E. coli* | 15 ± 4 | 6 ± 2 | 35 ± 7 | 14 ± 4 | 14 ± 4 | 5 ± 2 | 6 ± 2 | 3.8 ± 0.8 | 0.1 ± 0.0 | 1.4 ± 0.4 | 3500 ± 400 | — | — |
| R3.M2 | *E. coli* | 26 ± 5 | 3.2 ± 0.7 | 13 ± 3 | 9 ± 2 | 21 ± 4 | 4.4 ± 0.8 | 11 ± 3 | 11 ± 2 | 0.1 ± 0.1 | 1.6 ± 0.5 | 4100 ± 400 | — | — |
| R3.M3 | *E. coli* | 25 ± 6 | 3 ± 1 | 19 ± 5 | 5 ± 1 | 23 ± 7 | 4 ± 1 | 12 ± 4 | 7 ± 2 | 0.2 ± 0.1 | 3 ± 1 | 2300 ± 300 | — | — |
| R3.M4 | *E. coli* | 50 ± 3 | 3.9 ± 0.5 | 9 ± 1 | 5.6 ± 0.7 | 13 ± 1 | 1.8 ± 0.2 | 8.9 ± 0.7 | 5.8 ± 0.5 | 0.1 ± 0.0 | 1.7 ± 0.1 | 4300 ± 300 | — | — |
| R3.M5 | *E. coli* | 3 ± 1 | 0.7 ± 0.6 | 2.5 ± 0.5 | 0.0 ± 0.0 | 17 ± 3 | 0.9 ± 0.2 | 53 ± 5 | 13 ± 2 | 0.2 ± 0.1 | 3.7 ± 0.5 | 380 ± 40 | — | — |
| R3.M6 | *E. coli* | 9.4 ± 0.8 | 1.4 ± 0.1 | 11.9 ± 0.8 | 4.3 ± 0.3 | 36 ± 2 | 6.3 ± 0.6 | 12.2 ± 0.9 | 16 ± 1 | 0.2 ± 0.0 | 2.5 ± 0.2 | 3400 ± 100 | — | — |
| R3.M7 | *E. coli* | 20 ± 9 | 6 ± 3 | 29 ± 10 | 11 ± 5 | 16 ± 7 | 4 ± 2 | 7 ± 3 | 5 ± 2 | 0.1 ± 0.1 | 1.7 ± 0.8 | 3100 ± 600 | — | — |
| R3.M8 | *E. coli* | 16 ± 2 | 6.1 ± 0.9 | 33 ± 4 | 14 ± 2 | 13 ± 2 | 5.4 ± 0.9 | 7 ± 1 | 4.1 ± 0.9 | 0.1 ± 0.1 | 1.8 ± 0.4 | 3900 ± 200 | — | — |
| R3.M9 | *E. coli* | 21 ± 3 | 4.7 ± 0.4 | 22 ± 2 | 7.7 ± 0.8 | 21 ± 2 | 4.1 ± 0.4 | 11 ± 2 | 6.3 ± 0.9 | 0.2 ± 0.0 | 2.9 ± 0.4 | 2500 ± 100 | — | — |
| R3.M10 | *E. coli* | 3 ± 1 | 1.0 ± 0.3 | 1.8 ± 0.6 | 0.0 ± 0.0 | 15 ± 5 | 0.8 ± 0.3 | 58 ± 9 | 15 ± 5 | 1.0 ± 0.3 | 4 ± 2 | 390 ± 70 | — | — |
| R3.RD1 | *E. coli* | 20 ± 20 | 4 ± 3 | 20 ± 10 | 7 ± 4 | 20 ± 30 | 4 ± 5 | 10 ± 10 | 10 ± 10 | 0.2 ± 0.2 | 2 ± 4 | 1300 ± 600 | — | — |

TABLE 1-continued

FFA Production Profiles for Various Thioesterases Expressed in *E. coli*. This table provides the mole fractions of various FFAs and total FFA in the cell lysate for enzymes considered in this study as well as those found in literature. Computationally-predicted mutants are named Rx.My, rationally-designed mutants are named RDx.My, and randomly-generated mutants are labeled RM.My, where x is the Round number and y is the Mutant number. Any mutant labeled in this manner derives from this study. Heterologously-expressed and overexpressed thioesterases in *E. coli* are named using their GenBank accession label and mutants from literature (beginning with "CvB2MT", "TE", or "UcFatB") are named as they are in the original source. "nd" indicates that the value was not determined or provided.

| Name | Organism | Fatty Acid Composition (mol %) | | | | | | | | | Total FA ($\mu$M) | Notes | Source |
|---|---|---|---|---|---|---|---|---|---|---|---|---|---|
| | | 8:0 | 10:0 | 12:0 | 12:1 | 14:0 | 14:1 | 16:0 | 16:1 | 18:0 | 18:1 | | | |
| R3.RD2 | E. coli | 19.2 ± 0.4 | 4.8 ± 0.1 | 20.5 ± 0.6 | 7.3 ± 0.2 | 24.7 ± 0.6 | 4.3 ± 0.1 | 11 ± 1 | 6.5 ± 0.3 | 0.2 ± 0.0 | 2.0 ± 0.1 | 1980 ± 30 | — | — |
| R3.RD3 | E. coli | 10 ± 3 | 3 ± 1 | 35 ± 9 | 13 ± 5 | 18 ± 6 | 6 ± 3 | 7 ± 3 | 6 ± 2 | 0.1 ± 0.0 | 1.5 ± 0.6 | 3300 ± 500 | — | — |
| R3.RD4 | E. coli | 13 ± 1 | 2.1 ± 0.1 | 22 ± 1 | 7.3 ± 0.3 | 29 ± 2 | 6.9 ± 0.4 | 9 ± 1 | 7.9 ± 0.6 | 0.1 ± 0.0 | 1.8 ± 0.2 | 4600 ± 100 | — | — |
| R3.RD5 | E. coli | 21 ± 4 | 5 ± 1 | 21 ± 4 | 8 ± 2 | 25 ± 5 | 5 ± 1 | 8 ± 2 | 6 ± 2 | 0.1 ± 0.0 | 1.8 ± 0.5 | 2700 ± 300 | — | — |
| R4.M1 | E. coli | 10.6 ± 0.4 | 2.6 ± 0.2 | 13.0 ± 0.9 | 4.1 ± 0.4 | 34 ± 1 | 5.2 ± 0.5 | 14.3 ± 0.4 | 11.5 ± 0.7 | 0.0 ± 0.0 | 2.2 ± 0.1 | 2850 ± 60 | — | — |
| R4.M2 | E. coli | 23 ± 1 | 4.1 ± 0.2 | 12.3 ± 0.3 | 9.0 ± 0.3 | 24 ± 1 | 4.2 ± 0.1 | 10.6 ± 0.7 | 11.5 ± 0.6 | 0.0 ± 0.0 | 1.3 ± 0.1 | 3430 ± 70 | — | — |
| R4.M3 | E. coli | 3.1 ± 0.2 | 0.9 ± 0.0 | 9.1 ± 0.3 | 3.8 ± 0.1 | 43.8 ± 0.9 | 7.1 ± 0.2 | 8.9 ± 0.3 | 19.7 ± 0.7 | 0.0 ± 0.0 | 2.1 ± 0.1 | 3370 ± 60 | — | — |
| R4.M4 | E. coli | 6.8 ± 0.6 | 1.2 ± 0.1 | 8.8 ± 0.9 | 3.9 ± 0.4 | 42 ± 3 | 6.2 ± 0.6 | 8.4 ± 0.8 | 19 ± 2 | 0.0 ± 0.0 | 1.8 ± 0.3 | 4700 ± 200 | — | — |
| R4.M5 | E. coli | 11 ± 1 | 3.0 ± 0.2 | 15 ± 1 | 8.9 ± 0.6 | 30 ± 3 | 4.3 ± 0.5 | 11 ± 1 | 14 ± 2 | 0.0 ± 0.0 | 1.8 ± 0.3 | 4700 ± 200 | — | — |
| R4.M6 | E. coli | 6.0 ± 0.6 | 2.3 ± 0.2 | 12.5 ± 0.8 | 5.9 ± 0.4 | 38 ± 2 | 6.5 ± 0.5 | 8.3 ± 0.6 | 17 ± 1 | 0.0 ± 0.0 | 2.0 ± 0.2 | 3800 ± 100 | — | — |
| R4.M7 | E. coli | 2.7 ± 0.4 | 1.2 ± 0.1 | 17 ± 2 | 2.7 ± 0.4 | 37 ± 2 | 4.9 ± 0.6 | 17.6 ± 0.9 | 11.1 ± 0.4 | 0.0 ± 0.0 | 1.8 ± 0.3 | 2200 ± 70 | — | — |
| R4.M8 | E. coli | 12.0 ± 0.8 | 2.4 ± 0.1 | 18.6 ± 0.7 | 6.7 ± 0.3 | 29.7 ± 0.9 | 5.2 ± 0.2 | 13.2 ± 0.6 | 10.2 ± 0.4 | 0.0 ± 0.0 | 1.9 ± 0.1 | 2890 ± 50 | — | — |
| R4.M9 | E. coli | 3.5 ± 0.4 | 1.0 ± 0.0 | 20 ± 1 | 4.7 ± 0.5 | 35.9 ± 0.9 | 4.8 ± 0.3 | 15.7 ± 0.9 | 9.5 ± 0.3 | 0.0 ± 0.0 | 2.6 ± 0.2 | 2550 ± 60 | — | — |
| R4.M10 | E. coli | 10.7 ± 0.4 | 2.6 ± 0.1 | 8.3 ± 0.3 | 5.5 ± 0.4 | 28.3 ± 0.8 | 6.6 ± 0.3 | 17.9 ± 0.5 | 15.7 ± 0.4 | 0.0 ± 0.0 | 2.0 ± 0.1 | 2280 ± 30 | — | — |
| R4.M11 | E. coli | 4.3 ± 0.7 | 0.0 ± 0.0 | 3.4 ± 0.8 | 4.2 ± 0.9 | 15 ± 2 | 28 ± 3 | 4.6 ± 0.3 | 30 ± 2 | 0.0 ± 0.0 | 2.9 ± 0.3 | 1110 ± 60 | — | — |
| R4.M12 | E. coli | 14.5 ± 0.5 | 0.0 ± 0.0 | 3.6 ± 0.2 | 0.0 ± 0.0 | 17.5 ± 0.8 | 0.0 ± 0.0 | 35.9 ± 0.7 | 12.8 ± 0.3 | 0.0 ± 0.0 | 3.3 ± 0.1 | 660 ± 10 | — | — |
| R4.M13 | E. coli | 37.9 ± 0.8 | 3.1 ± 0.1 | 4.7 ± 0.2 | 4.4 ± 0.2 | 17.0 ± 0.6 | 4.7 ± 0.2 | 13.4 ± 0.6 | 12.2 ± 0.3 | 0.0 ± 0.0 | 1.5 ± 0.1 | 2830 ± 40 | — | — |
| R4.M14 | E. coli | 20.0 ± 0.5 | 2.6 ± 0.1 | 15.3 ± 0.4 | 8.5 ± 0.4 | 24 ± 1 | 6.1 ± 0.2 | 6.5 ± 0.3 | 12.7 ± 0.8 | 0.0 ± 0.0 | 1.1 ± 0.1 | 2910 ± 50 | — | — |
| R4.M15 | E. coli | 33.2 ± 0.7 | 3.6 ± 0.2 | 6.0 ± 0.4 | 5.8 ± 0.3 | 20 ± 1 | 5.8 ± 0.4 | 10.9 ± 0.4 | 12.0 ± 0.9 | 0.0 ± 0.0 | 1.2 ± 0.1 | 3490 ± 70 | — | — |
| R4.M16 | E. coli | 9.6 ± 0.4 | 1.5 ± 0.1 | 8.9 ± 0.4 | 3.7 ± 0.2 | 39.3 ± 0.9 | 4.9 ± 0.2 | 11.5 ± 0.3 | 16.5 ± 0.6 | 0.0 ± 0.0 | 2.0 ± 0.1 | 4000 ± 70 | — | — |
| R4.M17 | E. coli | 18 ± 1 | 2.0 ± 0.2 | 10.9 ± 0.9 | 7.5 ± 0.5 | 26 ± 1 | 6.8 ± 0.5 | 13.3 ± 0.4 | 12.8 ± 0.7 | 0.0 ± 0.0 | 1.6 ± 0.1 | 3050 ± 80 | — | — |
| R4.M18 | E. coli | 15 ± 1 | 1.7 ± 0.1 | 9.2 ± 0.6 | 6.2 ± 0.3 | 28.0 ± 0.9 | 6.8 ± 0.3 | 14.4 ± 0.5 | 14.9 ± 0.5 | 0.0 ± 0.0 | 1.7 ± 0.1 | 3150 ± 60 | — | — |
| R4.RD1 | E. coli | 18 ± 2 | 2.6 ± 0.1 | 8.7 ± 0.4 | 6.7 ± 0.3 | 29 ± 1 | 4.1 ± 0.2 | 12.7 ± 0.8 | 16.2 ± 0.8 | 0.0 ± 0.0 | 1.7 ± 0.1 | 3230 ± 90 | — | — |
| R4.RD2 | E. coli | 35 ± 1 | 5.2 ± 0.1 | 16.4 ± 0.4 | 12.7 ± 0.3 | 16.8 ± 0.3 | 3.5 ± 0.1 | 3.9 ± 0.2 | 5.5 ± 0.4 | 0.0 ± 0.0 | 0.8 ± 0.1 | 3800 ± 60 | — | — |
| R4.RD3 | E. coli | 39 ± 1 | 5.0 ± 0.2 | 10.8 ± 0.5 | 8.4 ± 0.2 | 19.5 ± 0.7 | 3.5 ± 0.1 | 6.1 ± 0.5 | 7.2 ± 0.4 | 0.0 ± 0.0 | 1.0 ± 0.1 | 3500 ± 60 | — | — |
| R4.RD4 | E. coli | 22 ± 2 | 3.0 ± 0.2 | 7.9 ± 0.6 | 6.6 ± 0.4 | 21 ± 2 | 5.0 ± 0.3 | 17 ± 1 | 13.5 ± 0.9 | 0.0 ± 0.0 | 2.0 ± 0.2 | 2690 ± 90 | — | — |
| R4.RD5 | E. coli | 34 ± 2 | 5.6 ± 0.3 | 7.7 ± 0.3 | 7.7 ± 0.3 | 15.4 ± 0.5 | 4.3 ± 0.1 | 12.6 ± 0.6 | 9.3 ± 0.3 | 0.0 ± 0.0 | 1.5 ± 0.1 | 2910 ± 90 | — | — |
| R4.RD6 | E. coli | 29.5 ± 0.6 | 4.5 ± 0.2 | 7.2 ± 0.3 | 6.7 ± 0.4 | 16.9 ± 0.4 | 4.1 ± 0.2 | 15.7 ± 0.6 | 10.2 ± 0.7 | 0.0 ± 0.0 | 1.8 ± 0.1 | 2400 ± 30 | — | — |
| R4.RD7 | E. coli | 3.4 ± 0.4 | 1.6 ± 0.2 | 13.3 ± 0.5 | 0.8 ± 0.1 | 12 ± 1 | 1.1 ± 0.2 | 10.0 ± 0.4 | 43 ± 1 | 0.7 ± 0.0 | 3.7 ± 0.4 | 540 ± 10 | — | — |
| R4.RD8 | E. coli | 9.1 ± 0.6 | 2.5 ± 0.1 | 21 ± 1 | 6.5 ± 0.3 | 31 ± 2 | 5.0 ± 0.3 | 11 ± 1 | 12 ± 1 | 0.0 ± 0.0 | 2.0 ± 0.3 | 4100 ± 200 | — | — |
| R4.RD9 | E. coli | 6.5 ± 0.2 | 2.0 ± 0.0 | 21.4 ± 0.6 | 11.9 ± 0.3 | 27.9 ± 0.5 | 6.6 ± 0.2 | 8.4 ± 0.2 | 11.8 ± 0.5 | 0.0 ± 0.0 | 1.2 ± 0.3 | 2420 ± 30 | — | — |
| R4.RD10 | E. coli | 4.5 ± 0.2 | 1.3 ± 0.0 | 27.1 ± 0.6 | 10.6 ± 0.2 | 28.3 ± 0.8 | 8.4 ± 0.2 | 6.6 ± 0.3 | 9.8 ± 0.4 | 0.0 ± 0.0 | 1.2 ± 0.1 | 2570 ± 40 | — | — |
| R4.RD11 | E. coli | 4.8 ± 0.6 | 0.0 ± 0.0 | 26 ± 3 | 10 ± 1 | 26 ± 2 | 7.5 ± 0.8 | 15 ± 1 | 10.3 ± 0.7 | 0.0 ± 0.0 | 1.6 ± 0.1 | 1670 ± 80 | — | — |
| RM.M1 | E. coli | 4.5 | 1.6 | 15.2 | 4.4 | 47.7 | 6.1 | 15.8 | 0.2 | 0.1 | 3.2 | 3100 | a | — |
| RM.M2 | E. coli | 3.9 | 1.2 | 21.0 | 8.4 | 34.6 | 8.2 | 17.9 | 0.2 | 0.2 | 2.3 | 1700 | a | — |
| RM.M3 | E. coli | 2.6 | 0.7 | 17.9 | 5.8 | 41.0 | 7.2 | 19.7 | 0.2 | 0.2 | 2.8 | 2500 | a | — |
| RM.M4 | E. coli | 1.4 | 0.6 | 15.0 | 2.8 | 54.7 | 3.4 | 13.1 | 0.3 | 0.4 | 5.4 | 1100 | a | — |
| RM.M5 | E. coli | 4.0 | 2.4 | 3.8 | nd | 21.9 | nd | 5.2 | nd | 2.1 | 3.2 | 120 | a | — |
| RM.M6 | E. coli | 4.9 | 1.3 | 10.9 | 3.7 | 49.4 | 6.4 | 19.1 | 0.2 | 0.1 | 2.8 | 3100 | a | — |
| RM.M7 | E. coli | 2.5 | 0.7 | 16.8 | 5.5 | 42.2 | 6.2 | 20.7 | 0.2 | 0.2 | 2.9 | 2300 | a | — |
| RM.M8 | E. coli | 3.9 | 1.0 | 18.6 | 7.2 | 35.9 | 8.1 | 19.4 | 0.3 | 0.3 | 3.1 | 1500 | a | — |
| RM.M9 | E. coli | 3.4 | 2.3 | 4.2 | nd | 24.6 | nd | 7.6 | nd | 1.8 | 2.6 | 130 | a | — |
| RM.M10 | E. coli | 2.9 | 1.0 | 19.0 | 7.5 | 35.0 | 8.1 | 20.0 | 0.6 | 0.3 | 3.2 | 1200 | a | — |
| RM.M11 | E. coli | 4.1 | 2.4 | 3.9 | nd | 23.8 | nd | 5.2 | 1.8 | 1.8 | 2.9 | 120 | a | — |

TABLE 1-continued

FFA Production Profiles for Various Thioesterases Expressed in *E. coli*. This table provides the mole fractions of various FFAs and total FFA in the cell lysate for enzymes considered in this study as well as those found in literature. Computationally-predicted mutants are named Rx.My, rationally-designed mutants are named RDx.My, and randomly-generated mutants are labeled RM.My, where x is the Round number and y is the Mutant number. Any mutant labeled in this manner derives from this study. Heterologously-expressed and overexpressed thioesterases in *E. coli* are named using their GenBank accession label and mutants from literature (beginning with "CvB2MT", "TE", or "UcFatB") are named as they are in the original source. "nd" indicates that the value was not determined or provided.

| Name | Organism | 8:0 | 10:0 | 12:0 | 12:1 | 14:0 | 14:1 | 16:0 | 16:1 | 18:0 | 18:1 | Total FA (μM) | Notes | Source |
|---|---|---|---|---|---|---|---|---|---|---|---|---|---|---|
| RM.M12 | E. coli | 5.5 | 1.2 | 18.6 | 3.5 | 48.9 | 3.7 | 12.7 | 0.1 | 0.2 | 4.4 | 3300 | a | — |
| RM.M13 | E. coli | 3.7 | nd | 3.9 | nd | 32.0 | nd | 5.1 | 1.7 | 1.8 | 2.6 | 140 | a | — |
| RM.M14 | E. coli | 2.6 | 1.1 | 19.9 | 8.4 | 33.2 | 8.3 | 17.2 | 0.8 | 0.4 | 2.7 | 850 | a | — |
| RM.M15 | E. coli | 3.2 | 0.6 | 11.8 | 5.0 | 44.4 | 11.0 | 20.4 | 0.2 | 0.2 | 2.0 | 3300 | a | — |
| RM.M16 | E. coli | 3.2 | 1.1 | 19.5 | 7.7 | 35.2 | 8.0 | 18.2 | 0.5 | 0.4 | 2.7 | 1100 | a | — |
| RM.M17 | E. coli | 3.0 | 0.9 | 15.6 | 5.8 | 41.0 | 7.5 | 20.6 | 0.4 | 0.2 | 2.6 | 1600 | a | — |
| RM.M18 | E. coli | 3.2 | 1.1 | 19.1 | 7.3 | 36.5 | 8.3 | 18.1 | 0.4 | 0.2 | 2.6 | 1200 | a | — |
| RM.M19 | E. coli | 3.4 | 1.0 | 19.3 | 7.3 | 35.2 | 7.5 | 19.9 | 0.6 | 0.4 | 3.2 | 1300 | a | — |
| RM.M20 | E. coli | 3.1 | 0.9 | 18.3 | 8.1 | 38.1 | 8.6 | 18.4 | 0.2 | 0.2 | 2.0 | 1600 | a | — |
| RM.M21 | E. coli | 2.5 | 0.7 | 16.6 | 3.6 | 49.3 | 5.5 | 15.9 | 0.1 | 0.2 | 4.2 | 3200 | a | — |
| RM.M22 | E. coli | 1.4 | 0.7 | 11.0 | 0.5 | 66.6 | 1.4 | 8.7 | 0.4 | 0.4 | 5.6 | 780 | a | — |
| RM.M23 | E. coli | 4.6 | 2.7 | 4.1 | nd | 23.2 | nd | 6.9 | nd | 2.0 | 3.0 | 120 | a | — |
| RM.M24 | E. coli | 3.8 | 1.6 | 7.5 | nd | 41.8 | 1.1 | 6.3 | 1.1 | 1.2 | 1.5 | 200 | a | — |
| RM.M25 | E. coli | 2.7 | 0.9 | 23.4 | 4.1 | 45.9 | 4.4 | 14.2 | 0.1 | 0.1 | 2.9 | 3800 | a | — |
| RM.M26 | E. coli | 3.9 | 2.5 | 3.6 | nd | 20.3 | nd | 6.2 | nd | 2.3 | 3.1 | 110 | a | — |
| RM.M27 | E. coli | 3.4 | 0.8 | 19.1 | 4.8 | 46.6 | 6.9 | 13.7 | 0.1 | 0.1 | 3.5 | 3600 | a | — |
| RM.M28 | E. coli | 3.9 | 2.4 | 3.1 | nd | 18.9 | nd | 6.2 | 1.8 | 2.2 | 3.0 | 110 | a | — |
| RM.M29 | E. coli | 21.9 | 1.7 | 16.3 | 2.7 | 38.0 | 3.0 | 11.3 | 0.2 | 0.2 | 3.8 | 2500 | a | — |
| RM.M30 | E. coli | 3.5 | 0.8 | 17.9 | 7.0 | 39.8 | 7.4 | 19.0 | 0.2 | 0.2 | 2.2 | 2000 | a | — |
| RM.M31 | E. coli | 5.9 | 1.6 | 7.9 | 2.1 | 43.9 | 6.3 | 13.0 | 0.5 | 1.0 | 4.1 | 400 | a | — |
| RM.M32 | E. coli | 2.9 | 0.9 | 17.6 | 6.3 | 40.3 | 7.0 | 19.1 | 0.5 | 0.3 | 2.6 | 1700 | a | — |
| RM.M33 | E. coli | 4.9 | 2.3 | 4.0 | nd | 21.6 | nd | 6.5 | nd | 1.9 | 2.7 | 120 | a | — |
| RM.M34 | E. coli | 3.1 | 1.0 | 20.9 | 7.8 | 36.4 | 8.2 | 17.8 | 0.2 | 0.3 | 2.2 | 1600 | a | — |
| RM.M35 | E. coli | 3.5 | 1.0 | 16.4 | 7.5 | 38.1 | 7.4 | 18.0 | 0.6 | 0.5 | 2.7 | 920 | a | — |
| RM.M36 | E. coli | 3.2 | 1.1 | 21.7 | 7.4 | 38.9 | 6.6 | 17.8 | 0.1 | 0.1 | 1.9 | 2500 | a | — |
| RM.M37 | E. coli | 3.4 | 1.2 | 20.5 | 7.7 | 35.1 | 7.9 | 16.9 | 0.5 | 0.4 | 2.5 | 1000 | a | — |
| RM.M38 | E. coli | 2.2 | 0.8 | 19.1 | 5.3 | 43.0 | 6.2 | 18.9 | 0.2 | 0.2 | 3.0 | 2700 | a | — |
| RM.M39 | E. coli | 4.9 | 2.3 | 31.6 | 12.4 | 28.1 | 6.9 | 10.4 | 0.3 | 0.2 | 1.9 | 2100 | a | — |
| RM.M40 | E. coli | 2.5 | 0.8 | 19.1 | 3.9 | 48.3 | 5.0 | 15.8 | 0.1 | 0.1 | 3.5 | 3500 | a | — |
| RM.M41 | E. coli | 2.2 | 0.7 | 18.6 | 5.7 | 43.8 | 7.3 | 17.7 | 0.3 | 0.2 | 2.6 | 3200 | a | — |
| RM.M42 | E. coli | 5.0 | 1.1 | 9.2 | 4.7 | 42.8 | 15.5 | 18.7 | 0.2 | 0.2 | 1.4 | 3500 | a | — |
| RM.M43 | E. coli | 3.5 | 1.1 | 20.0 | 7.8 | 35.4 | 8.6 | 16.8 | 0.5 | 0.4 | 2.4 | 960 | a | — |
| RM.M44 | E. coli | 3.2 | 1.0 | 20.0 | 7.6 | 37.3 | 8.2 | 17.7 | 0.3 | 0.3 | 2.3 | 1500 | a | — |
| RM.M45 | E. coli | 4.3 | 2.4 | 3.9 | nd | 21.7 | nd | 6.7 | 1.8 | 2.3 | 2.7 | 120 | a | — |
| RM.M46 | E. coli | 4.6 | 2.6 | 3.9 | nd | 22.0 | nd | 6.5 | nd | 2.0 | 2.7 | 110 | a | — |
| RM.M47 | E. coli | 1.4 | 0.7 | 10.4 | 0.5 | 63.6 | 1.2 | 8.0 | nd | 0.5 | 6.9 | 540 | a | — |
| RM.M48 | E. coli | 1.9 | 0.7 | 18.5 | 5.4 | 43.6 | 7.0 | 18.6 | 0.6 | 0.2 | 2.7 | 2700 | a | — |
| RM.M49 | E. coli | 2.6 | 1.5 | 8.8 | nd | 51.2 | 1.1 | 6.5 | 0.3 | 1.4 | 1.5 | 210 | a | — |
| RM.M50 | E. coli | 4.5 | 2.4 | 3.6 | nd | 21.4 | nd | 6.3 | nd | 2.0 | 2.6 | 120 | a | — |
| RM.M51 | E. coli | 4.5 | 2.4 | 3.7 | nd | 21.8 | nd | 6.3 | nd | 2.1 | 2.7 | 120 | a | — |
| RM.M52 | E. coli | 3.1 | 1.1 | 19.3 | 7.2 | 37.5 | 7.7 | 19.2 | 0.2 | 0.3 | 2.4 | 1400 | a | — |
| RM.M53 | E. coli | 3.1 | 1.4 | 18.4 | 7.4 | 32.9 | 8.1 | 17.2 | 0.4 | 0.6 | 3.5 | 550 | a | — |
| RM.M54 | E. coli | 3.9 | 2.1 | 3.9 | nd | 30.3 | nd | 6.7 | nd | 1.7 | 2.4 | 130 | a | — |
| RM.M55 | E. coli | 2.9 | 1.1 | 20.6 | 8.0 | 35.3 | 8.1 | 17.6 | 0.5 | 0.4 | 2.5 | 1100 | a | — |

TABLE 1-continued

FFA Production Profiles for Various Thioesterases Expressed in *E. coli*. This table provides the mole fractions of various FFAs and total FFA in the cell lysate for enzymes considered in this study as well as those found in literature. Computationally-predicted mutants are named Rx.My, rationally-designed mutants are named RDx.My, and randomly-generated mutants are labeled RM.My, where x is the Round number and y is the Mutant number. Any mutant labeled in this manner derives from this study. Heterologously-expressed and overexpressed thioesterases in *E. coli* are named using their GenBank accession label and mutants from literature (beginning with "CvB2MT", "TfE", or "UcFatB") are named as they are in the original source. "nd" indicates that the value was not determined or provided.

| Name | Organism | 8:0 | 10:0 | 12:0 | 12:1 | 14:0 | 14:1 | 16:0 | 16:1 | 18:0 | 18:1 | Total FA (µM) | Notes | Source |
|---|---|---|---|---|---|---|---|---|---|---|---|---|---|---|
| RM.M56 | *E. coli* | 4.3 | 1.6 | 20.1 | 7.8 | 27.1 | 7.0 | 16.9 | 0.4 | 0.7 | 4.0 | 540 | a | — |
| RM.M57 | *E. coli* | 4.4 | 3.7 | 23.0 | 19.3 | 27.9 | 5.5 | 12.9 | 0.1 | 0.2 | 1.6 | 1900 | a | — |
| RM.M58 | *E. coli* | 2.8 | 1.3 | 21.9 | 8.5 | 33.0 | 7.6 | 17.6 | 0.3 | 0.5 | 2.8 | 930 | a | — |
| RM.M59 | *E. coli* | 4.3 | 1.1 | 12.7 | 5.1 | 42.8 | 7.7 | 21.4 | 0.2 | 0.2 | 2.3 | 1600 | a | — |
| RM.M60 | *E. coli* | 2.8 | 0.9 | 23.0 | 6.8 | 38.5 | 6.6 | 17.5 | 0.3 | 0.1 | 2.4 | 2900 | a | — |
| RM.M61 | *E. coli* | 4.3 | 1.6 | 20.2 | 8.2 | 29.8 | 7.4 | 15.6 | 0.6 | 0.7 | 3.7 | 570 | a | — |
| AAC49179 | *C. palustris* | 97.5 ± 0.2 | 0.9 ± 0.1 | 0.6 ± 0.1 | 0.2 ± 0.0 | 0.2 ± 0.1 | 0.2 ± 0.0 | 0.1 ± 0.1 | 0.1 ± 0.1 | nd | nd | 710 ± 50 | — | 1 |
| AAB71731 | *U. americana* | 44 ± 3 | 23 ± 1 | 3.7 ± 0.4 | 7.9 ± 0.9 | 9.8 ± 0.8 | 1.5 ± 0.2 | 1.4 ± 0.1 | 4.4 ± 0.7 | nd | nd | 1100 ± 60 | — | 1 |
| AAG43857 | *I. germanica* | 3.3 ± 0.4 | 0.5 ± 0.1 | 0.7 ± 0.1 | 1.0 ± 0.1 | 30 ± 3 | 0.3 ± 0.1 | 20 ± 3 | 44 ± 4 | nd | nd | 260 ± 20 | — | 1 |
| AAG43858 | *I. germanica* | 8 ± 4 | nd | 1 ± 1 | nd | 30 ± 10 | nd | 20 ± 10 | 40 ± 20 | nd | nd | 15 ± 5 | — | 1 |
| EER87824 | *S. bicolor* | 4.8 ± 0.7 | 0.2 ± 0.0 | 1.6 ± 0.3 | 0.4 ± 0.1 | 46 ± 5 | nd | 13 ± 3 | 35 ± 6 | nd | nd | 130 ± 10 | — | 1 |
| EER88593 | *S. bicolor* | 6 ± 1 | 0.7 ± 0.1 | 3.2 ± 0.5 | 0.6 ± 0.3 | 45 ± 5 | 3.3 ± 0.9 | 11 ± 2 | 31 ± 4 | nd | nd | 91 ± 8 | — | 1 |
| AEM72519 | *C. nucifera* | 14 ± 3 | 1.1 ± 0.3 | 1.4 ± 0.3 | 1.1 ± 0.1 | 44 ± 5 | 0.4 ± 0.3 | 6 ± 1 | 31 ± 5 | nd | nd | 130 ± 10 | — | 1 |
| AEM72520 | *C. nucifera* | 1.7 ± 0.2 | 0.1 ± 0.0 | 1.0 ± 0.2 | 0.3 ± 0.1 | 36 ± 3 | 0.7 ± 0.1 | 16 ± 2 | 44 ± 3 | nd | nd | 570 ± 30 | — | 1 |
| AEM72521 | *C. nucifera* | 11.1 ± 0.8 | 1.2 ± 0.1 | 34 ± 2 | 6.1 ± 0.6 | 14 ± 2 | 23 ± 3 | 2 ± 1 | 9 ± 3 | nd | nd | 200 ± 10 | — | 1 |
| AEM72522 | *C. viscosissima* | 52 ± 6 | 26 ± 5 | 7 ± 2 | 6 ± 2 | 7 ± 2 | 0.9 ± 0.6 | 26 ± 2 | 19 ± 2 | nd | nd | 79 ± 10 | — | 1 |
| AEM72523 | *C. viscosissima* | 4 ± 1 | 0.5 ± 0.2 | 1.0 ± 0.3 | 0.9 ± 0.4 | 47 ± 3 | 0.7 ± 0.5 | nd | nd | nd | nd | 249 ± 9 | — | 1 |
| AEM72524 | *C. viscosissima* | 7 ± 5 | 5 ± 3 | 2 ± 1 | 2 ± 1 | 84 ± 6 | 3 ± 3 | nd | nd | nd | nd | 19 ± 2 | — | 1 |
| AAD42220 | *E. guineensis* | 14 ± 4 | 1.9 ± 0.8 | 2 ± 1 | 2 ± 1 | 47 ± 5 | 0.2 ± 0.1 | 26 ± 5 | nd | nd | nd | 37 ± 4 | — | 1 |
| EDQ65090 | *P. patens* | 9 ± 1 | 0.4 ± 0.1 | 0.4 ± 0.1 | 0.2 ± 0.0 | 42 ± 4 | 0.9 ± 0.2 | 16 ± 3 | 32 ± 4 | nd | nd | 380 ± 30 | — | 1 |
| EER96252 | *S. bicolor* | 5.8 ± 0.9 | 1.8 ± 0.8 | 1.2 ± 0.3 | 1.1 ± 0.4 | 34 ± 3 | nd | 18 ± 3 | 37 ± 3 | nd | nd | 180 ± 10 | — | 1 |
| EES11622 | *S. bicolor* | 5 ± 3 | nd | nd | nd | 50 ± 10 | nd | 15 ± 4 | 29 ± 9 | nd | nd | 9 ± 2 | — | 1 |
| EEH52851 | *M. pusilla* | 4 ± 2 | nd | 0 ± 1 | 0.6 ± 0.1 | 65 ± 4 | 8 ± 4 | nd | 23 ± 3 | nd | nd | 16 ± 2 | — | 1 |
| ACL08376 | *D. vulgaris* | 29 ± 1 | 3.5 ± 0.2 | 7.9 ± 0.3 | 24 ± 1 | 6.0 ± 0.4 | 24 ± 1 | 1.2 ± 0.4 | 2.6 ± 0.3 | nd | nd | 330 ± 9 | — | 1 |
| CAH09236 | *B. fragilis* | 20 ± 2 | 2.7 ± 0.2 | 3.6 ± 0.4 | 19 ± 1 | 5.1 ± 0.3 | 25 ± 1 | 2.2 ± 0.3 | 5.4 ± 0.4 | nd | nd | 215 ± 6 | — | 1 |
| ABR43801 | *P. distasonis* | 18 ± 5 | 6.3 ± 0.4 | 16 ± 1 | 9.3 ± 0.8 | 21 ± 2 | 27 ± 2 | nd | nd | nd | nd | 70 ± 4 | — | 1 |
| AAO77182 | *B. thetaiotaomicron* | 13.4 ± 0.8 | 2.1 ± 0.2 | 4.6 ± 0.7 | 16.7 ± 0.9 | 6 ± 1 | 26 ± 1 | 1.2 ± 0.4 | 2.6 ± 0.4 | nd | nd | 60 ± 3 | — | 1 |
| ABG82470 | *C. perfringens* | 70 ± 4 | 3.0 ± 0.5 | nd | 1.1 ± 0.2 | nd | 9 ± 2 | nd | nd | nd | nd | 72 ± 10 | — | 1 |
| EEG55387 | *C. asparagiforme* | 26 ± 6 | 6 ± 1 | 7 ± 2 | 1.6 ± 0.8 | 35 ± 9 | 18 ± 6 | 0.4 ± 0.2 | 1.3 ± 0.9 | nd | nd | 26 ± 4 | — | 1 |
| BET61113 | *M. formatexigens* | 31.8 ± 0.3 | 5.1 ± 0.1 | 4.3 ± 0.2 | 8.9 ± 0.5 | 1.9 ± 0.2 | 10.5 ± 0.2 | 0 ± 1 | 1.2 ± 0.1 | nd | nd | 381 ± 3 | — | 1 |
| EDV77528 | *G. sp.* | 9 ± 4 | 2 ± 1 | 7 ± 3 | 30 ± 10 | 11 ± 3 | 32 ± 8 | nd | 2 ± 1 | nd | nd | 60 ± 10 | — | 1 |
| BAH81730 | *S. dysgalactiae* | 30 ± 1 | 5.0 ± 0.2 | 5.7 ± 0.3 | 13.5 ± 0.7 | 4.4 ± 0.3 | 20 ± 1 | 0.3 ± 0.1 | 3.3 ± 0.1 | nd | nd | 620 ± 10 | — | 1 |
| AB163754 | *L. brevis* | 55.5 ± 0.7 | 2.6 ± 0.1 | 3.8 ± 0.1 | 7.9 ± 0.2 | 1.9 ± 0.1 | 6.3 ± 0.2 | nd | 0.7 ± 0.1 | nd | nd | 710 ± 10 | — | 1 |
| CAD63310 | *L. plantarum* | 68.0 ± 0.8 | 1.2 ± 0.1 | 2.8 ± 0.2 | 4.6 ± 0.2 | 1.9 ± 0.1 | 6.9 ± 0.4 | nd | 0.5 ± 0.1 | nd | nd | 1400 ± 10 | — | 1 |
| EEI82564 | *A. tetradius* | 87 ± 2 | 2.2 ± 0.3 | 1.1 ± 0.2 | 2.8 ± 0.5 | 1.2 ± 0.2 | 3.0 ± 0.5 | 0.1 ± 0.1 | 0.7 ± 0.1 | nd | nd | 1400 ± 100 | — | 1 |
| CAE80300 | *B. bacteriovorus* | 37 ± 3 | 3.3 ± 0.5 | 6.7 ± 0.7 | 7.6 ± 0.6 | 8.2 ± 0.7 | 28 ± 2 | 1.6 ± 0.2 | 6.6 ± 0.5 | nd | nd | 330 ± 20 | — | 1 |
| ABN54268 | *R. thermocellum* | 8.4 ± 0.4 | 4.5 ± 0.2 | 2.7 ± 0.2 | 7.9 ± 0.4 | 9.8 ± 0.8 | 60 ± 1 | 0.8 ± 0.7 | 4.7 ± 0.4 | nd | nd | 98 ± 3 | — | 1 |
| Q9SJE2 | *A. thaliana* | nd | nd | nd | nd | 19.4 | nd | 53.0 | 14.9 | 1.0 | 10.9 | 100 | a, c | 2 |
| AAX51637 | *M. longifolia* | nd | nd | nd | nd | 7 ± 4 | nd | 66 ± 5 | nd | 15 ± 2 | 10 ± 3 | nd | b, c, d | 3 |
| AAX51636 | *D. butyracea* | nd | nd | nd | nd | 17.8 ± 0.6 | nd | 71 ± 4 | 0.6 ± 0.1 | 2.6 ± 0.1 | 5.2 ± 0.4 | nd | b | 4 |
| AHF72806 | *L. communis* | nd | 6 ± 2 | 17 ± 6 | nd | 16 ± 2 | nd | 17 ± 2 | 20 ± 3 | 1.5 ± 0.2 | 15 ± 2 | nd | b | 5 |
| EST75919 | *E. coli* | nd | 0.8 | 12.8 | 2.2 | 49.5 | 2.6 | 11.9 | 11.9 | 0.9 | 4.0 | 1400 | a, b | 6 |
| AAC49151 | *C. camphorum* | nd | 4.5 ± 0.2 | 5.8 | 0.6 | 27.6 | 12.4 | 24.2 | 16.9 | 1.2 | 11.3 | 1600 | a | 7 |
| Q41635 | *U. californica* | nd | nd | 63.2 | 13.7 | 3.0 | 10.2 | 1.6 | 4.3 | nd | 4.0 | 1000 | — | 8 |

TABLE 1-continued

FFA Production Profiles for Various Thioesterases Expressed in *E. coli*. This table provides the mole fractions of various FFAs and total FFA in the cell lysate for enzymes considered in this study as well as those found in literature. Computationally-predicted mutants are named Rx.My, rationally-designed mutants are named RDx.My, and randomly-generated mutants are labeled RM.My, where x is the Round number and y is the Mutant number. Any mutant labeled in this manner derives from this study. Heterologously-expressed and overexpressed thioesterases in *E. coli* are named using their GenBank accession label and mutants from literature (beginning with "CvB2MT", "TE", or "UcFatB") are named as they are in the original source. "nd" indicates that the value was not determined or provided.

| Name | Organism | Fatty Acid Composition (mol %) | | | | | | | | | | Total FA (µM) | Notes | Source |
|---|---|---|---|---|---|---|---|---|---|---|---|---|---|---|
| | | 8:0 | 10:0 | 12:0 | 12:1 | 14:0 | 14:1 | 16:0 | 16:1 | 18:0 | 18:1 | | | |
| ADB79567 | A. hypogaea L. | nd | nd | 4 ± 1 | nd | 8 ± 2 | nd | 45 ± 3 | 14 ± 3 | 2.3 ± 0.3 | 5.8 ± 0.9 | nd | b | 9 |
| AAX51636 | D. butyracea | nd | nd | 8.3 | nd | 6.8 | nd | 43.6 | 5.1 | 29.7 | 6.5 | 580 ± 40 | a, b | 10 |
| Q9SQI3 | G. hirsutum | nd | nd | 0.1 | nd | 35.6 | nd | 21.3 | 36.6 | 1.4 | 4.9 | 3100 ± 200 | a, b | 10 |
| XP002515564 | R. communis | nd | nd | 0.1 | nd | 44.4 | nd | 17.0 | 32.9 | 1.2 | 4.4 | 9200 ± 100 | a, b | 10 |
| ABU96744 | J. curcas | nd | nd | 0.0 | nd | 44.4 | nd | 17.5 | 32.5 | 1.2 | 4.4 | 8700 ± 200 | a, b | 10 |
| WP004921669 | A. baylyi | 20 ± 1 | 9 ± 2 | 15 ± 2 | 8.0 ± 0.3 | 17 ± 1 | 6 ± 1 | 8 ± 2 | 10 ± 4 | 2.3 ± 0.1 | 1.6 ± 0.4 | 18000 ± 2000 | b | 11 |
| CAA57794 | A. brasilense | nd | nd | nd | nd | 5.6 ± 0.3 | nd | 53 ± 3 | 9.2 ± 0.6 | 0.9 ± 0.0 | 29 ± 2 | nd | b | 12 |
| EEC51251 | P. tricornutum | nd | nd | 12.4 | nd | 2.8 ± 0.2 | nd | 43.0 ± 0.2 | 14.4 ± 0.3 | 2.2 ± 0.3 | 14.2 ± 0.0 | nd | b | 13 |
| AAL79361 | H. annuus L. | nd | nd | 6.2 | nd | nd | nd | 39.9 | 3.6 | 21.6 | 10.9 | nd | a | 14 |
| ADA64920 | L. lactis | 3.6 ± 0.6 | 1.7 ± 0.2 | 2.3 ± 0.3 | nd | 4.6 ± 0.6 | 0.1 | 51 ± 3 | 6.6 ± 0.2 | 26 ± 2 | 4.5 ± 0.5 | 2800 ± 100 | — | 15 |
| AAC72882 | C. hookeriana | 93.5 | 2.2 | 0.9 | 0.2 | 0.0 | 0.1 | 1.2 | 0.0 | nd | 0.0 | 930 | a | 16 |
| rTE3 | C. viscosissima | 42.5 | 26.6 | 4.1 | 9.5 | 1.4 | 1.6 | 1.3 | 0.8 | nd | nd | 510 | a | 16 |
| rTE4 | C. viscosissima | 24.3 | 36.0 | 4.1 | 12.2 | 3.6 | 3.8 | 0.0 | 3.0 | nd | nd | 490 | a | 16 |
| rTE8 | C. viscosissima | 17.9 | 10.2 | 3.4 | 5.3 | 31.6 | 6.4 | 0.0 | 17.9 | nd | nd | 87 | a | 16 |
| rTE12 | C. viscosissima | 18.5 | 43.0 | 2.8 | 15.6 | 9.9 | 0.0 | 0.0 | 0.0 | nd | nd | 50 | a | 16 |
| rTE15 | C. viscosissima | 4.1 | 21.0 | 14.7 | 34.3 | 5.1 | 10.0 | 0.0 | 0.0 | nd | nd | 56 | a | 16 |
| rTE16 | C. viscosissima | 38.9 | 15.3 | 9.3 | 16.2 | 2.7 | 7.5 | 0.0 | 1.8 | nd | nd | 820 | a | 16 |
| rTE20 | C. viscosissima | 16.1 | 19.9 | 12.4 | 24.3 | 2.8 | 13.2 | 0.0 | 2.2 | nd | nd | 390 | a | 16 |
| rTE24 | C. viscosissima | 19.8 | 4.1 | 6.2 | 7.3 | 27.8 | 6.2 | 1.0 | 23.9 | nd | nd | 280 | a | 16 |
| rTE28 | C. viscosissima | 4.8 | 1.0 | 1.3 | 1.7 | 41.4 | 1.8 | 2.3 | 44.8 | nd | nd | 280 | a | 16 |
| rTE32 | C. viscosissima | 25.5 | 24.6 | 11.0 | 16.1 | 4.8 | 4.2 | 0.0 | 4.3 | nd | nd | 490 | a | 16 |
| rTE36 | C. viscosissima | 6.9 | 18.5 | 13.1 | 17.6 | 11.7 | 17.4 | 0.0 | 9.2 | nd | nd | 190 | a | 16 |
| rTE40 | C. viscosissima | 16.7 | 3.1 | 6.0 | 4.7 | 32.0 | 10.6 | 0.0 | 20.1 | nd | nd | 140 | a | 16 |
| rTE44 | C. viscosissima | 6.8 | 1.7 | 1.3 | 1.1 | 46.4 | 5.8 | 0.0 | 31.3 | nd | nd | 47 | a | 16 |
| rTE48 | C. viscosissima | 23.8 | 17.8 | 8.9 | 18.3 | 1.7 | 5.8 | 0.8 | 0.8 | nd | nd | 810 | a | 16 |
| rTE51 | C. viscosissima | 0.0 | 20.9 | 2.4 | 30.0 | 21.8 | 2.1 | 0.0 | 0.0 | nd | nd | 6.4 | a | 16 |
| rTE52 | C. viscosissima | 31.0 | 11.4 | 5.3 | 12.3 | 1.6 | 4.6 | 0.1 | 1.0 | nd | nd | 870 | a | 16 |
| rTE56 | C. viscosissima | 24.9 | 5.6 | 7.5 | 8.2 | 26.2 | 4.6 | 0.8 | 14.8 | nd | nd | 410 | a | 16 |
| rTE60 | C. viscosissima | 3.6 | 1.0 | 1.1 | 0.9 | 54.9 | 0.1 | 10.1 | 27.4 | nd | nd | 140 | a | 16 |
| CvB2MT1 | C. viscosissima | 34.6 | 0.0 | 0.0 | 0.0 | 0.0 | 19.9 | 0.0 | 0.0 | nd | nd | 2.4 | a | 16 |
| CvB2MT2 | C. viscosissima | 8.9 | 4.6 | 10.0 | 9.7 | 24.5 | 4.3 | 0.1 | 19.5 | nd | nd | 82 | a | 16 |
| CvB2MT3 | C. viscosissima | 17.2 | 4.1 | 2.1 | 4.6 | 40.1 | 0.6 | 0.0 | 21.6 | nd | nd | 90 | a | 16 |
| CvB2MT4 | C. viscosissima | 3.7 | 0.6 | 0.0 | 0.2 | 60.9 | 0.1 | 9.3 | 24.5 | nd | nd | 200 | a | 16 |
| CvB2MT5 | C. viscosissima | 1.5 | 0.2 | 0.0 | 0.0 | 81.5 | 0.0 | 2.9 | 13.9 | nd | nd | 460 | a | 16 |
| CvB2MT6 | C. viscosissima | 38.2 | 5.8 | 21.7 | 0.0 | 3.4 | 13.9 | 0.0 | 0.0 | nd | nd | 31 | a | 16 |
| CvB2MT7 | C. viscosissima | 6.1 | 0.6 | 0.0 | 9.1 | 62.2 | 0.0 | 0.9 | 28.8 | nd | nd | 47 | a | 16 |
| CvB2MT8 | C. viscosissima | 3.9 | 0.3 | 0.0 | 0.0 | 58.0 | 0.0 | 4.4 | 32.8 | nd | nd | 74 | a | 16 |
| CvB2MT9 | C. viscosissima | 1.5 | 0.3 | 0.3 | 0.4 | 52.6 | 0.6 | 10.4 | 33.7 | nd | nd | 410 | a | 16 |
| CvB2MT10 | C. viscosissima | 21.6 | 9.6 | 8.8 | 14.1 | 9.8 | 16.4 | 0.0 | 9.9 | nd | nd | 170 | a | 16 |
| CvB2MT11 | C. viscosissima | 4.3 | 1.5 | 3.8 | 4.0 | 45.5 | 4.9 | 11.9 | 23.5 | nd | nd | 120 | a | 16 |
| CvB2MT12 | C. viscosissima | 12.5 | 7.2 | 16.4 | 15.4 | 15.3 | 20.0 | 0.0 | 7.8 | nd | nd | 150 | a | 16 |
| CvB2MT13 | C. viscosissima | 12.7 | 2.1 | 0.9 | 1.5 | 50.7 | 0.5 | 3.1 | 26.0 | nd | nd | 180 | a | 16 |
| CvB2MT14 | C. viscosissima | 3.4 | 0.8 | 1.6 | 0.8 | 52.2 | 0.7 | 14.1 | 26.0 | nd | nd | 110 | a | 16 |
| CvB2MT15 | C. viscosissima | 16.1 | 7.5 | 15.6 | 19.8 | 9.2 | 19.8 | 0.7 | 4.0 | nd | nd | 150 | a | 16 |

TABLE 1-continued

FFA Production Profiles for Various Thioesterases Expressed in *E. coli*. This table provides the mole fractions of various FFAs and total FFA in the cell lysate for enzymes considered in this study as well as those found in literature. Computationally-predicted mutants are named Rx.My, rationally-designed mutants are named RDx.My, and randomly-generated mutants are labeled RM.My, where x is the Round number and y is the Mutant number. Any mutant labeled in this manner derives from this study. Heterologously-expressed and overexpressed thioesterases in *E. coli* are named using their GenBank accession label and mutants from literature (beginning with "CvB2MT", "TE", or "UcFatB") are named as they are in the original source. "nd" indicates that the value was not determined or provided.

| Name | Organism | Fatty Acid Composition (mol %) | | | | | | | | | Total FA ($\mu M$) | Notes | Source |
|---|---|---|---|---|---|---|---|---|---|---|---|---|---|
| | | 8:0 | 10:0 | 12:0 | 12:1 | 14:0 | 14:1 | 16:0 | 16:1 | 18:0 | 18:1 | | | |
| CvB2MT16 | *C. viscosissima* | 15.4 | 5.6 | 3.9 | 9.6 | 22.8 | 30.9 | 0.0 | 7.0 | nd | nd | 310 | a | 16 |
| CvB2MT17 | *C. viscosissima* | 26.2 | 6.5 | 17.6 | 13.5 | 8.6 | 15.8 | 5.0 | 1.6 | nd | nd | 110 | a | 16 |
| CvB2MT18 | *C. viscosissima* | 21.9 | 8.4 | 13.6 | 19.9 | 6.1 | 15.3 | 2.3 | 3.2 | nd | nd | 300 | a | 16 |
| CvB2MT19 | *C. viscosissima* | 18.2 | 6.3 | 10.3 | 22.0 | 8.5 | 18.4 | 0.6 | 6.3 | nd | nd | 170 | a | 16 |
| CvB2MT20 | *C. viscosissima* | 26.2 | 16.9 | 6.6 | 19.1 | 2.4 | 6.2 | 0.3 | 1.4 | nd | nd | 690 | a | 16 |
| CvB2MT21 | *C. viscosissima* | 17.8 | 3.4 | 4.6 | 2.7 | 43.8 | 4.5 | 2.0 | 17.5 | nd | nd | 200 | a | 16 |
| CvB2MT22 | *C. viscosissima* | 20.7 | 9.2 | 13.0 | 15.6 | 8.9 | 16.7 | 0.0 | 10.0 | nd | nd | 85 | a | 16 |
| CvB2MT23 | *C. viscosissima* | 5.6 | 1.0 | 0.8 | 0.8 | 54.2 | 0.9 | 6.6 | 28.7 | nd | nd | 380 | a | 16 |
| CvB2MT24 | *C. viscosissima* | 3.6 | 0.4 | 0.0 | 0.3 | 73.6 | 0.2 | 1.4 | 20.0 | nd | nd | 400 | a | 16 |
| CvB2MT25 | *C. viscosissima* | 28.8 | 9.3 | 13.0 | 15.9 | 5.2 | 13.7 | 2.0 | 0.6 | nd | nd | 290 | a | 16 |
| CvB2MT26 | *C. viscosissima* | 31.7 | 1.2 | 4.8 | 0.0 | 17.9 | 3.9 | 11.3 | 5.7 | nd | nd | 41 | a | 16 |
| CvB2MT27 | *C. viscosissima* | 20.8 | 9.9 | 10.3 | 21.5 | 5.3 | 17.6 | 0.3 | 3.2 | nd | nd | 230 | a | 16 |
| CvB2MT28 | *C. viscosissima* | 17.6 | 5.0 | 7.5 | 3.7 | 40.1 | 4.1 | 3.4 | 14.3 | nd | nd | 330 | a | 16 |
| CvB2MT29 | *C. viscosissima* | 11.4 | 7.2 | 15.0 | 18.1 | 12.1 | 20.5 | 0.4 | 8.9 | nd | nd | 290 | a | 16 |
| CvB2MT30 | *C. viscosissima* | 29.2 | 17.2 | 6.1 | 15.7 | 1.5 | 4.7 | 0.4 | 0.6 | nd | nd | 1000 | a | 16 |
| CvB2MT31 | *C. viscosissima* | 17.9 | 5.9 | 9.0 | 19.6 | 12.1 | 17.3 | 0.7 | 8.1 | nd | nd | 390 | a | 16 |
| CvB2MT32 | *C. viscosissima* | 21.5 | 7.3 | 4.8 | 14.4 | 9.5 | 30.6 | 0.0 | 3.4 | nd | nd | 330 | a | 16 |
| CvB2MT33 | *C. viscosissima* | 27.2 | 7.9 | 9.6 | 20.4 | 5.1 | 12.5 | 0.0 | 3.6 | nd | nd | 570 | a | 16 |
| CvB2MT34 | *C. viscosissima* | 31.8 | 9.6 | 9.2 | 18.4 | 2.8 | 11.2 | 0.3 | 0.4 | nd | nd | 460 | a | 16 |
| CvB2MT35 | *C. viscosissima* | 43.1 | 2.5 | 3.6 | 4.1 | 3.0 | 8.8 | 0.0 | 0.1 | nd | nd | 120 | a | 16 |
| CvB2MT36 | *C. viscosissima* | 40.3 | 0.0 | 2.8 | 0.0 | 2.4 | 0.0 | 0.0 | 0.0 | nd | nd | 47 | a | 16 |
| CvB2MT37 | *C. viscosissima* | 40.2 | 3.4 | 2.8 | 1.0 | 1.1 | 2.0 | 0.0 | 0.2 | nd | nd | 330 | a | 16 |
| CvB2MT38 | *C. viscosissima* | 37.2 | 3.1 | 5.7 | 4.2 | 1.6 | 8.1 | 0.0 | 0.0 | nd | nd | 1000 | a | 16 |
| CvB2MT40 | *C. viscosissima* | 61.4 | 12.5 | 3.3 | 6.2 | 0.6 | 0.9 | 0.0 | 0.0 | nd | nd | 1100 | a | 16 |
| CvB2MT41 | *C. viscosissima* | 36.2 | 3.8 | 1.4 | 0.7 | 0.0 | 0.0 | 0.0 | 0.0 | nd | nd | 93 | a | 16 |
| CvB2MT42 | *C. viscosissima* | 27.0 | 15.0 | 6.9 | 18.9 | 2.6 | 6.1 | 1.5 | 1.1 | nd | nd | 820 | a | 16 |
| CvB2MT43 | *C. viscosissima* | 4.1 | 1.2 | 1.5 | 1.4 | 47.0 | 0.7 | 11.5 | 31.0 | nd | nd | 170 | a | 16 |
| CvB2MT44 | *C. viscosissima* | 22.7 | 23.6 | 7.9 | 24.2 | 1.8 | 4.0 | 0.0 | 0.2 | nd | nd | 710 | a | 16 |
| CvB2MT45 | *C. viscosissima* | 22.5 | 15.8 | 13.1 | 24.4 | 2.6 | 11.4 | 0.0 | 0.0 | nd | nd | 570 | a | 16 |
| CvB2MT47 | *C. viscosissima* | 18.5 | 12.0 | 17.9 | 17.5 | 1.4 | 4.5 | 22.6 | 0.0 | nd | nd | 190 | a | 16 |
| CvB2MT48 | *C. viscosissima* | 13.7 | 38.6 | 6.7 | 17.5 | 0.0 | 3.9 | 0.2 | 0.0 | nd | nd | 140 | a | 16 |
| TEGm157 | Hybrid | 12.0 | 0.7 | 4.0 | 0.5 | 30.9 | 4.6 | 19.1 | 19.2 | nd | 7.6 | 600 | a | 16 |
| TEGm162 | Hybrid | 38.5 | 5.3 | 11.7 | 2.2 | 19.4 | 11.6 | 3.1 | 0.6 | nd | 1.5 | 1700 | a | 16 |
| TEGm169 | Hybrid | 33.7 | 4.6 | 11.7 | 2.8 | 18.8 | 14.6 | 3.8 | 1.9 | nd | 2.7 | 1400 | a | 16 |
| TEGm171 | Hybrid | 17.6 | 0.8 | 6.4 | 3.1 | 26.2 | 5.9 | 12.1 | 23.0 | nd | 2.0 | 1100 | a | 16 |
| TEGm173 | Hybrid | 2.8 | 0.4 | 3.5 | 0.5 | 35.9 | 3.1 | 12.0 | 36.2 | nd | 4.9 | 1200 | a | 16 |
| TEGm181 | Hybrid | 3.7 | 0.7 | 4.8 | 0.5 | 35.5 | 4.6 | 15.1 | 29.2 | nd | 5.0 | 830 | a | 16 |
| TEGm183 | Hybrid | 12.7 | 4.2 | 9.2 | 6.6 | 23.2 | 11.7 | 10.0 | 18.4 | nd | 2.4 | 1200 | a | 16 |
| TEGm198 | Hybrid | 1.3 | 0.1 | 1.4 | 0.1 | 36.4 | 0.7 | 23.0 | 36.6 | nd | 0.0 | 710 | a | 16 |
| TEGm200 | Hybrid | 1.8 | 0.4 | 4.7 | 3.7 | 19.2 | 8.3 | 16.6 | 41.5 | nd | 3.5 | 940 | a | 16 |
| TEGm201 | Hybrid | 1.3 | 0.1 | 1.2 | 0.1 | 19.3 | 1.3 | 28.4 | 41.1 | nd | 7.0 | 590 | a | 16 |
| TEGm202 | Hybrid | 2.8 | 0.3 | 4.0 | 0.8 | 30.1 | 2.9 | 17.9 | 36.4 | nd | 4.0 | 1000 | a | 16 |
| TEGm203 | Hybrid | 0.6 | 0.1 | 2.4 | 0.0 | 45.1 | 2.2 | 24.1 | 19.6 | nd | 5.7 | 530 | a | 16 |
| TEGm204 | Hybrid | 1.3 | 0.1 | 1.6 | 0.3 | 38.0 | 1.5 | 19.8 | 33.6 | nd | 3.4 | 1200 | a | 16 |

TABLE 1-continued

FFA Production Profiles for Various Thioesterases Expressed in *E. coli*. This table provides the mole fractions of various FFAs and total FFA in the cell lysate for enzymes considered in this study as well as those found in literature. Computationally-predicted mutants are named Rx.My, rationally-designed mutants are named RDx.My, and randomly-generated mutants are labeled RM.My, where x is the Round number and y is the Mutant number. Any mutant labeled in this manner derives from this study. Heterologously-expressed and overexpressed thioesterases in *E. coli* are named using their GenBank accession label and mutants from literature (beginning with "CvB2MT", "TE", or "UcFatB") are named as they are in the original source. "nd" indicates that the value was not determined or provided.

| Name | Organism | Fatty Acid Composition (mol %) | | | | | | | | | Total FA (μM) | Notes | Source |
|---|---|---|---|---|---|---|---|---|---|---|---|---|---|
| | | 8:0 | 10:0 | 12:0 | 12:1 | 14:0 | 14:1 | 16:0 | 16:1 | 18:0 | 18:1 | | | |
| TEGm205 | Hybrid | 0.3 | 0.0 | 0.7 | 0.0 | 35.9 | 1.1 | 23.9 | 34.1 | nd | 3.9 | 890 | a | 16 |
| TEGm215 | Hybrid | 9.0 | 0.7 | 5.6 | 1.7 | 30.6 | 6.5 | 15.2 | 24.3 | nd | 3.7 | 980 | a | 16 |
| TEGm219 | Hybrid | 2.4 | 0.3 | 4.4 | 0.2 | 54.7 | 3.8 | 16.1 | 17.5 | nd | 0.0 | 530 | a | 16 |
| TEGm245 | Hybrid | 1.0 | 0.0 | 0.7 | 0.0 | 32.1 | 0.0 | 27.7 | 38.5 | nd | 0.0 | 1100 | a | 16 |
| TEGm250 | Hybrid | 20.0 | 4.3 | 3.8 | 2.0 | 19.8 | 3.5 | 19.1 | 17.1 | nd | 6.2 | 1600 | a | 16 |
| TEGm258 | Hybrid | 50.4 | 6.4 | 4.7 | 1.8 | 9.1 | 1.3 | 10.2 | 1.9 | nd | 2.3 | 1600 | a | 16 |
| TEGm288 | Hybrid | 30.9 | 5.5 | 9.8 | 8.5 | 12.9 | 7.1 | 12.1 | 8.3 | nd | 2.2 | 1300 | a | 16 |
| TEGm413 | Hybrid | 14.8 | 6.6 | 13.6 | 7.6 | 14.2 | 5.9 | 14.7 | 16.9 | nd | 3.9 | 1100 | a | 16 |
| TEGm419 | Hybrid | 13.2 | 7.6 | 13.7 | 12.2 | 15.2 | 8.0 | 8.9 | 15.2 | nd | 3.6 | 1400 | a | 16 |
| TEGm492 | Hybrid | 2.5 | 1.5 | 8.6 | 0.0 | 21.9 | 2.8 | 25.7 | 24.0 | nd | 12.5 | 600 | a | 16 |
| TEGm501 | Hybrid | 0.4 | 0.4 | 9.1 | 1.0 | 38.7 | 4.9 | 17.1 | 23.7 | nd | 4.6 | 870 | a | 16 |
| TEGm520 | Hybrid | 2.4 | 3.1 | 8.8 | 10.3 | 24.0 | 15.0 | 11.4 | 20.6 | nd | 2.8 | 1000 | a | 16 |
| TEGm546 | Hybrid | 1.3 | 5.2 | 21.1 | 7.1 | 22.1 | 11.7 | 14.9 | 12.2 | nd | 3.4 | 610 | a | 16 |
| UcFatB-M1 | *U. californica* | nd | nd | nd | nd | 29 ± 3 | nd | 24 ± 3 | 32 ± 2 | 10 ± 1 | 5.3 ± 0.8 | 140 ± 10 | b | 17 |
| UcFatB-M2 | *U. californica* | nd | nd | nd | nd | 33 ± 4 | nd | 24 ± 3 | 27 ± 2 | 9.9 ± 0.8 | 5.6 ± 0.5 | 105 ± 10 | b | 17 |
| UcFatB-M3 | *U. californica* | nd | nd | nd | nd | 33 ± 1 | nd | 32.7 ± 0.6 | 21 ± 1 | 8.4 ± 0.4 | 5.8 ± 0.4 | 111 ± 4 | b | 17 |
| UcFatB-M4 | *U. californica* | nd | nd | nd | nd | 15.4 ± 0.6 | nd | 21 ± 4 | 46 ± 1 | 16 ± 4 | 1.0 ± 0.4 | 53 ± 4 | b | 17 |
| UcFatB-M5 | *U. californica* | nd | nd | nd | nd | 11.1 ± 0.9 | nd | 42 ± 6 | 6 ± 2 | 41 ± 4 | 0.4 ± 0.4 | 24 ± 2 | b | 17 |
| UcFatB-M6 | *U. californica* | nd | nd | nd | nd | 12.9 ± 0.9 | nd | 44 ± 4 | 8.9 ± 0.6 | 34 ± 3 | 0.9 ± 0.9 | 33 ± 3 | b | 17 |
| UcFatB-M7 | *U. californica* | nd | nd | nd | nd | 12 ± 2 | nd | 45 ± 6 | 10 ± 1 | 30 ± 4 | 2.6 ± 0.5 | 38 ± 4 | b | 17 |
| UcFatB-M8 | *U. californica* | nd | nd | nd | nd | 12 ± 2 | nd | 41 ± 5 | 7 ± 1 | 39 ± 3 | 0.6 ± 0.6 | 33 ± 3 | b | 17 | a Standard deviation not determined or provided; total FFA values with unknown standard deviation was reported to two significant figures
b Data approximated using image processing software
c Mole-based values not provided and incapable of being calculated; mass-based values used instead
d 16:0 and 16:1 fatty acid compositions combined 1 Jing F Y, et al. (2011) "Phylogenetic and experimental characterization of an acyl-ACP thioesterase family reveals significant diversity in enzymatic specificity and activity," *BMC Biochem* 12.
2 Dormann P, et al. (1995) "Cloning and Expression in *Escherichia-Coli* of a Novel Thioesterase from *Arabidopsis-Thaliana* Specific for Long-Chain Acyl-Acyl Carrier Proteins," *Arch Biochem Biophys* 316(1): 612-618.
3 Ghosh S K, et al. (2007) "Characterization and cloning of a stearoyl/oleoyl specific fatty acyl-acyl carrier protein thioesterase from the seeds of *Madhuca longifolia (latifolia),*" *Plant Physiol Bioch* 45(12): 887-897.
4 Jha J K, et al. (2006) "Cloning and functional expression of an acyl-ACP thioesterase FatB type from *Diplokrema (Madhuca) butyracea* seeds in *Escherichia coli,*" *Plant Physiol Bioch* 44(11-12): 645-655.
5 Dong S B, et al. (2014) "Cloning, characterization, and expression analysis of acyl-acyl carrier protein (ACP)-thioesterase B from seeds of Chinese Spicehush (*Lindera communis*)," *Gene* 542(1): 16-22.
6 Steen E J, et al. (2010) "Microbial production of fatty-acid-derived fuels and chemicals from plant biomass," *Nature* 463(7280): 559-U182.
7 Lu X, et al. (2008) "Overproduction of free fatty acids in *E. coli*: implications for biodiesel production," *Metabolic engineering* 10(6): 333-339.
8 Voelker T A & Davies H M (1994) "Alteration of the specificity and regulation of fatty acid synthesis of *Escherichia coli* by expression of a plant medium-chain acyl-acyl carrier protein thioesterase," *J Bacteriol* 176(23): 7320-7327.
9 Chen G, et al. (2012) "Cloning of acyl-ACP thioesterase FatA from *Arachis hypogaea* L. and its expression in *Escherichia coli,*" *Journal of biomedicine & biotechnology* 2012: 652579.
10 Zhang X, et al. (2011) "Efficient free fatty acid production in *Escherichia coli* using plant acyl-ACP thioesterases," *Metabolic engineering* 13(6): 713-722.
11 Zheng Y, et al. (2012) "Boosting the free fatty acid synthesis of *Escherichia coli* by expression of a cytosolic *Acinetobacter baylyi* thioesterase," *Biotechnology for biofuels* 5(1): 76.
12 Jing F Y, et al. (2007) "Functional expression of an acyl carrier protein (ACP) from *Azospirillum brasilense* alters fatty acid profiles in *Escherichia coli* and *Brassica juncea,*" *Plant physiology and biochemistry: PPB/Societe francaise de physiologie vegetale* 45(6-7): 490-500.
13 Gong Y, et al. (2011) "Characterization of a novel thioesterase (PtTE) from *Phaeodactylum tricornutum,*" *Journal of basic microbiology* 51(6): 666-672.
14 Serrano-Vega M J, et al. (2005) "Cloning, characterization and structural model of a FatA-type thioesterase from sunflower seeds (*Helianthus annuus* L.)," *Planta* 221(6): 868-880.
15 Lee S, et al. (2014) "Enhanced free fatty acid production by codon-optimized *Lactococcus lactis* acyl-ACP thioesterase gene expression in *Escherichia coli* using crude glycerol," *Enzyme and microbial technology* 67: 8-16.
16 Jing F (2013) "Characterization of acyl-ACP thioesterases for the purpose of diversifying fatty acid synthesis pathway," Dissertation/Thesis (ProQuest Dissertations Publishing).
17 Mayer K M & Shanklin J (2007) "Identification of amino acid residues involved in substrate specificity of plant acyl-ACP thioesterases using a bioinformatics-guided approach," *Bmc Plant Biol* 7.

TABLE 2

Sequences of All Enzymes Considered in This Study. Mutant names are provided in the same format as described for Table S1. Changes indicates the number of amino acid changes, or whether a frameshift or truncation occurred for the mutant. Amino acid substitutions are provided in the format XyZ, where X is the WT residue at position y and Z is the new amino acid. "stop" indicates a stop codon replaces the existing amino acid, resulting in a shorter peptide (a truncation). A frameshift indicates that a WT amino acid was eradicated and not replaced by a different residue.

| Name | Changes | Mutations |
|---|---|---|
| R1.M1 | 1 | Y145K |
| R1.M2 | 1 | L11G |
| R1.M3 | 3 | L11G, I107K, R108K |
| R1.M4 | 4 | L11G, L76K, I107K, R108K |
| R1.M5 | 5 | L11G, L76K, I107K, R108K, F139E |
| R1.M6 | 6 | L11G, L76K, I107K, R108K, F139E, Y145R |
| R1.M7 | 6 | L11G, L76K, I107K, R108K, F139E, Y145K |
| R1.M8 | 7 | L11G, L76K, I107K, R108K, A111E, F139E, Y145R |
| R1.M9 | 5 | I107K, R108K, A111E, F139E, Y145R |
| R1.M10 | 7 | L11G, L76K, I107K, R108K, A111E, F139E, Y145K |
| R1.M11 | 5 | I107K, R108K, A111E, F139E, Y145K |
| R1.M12 | 5 | I107K, R108K, A111E, F139H, Y145K |
| R2.M1 | 3 | G72F, F139W, Y145F |
| R2.M2 | 7 | G72L, F139P, M141W, E142P, Y145F, G155A, I156L |
| R2.M3 | 5 | L11W, G72F, F139W, E142P, Y145F |
| R2.M4 | 7 | G72L, F139P, M141W, E142P, Y145P, G155W, I156L |
| R2.M5 | 2 | E142P, Y145F |
| R2.M6 | 4 | L11F, G72F, F139M, Y145F |
| R2.M7 | 4 | G72F, Y145F, G155W, I156L |
| R2.M8 | 7 | G72L, F139P, M141W, E142P, Y145P, G155A, I156L |
| R2.M9 | 5 | L11F, G72F, F139W, E142P, Y145F |
| R2.M10 | 6 | G72L, F139P, M141W, E142P, G155A, I156L |
| R2.M11 | 2 | L11P, Y145F |
| R2.M12 | 4 | L11F, G72F, F139W, Y145F |
| R2.M13 | 2 | G72F, Y145F |
| R2.M14 | 3 | G72A, E142P, Y145P |
| R2.RD1 | 1 | G72A |
| R2.RD2 | 1 | G72L |
| R2.RD3 | 1 | L11P |
| R2.RD4 | 2 | L11P, G72F |
| R2.RD5 | 1 | L11W |
| R3.M1 | 3 | S122K, Y145K, L146K |
| R3.M2 | 1 | M141L |
| R3.M3 | 4 | I107L, R108K, Y145K, L146K |
| R3.M4 | 3 | M141L, Y145K, L146K |
| R3.M5 | 5 | I107K, R108F, L109I, Y145K, L146K |
| R3.M6 | 1 | R108K |
| R3.M7 | 2 | Y145K, L146K |
| R3.M8 | 2 | S122K, Y145K |
| R3.M9 | 3 | S122L, Y145K, L146K |
| R3.M10 | 4 | S122K, M141K, Y145K, L146K |
| R3.RD1 | 2 | I107L, R108K |
| R3.RD2 | 3 | I107K, R108F, L109I |
| R3.RD3 | 1 | S122K |
| R3.RD4 | 1 | S122L |
| R3.RD5 | 2 | E142P, Y145K |
| R4.M1 | 3 | I107M, R108F, E142P |
| R4.M2 | 3 | M141L, E142P, Y145F |
| R4.M3 | 2 | S122M, E142P |
| R4.M4 | 1 | E142P |
| R4.M5 | 4 | S122M, M141L, E142P, Y145F |
| R4.M6 | 2 | E142P, Y145F |
| R4.M7 | 1 | I107G |
| R4.M8 | 1 | M141G |
| R4.M9 | 1 | I107K |
| R4.M10 | 3 | R108F, L109F, E142P |
| R4.M11 | 4 | R108F, L109F, S122I, E142P |
| R4.M12 | 4 | R108F, L109F, M141L, Y145F |
| R4.M13 | 5 | R108F, L109F, S122M, Y145F, L146P |
| R4.M14 | 3 | R108F, Y145F, L146P |
| R4.M15 | 3 | R108F, L109F, Y145F |
| R4.M16 | 3 | R108K, L109I, L146K |
| R4.M17 | 3 | R108F, L109F, S122M |
| R4.M18 | 2 | R108F, L109F |
| R4.RD1 | 2 | M141L, E142P |
| R4.RD2 | 2 | M141L, Y145K |
| R4.RD3 | 4 | M141L, E142P, Y145K, L146K |
| R4.RD4 | 3 | R108F, L109F, M141L |
| R4.RD5 | 6 | R108F, L109F, M141L, E142P, Y145K, L146K |
| R4.RD6 | 5 | R108F, L109F, M141L, Y145K, L146K |
| R4.RD7 | 1 | H157A |
| R4.RD8 | 2 | I107M, R108F |
| R4.RD9 | 1 | R108F |
| R4.RD10 | 1 | S122I |
| R4.RD11 | 1 | S122M |
| RM.M1 | 2 | S36T, P110T |
| RM.M2 | 1 | L146I |
| RM.M3 | 2 | A19S, A98P |
| RM.M4 | 3 | Q49H, M105K, D161N |
| RM.M5 | truncation | G8C, M105L, Y117stop |
| RM.M6 | 1 | P110S |
| RM.M7 | 1 | L57P |
| RM.M8 | 1 | A123T |
| RM.M9 | 3 | G72V, D74N, F79Y |
| RM.M10 | 1 | Q93H |
| RM.M11 | truncation | Q106stop |
| RM.M12 | 1 | P158H |
| RM.M13 | 2 | S41N, A162V |
| RM.M14 | 1 | P148S |
| RM.M15 | 2 | F121Y, P126L |
| RM.M16 | 1 | R64H |
| RM.M17 | 2 | P102A, A111V |
| RM.M18 | 2 | F79Y, Q82H |
| RM.M19 | 1 | L57Q |
| RM.M20 | 2 | A22T, A129T |
| RM.M21 | 1 | L136P |
| RM.M22 | 3 | T3M, M17I, E69G |
| RM.M23 | truncation | W33stop |
| RM.M24 | frameshift | Q90single nucleotide deletion |
| RM.M25 | 2 | G44C, A56T |
| RM.M26 | frameshift | A25T, frameshift after K127 |
| RM.M27 | 1 | S12I |
| RM.M28 | 3 | W23C, V68L, G75S |
| RM.M29 | 3 | V38F, F139Y, Y145C |
| RM.M30 | 2 | A22V, A171V |
| RM.M31 | 4 | L109P, Y117N, A123V, K147E |
| RM.M32 | 2 | N28K, A123V |
| RM.M33 | frameshift | G8V frameshift resulting in stop codon at 10$^{th}$ amino acid position |
| RM.M34 | 1 | P55L |
| RM.M35 | 2 | S41G, L92M |
| RM.M36 | 2 | S47P, M170I |
| RM.M37 | 1 | P135S |
| RM.M38 | 1 | A25P |
| RM.M39 | 2 | T35S, E142D |
| RM.M40 | 4 | L92S, V95I, E101D, W169L |
| RM.M41 | 1 | L92S |
| RM.M42 | 5 | I42V, G75A, Q106R, A111G, P138S |
| RM.M43 | 1 | L67M |
| RM.M44 | 1 | A120V |
| RM.M45 | truncation | E69stop |
| RM.M46 | truncation | E119stop |
| RM.M47 | 1 | S41N |
| RM.M48 | 1 | L58R |
| RM.M49 | truncation | A19T, W31stop |
| RM.M50 | 3 | M105K, R115C, P135del |
| RM.M51 | truncation | truncation one nucleotide after A40 resulting also in frameshift |
| RM.M52 | 2 | M170I, A171V |
| RM.M53 | 1 | W150L |

TABLE 2-continued

Sequences of All Enzymes Considered in This Study. Mutant names are provided in the same format as described for Table S1. Changes indicates the number of amino acid changes, or whether a frameshift or truncation occurred for the mutant. Amino acid substitutions are provided in the format XyZ, where X is the WT residue at position y and Z is the new amino acid. "stop" indicates a stop codon replaces the existing amino acid, resulting in a shorter peptide (a truncation). A frameshift indicates that a WT amino acid was eradicated and not replaced by a different residue.

| Name | Changes | Mutations |
|---|---|---|
| RM.M54 | 2 | A25T, S41I |
| RM.M55 | 2 | P135T, D161N |
| RM.M56 | 1 | D2V |
| RM.M57 | 2 | A111T, M141I |
| RM.M58 | 1 | G155D |
| RM.M59 | 1 | R108C |
| RM.M60 | 1 | T46I |
| RM.M61 | 1 | E101V |

TABLE 3

Fatty acid production profiles for $C_{12}$-specific random variants and their constituent point mutations. This table provides the mole fractions of $C_8$-C18 FFAs and total FFA in the cell lysate for RM.M39 and RM.M57 (the two C12-specific RM variants) as well as the individual amino acid substitutions.

| Name | Fatty Acid Composition (mol %) | | | | | | | | | | Total FFA |
|---|---|---|---|---|---|---|---|---|---|---|---|
| | 8:0 | 10:0 | 12:0 | 12:1 | 14:0 | 14:1 | 16:0 | 16:1 | 18:0 | 18:1 | |
| WT | 5.9 ± 0.3 | 1.09 ± 0.06 | 20 ± 1 | 7.5 ± 0.5 | 29 ± 2 | 7.1 ± 0.4 | 14.2 ± 0.8 | 11.6 ± 0.8 | 0.22 ± 0.01 | 2.1 ± 0.1 | 1900 ± 50 |
| | 2.7 ± 0.9 | 0.9 ± 0.1 | 16 ± 4 | 6 ± 2 | 28 ± 7 | 6 ± 2 | 21 ± 7 | 17 ± 2 | 0.3 ± 0.1 | 2.3 ± 0.4 | 1600 ± 200 |
| E142D | 5.5 ± 0.7 | 2.5 ± 0.2 | 33 ± 3 | 12 ± 1 | 26 ± 2 | 6.1 ± 0.6 | 5.7 ± 0.8 | 8.1 ± 0.8 | 0.14 ± 0.04 | 1.2 ± 0.1 | 3000 ± 100 |
| RM.M39 | 6 ± 2 | 2.5 ± 0.4 | 32 ± 6 | 12 ± 2 | 26 ± 6 | 6 ± 1 | 6.4 ± 0.6 | 8 ± 2 | 0.10 ± 0.01 | 1.2 ± 0.3 | 2800 ± 200 |
| A111T | 4 ± 2 | 1.0 ± 0.1 | 15 ± 3 | 6 ± 1 | 25 ± 5 | 6 ± 1 | 23 ± 3 | 17 ± 3 | 0.35 ± 0.06 | 2.2 ± 0.4 | 1140 ± 80 |
| M141I | 4 ± 2 | 2.5 ± 0.3 | 17 ± 4 | 14 ± 3 | 21 ± 4 | 3.8 ± 0.9 | 20 ± 2 | 14 ± 2 | 0.32 ± 0.04 | 2.2 ± 0.3 | 1200 ± 80 |
| RM.M57 | 5 ± 1 | 2.9 ± 0.7 | 17 ± 4 | 14 ± 4 | 21 ± 4 | 3.8 ± 1.0 | 20 ± 2 | 13 ± 1 | 0.33 ± 0.05 | 2.1 ± 0.3 | 1400 ± 100 |

TABLE 4

'TesA residues sorted by distance from acyl-ACP for design position selection. Design positions were selected from each round using the eight closest residues that were not excluded from consideration. The method used to sort by distance varied between R1-R2 and R3- R4. The sorted list is provided in the table. Residues are labeled by their WT amino acid followed by the position of the residue. Residues that were excluded from design position consideration were annotated. The distance used to sort the residues is provided within parentheses. Thus, the eight highest ranked residues that were not annotated (i.e., excluded) formed the set of design positions employed within IPRO.

| Rank | R1[a] | R2[a] | R3-R4[b] |
|---|---|---|---|
| 1 | Y145 (1.83 Å) | Y145 (1.83 Å) | P110[k] (1.83 Å) |
| 2 | L109[f,h] (2.70 Å) | L109[f] (2.70 Å) | Y145 (2.70 Å) |
| 3 | P110[e] (2.77 Å) | P110[e] (2.77 Å) | R108 (2.77 Å) |
| 4 | R108 (3.02 Å) | R108[i] (3.02 Å) | M141 (3.02 Å) |
| 5 | N73[d,g,h] (3.08 Å) | N73[d,g] (3.08 Å) | A111[l] (3.08 Å) |
| 6 | S10[c,d,g] (3.25 Å) | S10[c,d,g] (3.25 Å) | L109 (3.25 Å) |
| 7 | G44[d,g,h] (3.33 Å) | G44[d,g] (3.33 Å) | I156[k] (3.33 Å) |
| 8 | D9[g] (3.47 Å) | D9[g] (3.47 Å) | E142 (3.47 Å) |
| 9 | L11 (3.71 Å) | L11 (3.71 Å) | G155[k] (3.71 Å) |
| 10 | A111 (3.72 Å) | A111[i] (3.72 Å) | F139[k] (3.72 Å) |
| 11 | G72 (3.81 Å) | G72 (3.81 Å) | N112[k,l] (3.81 Å) |
| 12 | L76 (3.86 Å) | L76[j] (3.86 Å) | Y113[k,l] (3.86 Å) |
| 13 | H157[c,h] (3.99 Å) | H157[c] (3.99 Å) | V144[k] (3.99 Å) |
| 14 | I156[h] (4.21 Å) | I156 (4.21 Å) | N118[l] (4.21 Å) |
| 15 | F139 (4.37 Å) | F139 (4.37 Å) | I107 (4.37 Å) |
| 16 | S43[g] (4.37 Å) | S43[g] (4.37 Å) | M151[k,l] (4.37 Å) |
| 17 | D45[g] (4.82 Å) | D45[g] (4.82 Å) | L76[k] (4.82 Å) |
| 18 | I107 (4.83 Å) | I107[i] (4.83 Å) | G72[k] (4.83 Å) |
| 19 | G155 (5.01 Å) | G155 (5.01 Å) | L146 (5.01 Å) |
| 20 | I42[g,h] (5.14 Å) | I42[g] (5.14 Å) | H157[k] (5.14 Å) |
| 21 | E142[h] (5.53 Å) | E142 (5.53 Å) | S122 (5.53 Å) |
| 22 | M141 (5.56 Å) | M141 (5.56 Å) | D154[k] (5.56 Å) |
| 23 | E69 (5.62 Å) | E69 (5.62 Å) | P158[k] (5.62 Å) |
| 24 | Y15 (5.96 Å) | Y15 (5.96 Å) | L11[k] (5.96 Å) |
| 25 | N112 (5.98 Å) | N112[j] (5.98 Å) | E143 (5.98 Å) |
| 26 | G71 (6.15 Å) | G71 (6.15 Å) | F121[k] (6.15 Å) |
| 27 | M151 (6.22 Å) | M151 (6.22 Å) | G75[k] (6.22 Å) |
| 28 | N118 (6.23 Å) | N118[j] (6.23 Å) | F140[k] (6.23 Å) |
| 29 | S12 (6.43 Å) | S12 (6.43 Å) | G114[k,l] (6.43 Å) |
| 30 | F121 (6.66 Å) | F121 (6.66 Å) | Q106 (6.66 Å) |
| 31 | Y113 (6.67 Å) | Y113[j] (6.67 Å) | P148[l] (6.67 Å) |
| 32 | G75 (6.97 Å) | G75j (6.97 Å) | Q152k,l (6.97 Å) |
| 33 | G8 (6.99 Å) | G8 (6.99 Å) | W150l (6.99 Å) |
| 34 | P158e (7.02 Å) | P158e (7.02 Å) | K147l (7.02 Å) |
| 35 | D74 (7.06 Å) | D74 (7.06 Å) | Y117k,l (7.06 Å) |
| 36 | T46h (7.12 Å) | T46 (7.12 Å) | P138k (7.12 Å) |
| 37 | G14h (7.56 Å) | G14 (7.56 Å) | G71k (7.56 Å) |
| 38 | A13 (7.56 Å) | A13 (7.56 Å) | R115l (7.56 Å) |
| 39 | L70h (7.67 Å) | L70 (7.67 Å) | N73k (7.67 Å) |
| 40 | D154c (7.87 Å) | D154c (7.87 Å) | A162k (7.87 Å) |
| 41 | S122 (8.22 Å) | S122 (8.22 Å) | S10k (8.22 Å) |
| 42 | R77h (8.22 Å) | R77j (8.22 Å) | M105 (8.22 Å) |
| 43 | V144 (8.32 Å) | V144 (8.32 Å) | E119l (8.32Å) |
| 44 | Q49 (8.38 Å) | Q49 (8.38 Å) | Y15k (8.38 Å) |
| 45 | Q106 (8.41 Å) | Q106 (8.41 Å) | Y125k (8.41 Å) |
| 46 | F140h (8.41Å) | F140 (8.41 Å) | D9k (8.41 Å) |
| 47 | S41 (8.51 Å) | S41 (8.51 Å) | D153l (8.51 Å) |
| 48 | Y125 (8.55 Å) | Y125 (8.55 Å) | E69k (8.55 Å) |
| 49 | L146h (8.61 Å) | L146 (8.61 Å) | G78k (8.61 Å) |
| 50 | E143h (8.76 Å) | E143 (8.76 Å) | D74k (8.76 Å) |

TABLE 4-continued

'TesA residues sorted by distance from acyl-ACP for design position selection. Design positions were selected from each round using the eight closest residues that were not excluded from consideration. The method used to sort by distance varied between R1-R2 and R3-R4. The sorted list is provided in the table. Residues are labeled by their WT amino acid followed by the position of the residue. Residues that were excluded from design position consideration were annotated. The distance used to sort the residues is provided within parentheses. Thus, the eight highest ranked residues that were not annotated (i.e., excluded) formed the set of design positions employed within IPRO.

| Rank | R1[a] | R2[a] | R3-R4[b] |
|---|---|---|---|
| 51 | M105 (9.31 Å) | M105 (9.31 Å) | I166k (9.31 Å) |
| 52 | S47 (9.35 Å) | S47 (9.35 Å) | N159k (9.35Å) |
| 53 | R16 (9.41 Å) | R16 (9.41 Å) | R77k (9.41 Å) |
| 54 | G114h (9.51 Å) | G114j (9.51 Å) | I124 (9.51 Å) |
| 55 | Q152 (9.75 Å) | Q152 (9.75 Å) | A120 (9.75 Å) |
| 56 | Y117 (9.76 Å) | Y117j (9.76 Å) | Q149l (9.76 Å) |
| 57 | R53 (9.87 Å) | R53 (9.87 Å) | A123 (9.87 Å) |
| 58 | W23 (10.13 Å) | W23 (10.13 Å) | L70k (10.13 Å) |
| 59 | G78 (10.15 Å) | G78j (10.15 Å) | L137 (10.15 Å) |
| 60 | E119h (10.41 Å) | E119j (10.41 Å) | S12k (10.41 Å) |
| 61 | L7h (10.46 Å) | L7 (10.46 Å) | P81k (10.46 Å) |
| 62 | K147h (10.68 Å) | K147 (10.68 Å) | R116l (10.68 Å) |
| 63 | R115h (10.78 Å) | R115j (10.78 Å) | G44k (10.78 Å) |
| 64 | G50 (10.89 Å) | G50 (10.89 Å) | W169 (10.89 Å) |
| 65 | T84 (11.10 Å) | T84 (11.10 Å) | G14k (11.10 Å) |
| 66 | M17 (11.11 Å) | M17 (11.11 Å) | T84 (11.11 Å) |
| 67 | A40h (11.16 Å) | A40 (11.16 Å) | F165 (11.16 Å) |
| 68 | Q163 (11.17 Å) | Q163 (11.17 Å) | F79 (11.17 Å) |
| 69 | W150 (11.31 Å) | W150 (11.31 Å) | G8k (11.31 Å) |
| 70 | I166 (11.32 Å) | I166 (11.32 Å) | S43k (11.32 Å) |
| 71 | D153h (11.33 Å) | D153 (11.33 Å) | P126 (11.33 Å) |
| 72 | N39 (11.41 Å) | N39 (11.41 Å) | W23k (11.41 Å) |
| 73 | N159 (11.42 Å) | N159 (11.42 Å) | L136k (11.42 Å) |
| 74 | F79 (11.44 Å) | F79j (11.44 Å) | S47 (11.44 Å) |
| 75 | A22 (11.51 Å) | A22 (11.51 Å) | Q163k (11.51 Å) |
| 76 | V68 (11.54 Å) | V68 (11.54 Å) | T46k (11.54 Å) |
| 77 | P148e (11.59 Å) | P148e (11.59 Å) | R16l (11.59 Å) |
| 78 | P138e (11.67 Å) | P138e (11.67 Å) | M170 (11.67 Å) |
| 79 | Q48 (11.69 Å) | Q48 (11.69 Å) | D161 (11.69 Å) |
| 80 | I6 (11.72 Å) | I6 (11.72 Å) | L104k (11.72 Å) |
| 81 | L88 (12.02 Å) | L88 (12.02 Å) | A13k (12.02 Å) |
| 82 | P24e (12.16 Å) | P24e (12.16 Å) | D45k (12.16 Å) |
| 83 | I124 (12.31 Å) | I124 (12.31 Å) | Q173 (12.31 Å) |
| 84 | R116h (12.66 Å) | R116j (12.66 Å) | S41k (12.66 Å) |
| 85 | A123h (12.68 Å) | A123 (12.68 Å) | A22 (12.68 Å) |
| 86 | A120 (12.69 Å) | A120j (12.69 Å) | V68 (12.69 Å) |
| 87 | L137 (13.07 Å) | L137 (13.07 Å) | L88k (13.07 Å) |
| 88 | L67 (13.19 Å) | L67 (13.19 Å) | R160 (13.19 Å) |
| 89 | L51 (13.27 Å) | L51 (13.27 Å) | M17l (13.27 Å) |
| 90 | A162 (13.28 Å) | A162 (13.28 Å) | E85 (13.28 Å) |
| 91 | L104 (13.37 Å) | L104 (13.37 Å) | L67 (13.37 Å) |
| 92 | S18h (13.41 Å) | S18 (13.41 Å) | A129k (13.41 Å) |
| 93 | W169 (13.43 Å) | W169 (13.43 Å) | K127 (13.43 Å) |
| 94 | P81e (13.54 Å) | P81e (13.54 Å) | Q80 (13.54 Å) |
| 95 | A19 (13.56 Å) | A19 (13.56 Å) | A167k (13.56 Å) |
| 96 | Q149h (13.56 Å) | Q149 (13.56 Å) | L128k (13.56 Å) |
| 97 | M170 (13.69 Å) | M170 (13.69 Å) | P24k (13.69 Å) |
| 98 | I91 (13.76 Å) | I91 (13.76 Å) | I6 (13.76 Å) |
| 99 | R160h (13.90 Å) | R160 (13.90 Å) | I42 (13.90 Å) |
| 100 | L136 (14.23 Å) | L136 (14.23 Å) | D168 (14.23 Å) |
| 101 | Q80h (14.28 Å) | Q80j (14.28 Å) | P164 (14.28 Å) |
| 102 | P126e (14.42 Å) | P126e (14.42 Å) | L7k (14.42 Å) |
| 103 | A21 (14.45 Å) | A21 (14.45 Å) | L103k (14.45 Å) |
| 104 | T87 (14.46 Å) | T87 (14.46 Å) | Q83 (14.46 Å) |
| 105 | E85 (14.64 Å) | E85 (14.64 Å) | T87 (14.64 Å) |
| 106 | A52 (15.04 Å) | A52 (15.04 Å) | K172 (15.04 Å) |
| 107 | L103 (15.26 Å) | L103 (15.26 Å) | G50k (15.26 Å) |
| 108 | L57 (15.37 Å) | L57 (15.37 Å) | Q49 (15.37 Å) |
| 109 | Q83 (15.58 Å) | Q83 (15.58 Å) | Q82 (15.58 Å) |
| 110 | L128 (15.59 Å) | L128 (15.59 Å) | A21 (15.59 Å) |
| 111 | A25 (15.64 Å) | A25 (15.64 Å) | P135 (15.64 Å) |
| 112 | V38h (15.71 Å) | V38 (15.71 Å) | L174k (15.71 Å) |
| 113 | S20h (15.81 Å) | S20 (15.81 Å) | Q48 (15.81 Å) |
| 114 | L5 (16.02 Å) | L5 (16.02 Å) | L27k (16.02 Å) |
| 115 | A167h (16.03 Å) | A167 (16.03 Å) | N39k (16.03 Å) |
| 116 | Q82h (16.04 Å) | Q82 (16.04 Å) | L26k (16.04 Å) |
| 117 | L54 (16.11 Å) | L54 (16.11 Å) | I91k (16.11 Å) |
| 118 | D161 (16.25 Å) | D161 (16.25 Å) | A171 (16.25 Å) |
| 119 | V66 (16.52 Å) | V66 (16.52 Å) | V134l (16.52 Å) |
| 120 | F165 (16.57 Å) | F165 (16.57 Å) | K130 (16.57 Å) |
| 121 | L92 (16.80 Å) | L92 (16.80 Å) | A191 (16.80 Å) |
| 122 | P164e,h (16.88 Å) | P164e (16.88 Å) | Q86 (16.88 Å) |
| 123 | Q173 (17.03 Å) | Q173 (17.03 Å) | L51k (17.03 Å) |
| 124 | V37 (17.04 Å) | V37 (17.04 Å) | A25k (17.04 Å) |
| 125 | Q86h (17.06 Å) | Q86 (17.06 Å) | L92 (17.06 Å) |
| 126 | R89 (17.23 Å) | R89 (17.23 Å) | A40k (17.23 Å) |
| 127 | L26 (17.38 Å) | L26 (17.38 Å) | P102 (17.38 Å) |
| 128 | P135e (17.51 Å) | P135e (17.51 Å) | R89 (17.51 Å) |
| 129 | K127 (17.53 Å) | K127 (17.53 Å) | V66k (17.53 Å) |
| 130 | L27 (17.66 Å) | L27 (17.66 Å) | L177 (17.66 Å) |
| 131 | L174 (17.80 Å) | L174 (17.80 Å) | S181 (17.80 Å) |
| 132 | L4 (18.13 Å) | L4 (18.13 Å) | E131 (18.13 Å) |
| 133 | A129 (18.20 Å) | A129 (18.20 Å) | V37k (18.20 Å) |
| 134 | D168 (18.62 Å) | D168 (18.62 Å) | F132l (18.62 Å) |
| 135 | P55e (18.88 Å) | P55e (18.88 Å) | L4 (18.88 Å) |
| 136 | A171h (18.95 Å) | A171 (18.95 Å) | R53k (18.95 Å) |
| 137 | V95 (19.03 Å) | V95 (19.03 Å) | L5k (19.03 Å) |
| 138 | P102e (19.14 Å) | P102e (19.14 Å) | Q175 (19.14 Å) |
| 139 | Q90 (19.20 Å) | Q90 (19.20 Å) | L54k (19.20 Å) |
| 140 | V134 (19.34 Å) | V134 (19.34 Å) | P176 (19.34 Å) |
| 141 | N28 (19.46 Å) | N28 (19.46 Å) | Q90 (19.46 Å) |
| 142 | H61 (19.60 Å) | H61 (19.60 Å) | S20l (19.60 Å) |
| 143 | W65 (19.67 Å) | W65 (19.67 Å) | W65 (19.67 Å) |
| 144 | L177 (20.06 Å) | L177 (20.06 Å) | A52 (20.06 Å) |
| 145 | Q60 (20.07 Å) | Q60 (20.07 Å) | V95 (20.07 Å) |
| 146 | D94 (20.41 Å) | D94 (20.41 Å) | N28 (20.41 Å) |
| 147 | A56 (20.42 Å) | A56 (20.42 Å) | K30l (20.42 Å) |
| 148 | L58 (20.50 Å) | L58 (20.50 Å) | V38 (20.50 Å) |
| 149 | K172 (20.68 Å) | K172 (20.68 Å) | V178 (20.68 Å) |
| 150 | K130 (20.74 Å) | K130 (20.74 Å) | D133l (20.74 Å) |
| 151 | E101 (20.91 Å) | E101 (20.91 Å) | D29l (20.91 Å) |
| 152 | W31 (20.95 Å) | W31j (20.95 Å) | E101 (20.95 Å) |
| 153 | F132 (21.00 Å) | F132 (21.00 Å) | L57 (21.00 Å) |
| 154 | S36 (21.31 Å) | S36 (21.31 Å) | W31l (21.31 Å) |
| 155 | Q93 (21.32 Å) | Q93 (21.32 Å) | D94 (21.32 Å) |
| 156 | P63e (21.42 Å) | P63e (21.42 Å) | Q93 (21.42 Å) |
| 157 | D29 (21.54 Å) | D29 (21.54 Å) | P63k (21.54 Å) |
| 158 | T3 (21.67 Å) | T3 (21.67 Å) | A100k (21.67 Å) |
| 159 | E131 (21.97 Å) | E131 (21.97 Å) | T35 (21.97 Å) |
| 160 | K30 (22.18 Å) | K30 (22.18 Å) | K96 (22.18 Å) |
| 161 | Q175 (22.37 Å) | Q175 (22.37 Å) | H180 (22.37 Å) |
| 162 | V178 (22.79 Å) | V178 (22.79 Å) | T3 (22.79 Å) |
| 163 | A100 (23.19 Å) | A100 (23.19 Å) | L58k (23.19 Å) |
| 164 | K59 (23.20 Å) | K59 (23.20 Å) | H61k,l (23.20 Å) |
| 165 | D133h (23.23 Å) | D133 (23.23 Å) | S36 (23.23 Å) |
| 166 | K96 (23.32 Å) | K96 (23.32 Å) | R64 (23.32 Å) |
| 167 | R64 (23.54 Å) | R64 (23.54 Å) | P55k (23.54 Å) |
| 168 | P176e (23.57 Å) | P176e (23.57 Å) | A98l (23.57 Å) |
| 169 | T35 (23.61 Å) | T35j (23.61 Å) | A56 (23.61 Å) |
| 170 | Q62h (24.10 Å) | Q62 (24.10 Å) | K34l (24.10 Å) |
| 171 | A98 (24.21 Å) | A98 (24.21 Å) | Q32l (24.21 Å) |
| 172 | D2 (24.93 Å) | D2 (24.93 Å) | D2 (24.93 Å) |
| 173 | H180 (25.52 Å) | H180 (25.52 Å) | A97 (25.52 Å) |
| 174 | A97 (25.70 Å) | A97 (25.70 Å) | Q60l (25.70 Å) |
| 175 | Q32 (25.71 Å) | Q32j (25.71 Å) | K59 (25.71 Å) |
| 176 | N99h (26.55 Å) | N99 (26.55 Å) | N99 (26.55 Å) |
| 177 | K34 (27.24 Å) | K34j (27.24 Å) | Q62 (27.24 Å) |
| 178 | A1 (27.76 Å) | A1 (27.76 Å) | A1 (27.76 Å) |
| 179 | S33h (28.10 Å) | S33j (28.10 Å) | S33l (28.10 Å) |

(a) Distance was calculated by finding the closest contact between the residue's heavy atoms and the acyl moiety carbon atoms of 'TesA:tetradecanoyl-ACP.

(b) Distance was calculated between the residue's Cβ atom (Cα for glycine, Cγ for H180) and the ω-1 atom of dodecanoyl-ACP.
(c) Residue excluded because it is part of the 'TesA catalytic triad.
(d) Residue excluded because they form the 'TesA oxyanion hole.
(e) Residue excluded because legacy version of IPRO could not handle mutations from proline
(f) Residue excluded because it was considered important for 'TesA function based on mutagenesis studies
(g) Residue excluded because it was within 4.5 Å of the thioester sulfur atom.

What is claimed is:

1. An unnatural, mutated protein comprising an amino acid sequence that is at least 85% identical to SEQ ID NO:1 and comprises a substitution at a position aligning to I107 of SEQ ID NO:1, a position aligning to R108 of SEQ ID NO:1, a position aligning to S122 of SEQ ID NO:1, a position aligning to M141 of SEQ ID NO:1, a position aligning to Y145 of SEQ ID NO:1, a position aligning to L146 of SEQ ID NO:1, or a combination thereof, wherein:
   the protein comprises a phenylalanine at the position aligning to Y145 of SEQ ID NO:1; and
   the protein has at least one of enhanced thioesterase activity and enhanced thioesterase specificity in catalyzing the hydrolysis of a medium-chain acyl-acyl carrier protein substrate or a medium-chain acyl-CoA substrate to yield a free fatty acid or a free fatty acid derivative compared to an unaltered protein of SEQ ID NO:1.

2. The protein of claim 1, wherein the protein further comprises at least one of:
   a phenylalanine at the position aligning to R108 of SEQ ID NO:1;
   a phenylalanine at a position aligning to L109 of SEQ ID NO:1;
   a methionine at the position aligning to S122 of SEQ ID NO:1;
   a leucine at the position aligning to M141 of SEQ ID NO:1;
   a proline at a position aligning to E142 of SEQ ID NO:1; and
   a proline at the position aligning to L146 of SEQ ID NO:1.

3. The protein of claim 1, wherein the protein further comprises at least two of:
   a phenylalanine at the position aligning to R108 of SEQ ID NO:1;
   a phenylalanine at a position aligning to L109 of SEQ ID NO:1;
   a methionine at the position aligning to S122 of SEQ ID NO:1;
   a leucine at the position aligning to M141 of SEQ ID NO:1;
   a proline at the position aligning to E142 of SEQ ID NO:1; and
   a proline at the position aligning to L146 of SEQ ID NO:1.

4. The protein of claim 1, wherein the protein further comprises at least two of:
   a phenylalanine at the position aligning to R108 of SEQ ID NO:1;
   a phenylalanine at a position aligning to L109 of SEQ ID NO:1;
   a methionine at the position aligning to S122 of SEQ ID NO:1; and
   a proline at the position aligning to L146 of SEQ ID NO:1.

5. The protein of claim 1, wherein the protein further comprises a phenylalanine at the position aligning to R108 of SEQ ID NO:1.

6. The protein of claim 5, wherein the protein further comprises at least one of:
   a phenylalanine at a position aligning to L109 of SEQ ID NO:1; and
   a proline at the position aligning to L146 of SEQ ID NO:1.

7. The protein of claim 5, wherein the protein comprises a phenylalanine at a position aligning to L109 of SEQ ID NO:1.

8. The protein of claim 5, wherein the protein comprises a proline at the position aligning to L146 of SEQ ID NO:1.

9. The protein of claim 5, wherein the protein comprises:
   a phenylalanine at a position aligning to L109 of SEQ ID NO:1; and
   a proline at the position aligning to L146 of SEQ ID NO:1.

10. The protein of claim 9, wherein the protein further comprises a methionine at the position aligning to S122 of SEQ ID NO:1.

11. The protein of claim 1, wherein the protein further comprises at least two of:
    a methionine at the position aligning to S122 of SEQ ID NO:1;
    a leucine at the position aligning to M141 of SEQ ID NO:1; and
    a proline at a position aligning to E142 of SEQ ID NO:1.

12. The protein of claim 1, wherein the protein further comprises at least one of:
    a leucine at the position aligning to M141 of SEQ ID NO:1; and
    a proline at a position aligning to E142 of SEQ ID NO:1.

13. The protein of claim 1, wherein the protein further comprises:
    a leucine at the position aligning to M141 of SEQ ID NO:1; and
    a proline at a position aligning to E142 of SEQ ID NO:1.

14. The protein of claim 13, wherein the protein further comprises a methionine at the position aligning to S122 of SEQ ID NO:1.

15. The protein of claim 1, wherein the protein comprises an amino acid sequence that is at least 90% identical to SEQ ID NO: 1.

16. The protein of claim 1, wherein the protein comprises an amino acid sequence that is at least 95% identical to SEQ ID NO: 1.

17. A gene construct encoding the protein of claim 1.

18. The gene construct of claim 17, comprising a nucleotide regulatory sequence operationally connected to nucleotides encoding the protein, wherein the regulatory sequence is dimensioned and configured to drive expression of the protein in a host cell transformed to contain the gene construct.

19. A host cell transformed to contain and express a gene construct encoding the protein of claim 1.

20. The host cell of claim 19, which is selected from the group consisting of a transformed microbe, a transformed eukaryote, a transformed prokaryote, and a transformed plant cell.

* * * * *

SEQUENCE LISTING

```
<160> NUMBER OF SEQ ID NOS: 3

<210> SEQ ID NO 1
<211> LENGTH: 190
<212> TYPE: PRT
<213> ORGANISM: Escherichia coli
<220> FEATURE:
<221> NAME/KEY: MISC_FEATURE
<222> LOCATION: (163)..(190)
<223> OTHER INFORMATION: Expression tag

<400> SEQUENCE: 1

Ala Asp Thr Leu Leu Ile Leu Gly Asp Ser Leu Ser Ala Gly Tyr Arg
1               5                   10                  15

Met Ser Ala Ser Ala Ala Trp Pro Ala Leu Leu Asn Asp Lys Trp Gln
            20                  25                  30

Ser Lys Thr Ser Val Val Asn Ala Ser Ile Ser Gly Asp Thr Ser Gln
        35                  40                  45

Gln Gly Leu Ala Arg Leu Pro Ala Leu Leu Lys Gln His Gln Pro Arg
    50                  55                  60

Trp Val Leu Val Glu Leu Gly Gly Asn Asp Gly Leu Arg Gly Phe Gln
65                  70                  75                  80

Pro Gln Gln Thr Glu Gln Thr Leu Arg Gln Ile Leu Gln Asp Val Lys
                85                  90                  95

Ala Ala Asn Ala Glu Pro Leu Leu Met Gln Ile Arg Leu Pro Ala Asn
            100                 105                 110

Tyr Gly Arg Arg Tyr Asn Glu Ala Phe Ser Ala Ile Tyr Pro Lys Leu
        115                 120                 125

Ala Lys Glu Phe Asp Val Pro Leu Leu Pro Phe Phe Met Glu Glu Val
    130                 135                 140

Tyr Leu Lys Pro Gln Trp Met Gln Asp Asp Gly Ile His Pro Asn Arg
145                 150                 155                 160

Asp Ala Gln Pro Phe Ile Ala Asp Trp Met Ala Lys Gln Leu Gln Pro
                165                 170                 175

Leu Val Asn His Asp Ser Leu Glu His His His His His His
            180                 185                 190

<210> SEQ ID NO 2
<211> LENGTH: 627
<212> TYPE: DNA
<213> ORGANISM: Escherichia coli
<220> FEATURE:
<221> NAME/KEY: CDS
<222> LOCATION: (1)..(624)
<220> FEATURE:
<221> NAME/KEY: mat_peptide
<222> LOCATION: (79)..(624)

<400> SEQUENCE: 2 atg atg aac ttc aac aat gtt ttc cgc tgg cat ttg ccc ttc ctg ttt      48
Met Met Asn Phe Asn Asn Val Phe Arg Trp His Leu Pro Phe Leu Phe
    -25                 -20                 -15 ctg gtc ctg tta acc ttc cgt gcc gcc gca gcg gac acg tta ttg att      96
Leu Val Leu Leu Thr Phe Arg Ala Ala Ala Ala Asp Thr Leu Leu Ile
```

```
                -10                 -5                 -1  1                 5
ctg ggt gat agc ctg agc gcc ggg tat cga atg tct gcc agc gcg gcc            144
Leu Gly Asp Ser Leu Ser Ala Gly Tyr Arg Met Ser Ala Ser Ala Ala
            10                  15                  20 tgg cct gcc ttg ttg aat gat aag tgg cag agt aaa acg tcg gta gtc            192
Trp Pro Ala Leu Leu Asn Asp Lys Trp Gln Ser Lys Thr Ser Val Val
            25                  30                  35 aat gcc agc atc agc ggc gac acc tcg caa caa ggg ctg gcg cgc ctt            240
Asn Ala Ser Ile Ser Gly Asp Thr Ser Gln Gln Gly Leu Ala Arg Leu
            40                  45                  50 ccg gct ctg ctg aaa cag cat cag ccg cgt tgg gtg ctg gtt gaa ctg            288
Pro Ala Leu Leu Lys Gln His Gln Pro Arg Trp Val Leu Val Glu Leu
55                  60                  65                  70 ggc ggc aat gac ggt ttg cgt ggt ttt cag cca cag caa acc gag caa            336
Gly Gly Asn Asp Gly Leu Arg Gly Phe Gln Pro Gln Gln Thr Glu Gln
                75                  80                  85 acg ctg cgc cag att ttg cag gat gtc aaa gcc gcc aac gct gaa cca            384
Thr Leu Arg Gln Ile Leu Gln Asp Val Lys Ala Ala Asn Ala Glu Pro
            90                  95                  100 ttg tta atg caa ata cgt ctg cct gca aac tat ggt cgc cgt tat aat            432
Leu Leu Met Gln Ile Arg Leu Pro Ala Asn Tyr Gly Arg Arg Tyr Asn
            105                 110                 115 gaa gcc ttt agc gcc att tac ccc aaa ctc gcc aaa gag ttt gat gtt            480
Glu Ala Phe Ser Ala Ile Tyr Pro Lys Leu Ala Lys Glu Phe Asp Val
            120                 125                 130 ccg ctg ctg ccc ttt ttt atg gaa gag gtc tac ctc aag cca caa tgg            528
Pro Leu Leu Pro Phe Phe Met Glu Glu Val Tyr Leu Lys Pro Gln Trp
135                 140                 145                 150 atg cag gat gac ggt att cat ccc aac cgc gac gcc cag ccg ttt att            576
Met Gln Asp Asp Gly Ile His Pro Asn Arg Asp Ala Gln Pro Phe Ile
                155                 160                 165 gcc gac tgg atg gcg aag cag ttg cag cct tta gta aat cat gac tca            624
Ala Asp Trp Met Ala Lys Gln Leu Gln Pro Leu Val Asn His Asp Ser
            170                 175                 180 taa                                                                        627

<210> SEQ ID NO 3
<211> LENGTH: 208
<212> TYPE: PRT
<213> ORGANISM: Escherichia coli

<400> SEQUENCE: 3

Met Met Asn Phe Asn Asn Val Phe Arg Trp His Leu Pro Phe Leu Phe
            -25                 -20                 -15

Leu Val Leu Leu Thr Phe Arg Ala Ala Ala Ala Asp Thr Leu Leu Ile
-10                 -5                  -1  1                 5

Leu Gly Asp Ser Leu Ser Ala Gly Tyr Arg Met Ser Ala Ser Ala Ala
            10                  15                  20

Trp Pro Ala Leu Leu Asn Asp Lys Trp Gln Ser Lys Thr Ser Val Val
            25                  30                  35

Asn Ala Ser Ile Ser Gly Asp Thr Ser Gln Gln Gly Leu Ala Arg Leu
            40                  45                  50

Pro Ala Leu Leu Lys Gln His Gln Pro Arg Trp Val Leu Val Glu Leu
55                  60                  65                  70

Gly Gly Asn Asp Gly Leu Arg Gly Phe Gln Pro Gln Gln Thr Glu Gln
                75                  80                  85

Thr Leu Arg Gln Ile Leu Gln Asp Val Lys Ala Ala Asn Ala Glu Pro
            90                  95                  100
```

```
Leu Leu Met Gln Ile Arg Leu Pro Ala Asn Tyr Gly Arg Arg Tyr Asn
        105                 110                 115

Glu Ala Phe Ser Ala Ile Tyr Pro Lys Leu Ala Lys Glu Phe Asp Val
        120                 125                 130

Pro Leu Leu Pro Phe Phe Met Glu Glu Val Tyr Leu Lys Pro Gln Trp
135                 140                 145                 150

Met Gln Asp Asp Gly Ile His Pro Asn Arg Asp Ala Gln Pro Phe Ile
                155                 160                 165

Ala Asp Trp Met Ala Lys Gln Leu Gln Pro Leu Val Asn His Asp Ser
                170                 175                 180
```